US007858753B2

United States Patent

(12) United States Patent
Ellis et al.

(10) Patent No.: US 7,858,753 B2
(45) Date of Patent: Dec. 28, 2010

(54) IMMUNOGLOBULINS

(75) Inventors: Jonathan Henry Ellis, Stevenage (GB); Alexandre Eon-Duval, Fenil-sur-Corsier (CH); Volker Germaschewski, Stevenage (GB); Christopher Plumpton, Stevenage (GB); Nicholas Timothy Rapson, Cambridge (GB); Michael Robert West, Stevenage (GB)

(73) Assignee: Glaxo Group Limited (GB)

( * ) Notice: Subject to any disclaimer, the term of this patent is extended or adjusted under 35 U.S.C. 154(b) by 550 days.

(21) Appl. No.: 10/594,293

(22) PCT Filed: Mar. 29, 2005

(86) PCT No.: PCT/GB2005/001147

§ 371 (c)(1),
(2), (4) Date: Aug. 7, 2007

(87) PCT Pub. No.: WO2005/095457

PCT Pub. Date: Oct. 13, 2005

(65) Prior Publication Data

US 2007/0286861 A1 Dec. 13, 2007

(30) Foreign Application Priority Data

Mar. 30, 2004 (GB) ................................ 0407193.2
Mar. 30, 2004 (GB) ................................ 0407197.3

(51) Int. Cl.
*C07K 16/00* (2006.01)

(52) U.S. Cl. ................................ 530/387.9; 424/133.1

(58) Field of Classification Search ....................... None
See application file for complete search history.

(56) References Cited

U.S. PATENT DOCUMENTS 6,706,266 B1 3/2004 Life

FOREIGN PATENT DOCUMENTS

JP 6345667 12/1994
WO WO99/48523 9/1999

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology (2002) 320, 415-428.*
Holm et al. Molecular Immunology (2007) 44, 1075-1084.*
Chen et al. J. Mol. Bio. (1999) 293, 865-881.*
Wu et al. J. Mol. Biol. (1999) 294, 151-162.*
Mueller et al. (PNAS 1992) vol. 89. pp. 11832-11836.*
Ogata, et al., "Oncostatin M is produced during pregnancy by decidual cells and stimulates the release of HCG," *Molecular Human Reproduction* (Aug. 2000) 6(8): 75-757.
Carroll, et al., "Antagonism of the IL-6 cytokine subfamily—a potential strategy for more effective therapy in rheumatoid arthritis" Inflammation Research, (1997) 47(1):1-7.
Barton, et al. Cancer Cachexia is Mediated in Part by the Induction of IL-6 Like Cytokines From the Spleen, Cytokine, vol. 16, No. 6, Sep. 21, 2001, pp. 251-257.
Deller, et al., Crystal structure and functional dissection of the cytostatic cytokine oncostatin M, Structure, vol. 8, No. 8, 2000, pp. 863-874.
Plater-Zyberk, C., et al. Amelioration of Arthritis in Two Murine Models Using Antibodies to Oncostatin M, Arthritis & Rheumatism, vol. 44, No. 11, Nov. 2001, pp. 2697-2702.
Schildbach, et al., Modulation of Antibody affinity by a non-contact residue, Protein Science, 1993, 2, pp. 206-214.
Westendorf, et al., Groeth Regulatory Pathways in Myeloma, Journal of Immunology, 1996, 157: 3801-3088.

* cited by examiner

*Primary Examiner*—Larry R. Helms
*Assistant Examiner*—Meera Natarajan
(74) *Attorney, Agent, or Firm*—Jason C. Fedon; William T. Han

(57) ABSTRACT

The present invention concerns immunoglobulins, such as antibodies, which specifically bind Oncostatin M (OSM), particularly human OSM (hOSM) and modulate the interaction between OSM and gp130. In typical embodiments, OSM is glycosylated. The invention also concerns antibodies that modulate the interaction between both Site II and Site III of OSM and their respective interacting partners. Further disclosed are pharmaceutical compositions, screening and medical treatment methods.

23 Claims, 37 Drawing Sheets

IMMUNOGLOBULINS

This application is a §371 national phase entry of International Application No. PCT/GB2005/001147 filed Mar. 29, 2005, which claims priority to International Appn. No. GB0407197.3 and GB0407193.2, filed Mar. 30, 2004.

FIELD OF THE INVENTION

The present invention relates to immunoglobulins that specifically bind Oncostatin M (OSM) and in particular human OSM (hOSM). More particularly, the present invention relates to antibodies that specifically bind hOSM. The present invention also concerns methods of treating diseases or disorders with said immunoglobulins, pharmaceutical compositions comprising said immunoglobulins and methods of manufacture. Other aspects of the present invention will be apparent from the description below.

BACKGROUND OF THE INVENTION

Oncostatin M is a 28 KDa glycoprotein that belongs to the interleukin 6 (IL-6) family of cytokines which includes IL-6, Leukaemia Inhibitory Factor (LIF), ciliary neurotrophic factor (CNTF), cardiotropin-1 (CT-1) and cardiotrophin-1 like cytokine (See Kishimoto T et al (1995) Blood 86: 1243-1254), which share the gp130 transmembrane signalling receptor (See Taga T and Kishimoto T (1997) Annu. Rev. Immunol. 15: 797-819). OSM was originally discovered by its ability to inhibit the growth of the melanoma cell line A375 (See Malik N (1989) et al Mol Cell Biol 9: 2847-2853). Subsequently, more effects were discovered and it was found to be a multifunctional mediator like other members of the IL-6 family. OSM is produced in a variety of cell types including macrophages, activated T cells (See Zarling J M (1986) PNAS (USA) 83: 9739-9743), polymorphonuclear neutrophils (See Grenier A et al (1999) Blood 93:1413-1421), eosinophils (See Tamura S et al (2002) Dev. Dyn. 225: 327-31), dendritic cells (See Suda T et al (2002) Cytokine 17:335-340). It pancreas, kidney, testes, spleen stomach and brain (See Znoyko I et al (2005) Anat Rec A Discov Mol Cell Evol Biol 283: 182-186), and bone marrow (See Psenak O et al (2003) Acta Haematol 109: 68-75) Its principle biological effects include activation of endothelium (See Brown T J et al (1993) Blood 82: 33-7), activation of the acute phase response (See Benigni F et al (1996) Blood 87: 1851-1854), induction of cellular proliferation or differentiation, modulation of inflammatory mediator release and haematopoesis (See Tanaka M et al (2003) 102: 3154-3162), re-modelling of bone (See de Hooge A S K (2002) Am J Pathol 160: 1733-1743) and, promotion of angiogenesis (See Vasse M et al (1999) Arterioscler Thromb Vasc Biol 19:1835-1842) and wound healing.

Receptors for OSM (OSM receptor β, "OSMRβ") are expressed on a wide range of cells including epithelial cells, chondrocytes, fibroblasts (See Langdon C et al (2003) J Immunol 170: 548-555), neuronal smooth muscle, lymph node, bone, heart, small intestine, lung and kidney (See Tamura S et al (2002) Mech Dev 115: 127-131) and endothelial cells. Several lines of evidence suggest that endothelial cells are a primary target for OSM. These cells express 10 to 20 fold higher numbers of both high and low affinity receptors and exhibit profound and prolonged alterations in phenotype following stimulation with OSM (See Modur V et al (1997) J Clin Invest 100: 158-168). In addition, OSM is a major autocrine growth factor for Kaposi's sarcoma cells, which are thought to be of endothelial origin (See Murakami-Mori K et al (1995) J Clin Invest 96:1319-1327).

In common with other IL-6 family cytokines, OSM binds to the transmembrane signal transducing glycoprotein gp130. A key feature of the gp130 cytokines is the formation of oligomeric receptor complexes that comprise gp130 and one or more co-receptors depending on the ligand (Reviewed in Heinrich P C et al (2003) Biochem J. 374: 1-20). As a result, these cytokines can mediate both the shared and unique biological activities in vitro and in vivo depending on the composition of the receptor complex formed. Human OSM (hOSM) differs from the other IL-6 cytokines in that it can form complexes with gp130 and either one of the two co-receptors, LIFR or the oncostatin receptor (OSMR). FIG. 1 illustrates the interaction between hOSM and gp130, LIFR and OSMR. The crystal structure of hOSM has been solved and shown to comprise a four α helical bundle with two potential glycosylation sites. Two separate ligand binding sites have been identified by site-directed mutagenesis on the hOSM molecule (See Deller M C et al (2000) Structural Fold Des. 8:863-874). The first, called Site II (sometimes "site 2") interacts with gp130 and the second site, called Site III (sometimes "site 3"), at the opposite end of the molecule interacts with either LIFR or OSMR. Mutagenesis experiments have shown that the binding sites for LIFR and OSMR are almost identical but that a single amino acid mutation can discriminate between the two.

OSM is synthesised as a proprotein containing a hydrophobic 25 amino acid (AA) N terminal signal sequence and a C-terminal propeptide of 33 AA, both of which are cleaved to generate mature OSM. The OSM proprotein does have biological activity but this is significantly increased by cleavage of the C terminal propeptide (see Bruce A. G. et al (1992) Prog. Growth Factor Res. 4: 157-170, Malik N et al (1989) Mol. Cell Biol. 9: 2847-2853). OSM has been described as a "compact, barrel-shaped molecule" with dimensions of approximately 20 Å×27 Å×56 Å. There are four alpha helical regions (helix A 10-37AA, helix B 67-90AA, helix C 105-131AA and helix D 159-185AA, numbering of AA starts after removal of the signal sequence). Helices A and C contain "kinks". The helices are joined by two overhand loops (AB loop 38-66M, CD loop 130-158 AA) and are arranged as two anti-parallel pairs (A-D and B-C). (See Deller M. C et al (2000) Structure 8; 863-874).

It appears that OSM binding via Site II to gp130 allows binding of another OSM molecule to gp130 by a Site III interaction. OSM will also bind to either LIFR or OSMR via Site II. Thus OSM forms a complex with its receptor consisting of; one gp130, one LIFR or OSMR, and two OSM molecules. (See Sporeno E (1994) J. Biol. Chem. 269: 10991-10995, Staunton D et al (1998) Prot. Engineer 11:1093-1102 and Gearing D. P (1992) Science 225:306-312).

Using mutagenesis, the important residues for Site II OSM-gp130 binding are Gln20, Gly120, Gln16 and Asn124. For Site III OSM-OSMR binding, the important residues are Phe160 and Lys163. The OSM Site II interaction is therefore dependent on Gln20, Gly120, Asn124 and to a lesser extent Gln16 on hOSM. Three complementary residues in gp130 (Phe169, Tyr196 and Glu282) have been identified as of particular note in the interaction between OSM and gp130. (See Deller M et al (2000) Structure 8:863-874, Aasland D et al (2002) J. Mol. Biol 315: 637-646, Timmermann A et al (2000) FEBS Lett. 468: 120-124).

The amino acid sequence starting at position 1 for hOSM is set forth as SEQ. I.D. NO: 13

(SEQ. I.D. NO:13)
MGVLLTQRTLLSLVLALLFPSMASMAAIGSCSKEYRVLLGQLQKQTDLMQ

DTSRLLDPYIRIQGLDVPKLREHCRERPGAFPSEETLRGLGRRGFLQTLN

ATLGCVLHRLADLEQRLPKAQDLERSGLNIEDLEKLQMARPNILGLRNNI

YCMAQLLDNSDTAEPTKAGRGASQPPTPTPASDAFQRKLEGCRFLHGYHR

FMHSVGRVFSKWGESPNRSRRHSPHQALRKGVRRTRPSRKGKRLMTRGQL

PR..

Site II residues of particular note are highlighted in bold and underlined

A cDNA encoding hOSM is set forth in SEQ. I.D. NO:14.

(SEQ. I.D. NO:14)
ATGGGGGTACTGCTCACACAGAGGACGCTGCTCAGTCTGGTCCTTGCACT

CCTGTTTCCAAGCATGGCGAGCATGGCGGCTATAGGCAGCTGCTCGAAAG

AGTACCGCGTGCTCCTTGGCCAGCTCCAGAAGCAGACAGATCTCATGCAG

GACACCAGCAGACTCCTGGACCCCTATATACGTATCCAAGGCCTGGATGT

TCCTAAACTGAGAGAGCACTGCAGGGAGCGCCCCGGGGCCTTCCCCAGTG

AGGAGACCCTGAGGGGGCTGGGCAGGCGGGGCTTCCTGCAGACCCTCAAT

GCCACACTGGGCTGCGTCCTGCACAGACTGGCCGACTTAGAGCAGCGCCT

CCCCAAGGCCCAGGATTTGGAGAGGTCTGGGCTGAACATCGAGGACTTGG

AGAAGCTGCAGATGGCGAGGCCGAACATCCTCGGGCTCAGGAACAACATC

TACTGCATGGCCCAGCTGCTGGACAACTCAGACACGGCTGAGCCCACGAA

GGCTGGCCGGGGGCCTCTCAGCCGCCCACCCCCACCCCTGCCTCGGATG

CTTTTCAGCGCAAGCTGGAGGGCTGCAGGTTCCTGCATGGCTACCATCGC

TTCATGCACTCAGTGGGGCGGGTCTTCAGCAAGTGGGGGGAGAGCCCGAA

CCGGAGCCGGAGACACAGCCCCCACCAGGCCCTGAGGAAGGGGTGCGCA

GGACCAGACCCTCCAGGAAAGGCAAGAGACTCATGACCAGGGGACAGCTG

CCCCGGTAG

Rheumatoid arthritis (RA) comprises a syndrome of distinct but inter-connected pathogenic processes. These are: local and systemic inflammation, proliferation of synovial cells, angiogenesis and matrix deposition leading to formation of pannus tissue which invades and destroys cartilage and bone, resulting in deformity and disability. Underpinning this pathology is the chronic release of cytokines and inflammatory mediators from cells that enter and take up residence in the inflamed joint and from endogenous joint tissue cells (See Firestein G (2003) in Rheumatology. Eds Hochberg, Silman, Smolen, Weinblatt and Weisman. Pub. Mosby. 855-884). The initiating events in RA are unknown but a wealth of evidence suggests that they involve activation of T lymphocytes by either a foreign or autologous "self" antigen (See Firestein G (2004) J Clin Invest 114: 471-4). The extent to which T cells are required to maintain the ongoing disease processes once they have been initiated is also uncertain although therapeutic agents such as CTLA4lg, which specifically target T cells can be effective in advanced disease (See Kremer J M et al (2003) New Engl J Med 349: 1907-15, Moreland L et al (2004) Annual meeting of the American College of Rheumatology Abstract 1475).

The earliest events in the development of rheumatoid synovitis involve recruitment of mononuclear and polymorphonuclear cells to cross the endothelium in capillaries in the synovial-lining layer. While the polymorphs migrate into synovial fluid (SF) the lymphocytes remain close to the capillaries and may subsequently become organised into ectopic lymphoid follicles. This influx of immune cells is followed by proliferation of fibroblast-like synoviocytes (FLS). Unlike their normal counterparts, RA FLS appear to have escaped from the regulatory processes that result in arrest of proliferation and apoptosis leading to their continuing accumulation (See Yamanishi Y et al (2004) Arthritis Res Ther 7: 12-18). Furthermore, the emerging pannus tissue now develops new blood vessels supported by extracellular matrix to allow further expansion. This process involving fibroblast proliferation, matrix-remodelling and angiogenesis closely resembles an uncontrolled wound-healing event. Monocytes migrate into the developing pannus tissue and undergo differentation into macrophages with a chronically activated phenotype. Similarly B cells undergo terminal differentiation to form long-lived plasma cells which secrete antibodies including rheumatoid factors. The ability of the inflamed synovium to sustain local differentation of myeloid and lymphoid cells is based, in part, on local production of growth factors such as GMCSF and IL-6. Both the FLS and resident mononuclear leukocytes release soluble factors that stimulate further recruitment of inflammatory cells from the blood and, critically, drive the next step in the disease process—the destruction of articular cartilage and re-modelling of bone. Pannus tissue is invasive. Its leading edge secretes destructive enzymes such as MMPs and cytokines that alter the phenotype of cells which maintain the structural integrity of cartilage and bone. As a result, proteoglycans are lost and type II collagen is irreversibly cleaved leading to weakening and loss of cartilage. Bone also undergoes a number of profound changes, which include focal erosions, sub-chondral osteoporosis. Ultimately these changes result in the characteristic deformity and subluxation of the joints seen in advanced RA (See Gordon D and Hastings D (2003) in Rheumatology. Eds Hochberg, Silman, Smolen, Weinblatt and Weisman. Pub. Mosby. 765-780).

RA is a systemic disease, probably as a result of the passage of inflammatory mediators from the joint into the blood. This affects many organ systems in the body including skin, eyes, liver, kidneys, brain and the vascular lining, leading to increased morbidity and mortality (See Matteson E L (2003) in Rheumatology. Eds Hochberg, Silman, Smolen, Weinblatt and Weisman. Pub. Mosby. 781-792). Much of the excess mortality is due to cardiovascular disease caused by atherosclerosis since many of the pathogenic processes involved in the development of rheumatoid synovitis are common to the formation of atherosclerotic plaques.

Treatments for RA aim to control pain reduce inflammation and arrest the processes that result in tissue destruction. Traditionally RA has been treated with non-steroidal anti-inflammatory drugs (NSAIDS), low doses of steroids and so-called disease modifying anti-rheumatic drugs (DMARDS). Low levels of efficacy, slow onset, toxicity, poor tolerability and increasing resistance over time plague the use of these treatments which include methotrexate (MTX), sulphasalazine, gold and Leflunomide. More recently, the introduction of biologic drugs such as Enbrel™, Remicide™ and Humira™, which inhibit the cytokine Tumour Necrosis Factor (TNF), have been a significant advance (See Roberts L and McColl G J (2004) Intern Med J 34:687-93).

It is therefore an object of the present invention to provide a therapeutic approach to the treatment of RA and other diseases and disorders, particularly chronic inflammatory diseases and disorders such as osteoarthritis and psoriasis. In particular it is an object of the present invention to provide immunoglobulins, especially antibodies that specifically bind OSM (e.g. hOSM, particularly Site II thereof) and modulate (i.e. inhibit or block) the interaction between OSM and gp130 in the treatment of diseases and disorders responsive to modulation of that interaction.

There is increasing evidence to support the hypothesis that modulating OSM-gp130 interaction maybe of benefit in the treatment of such diseases and disorders.

Clinical Evidence

OSM is found in the SF of human RA patients (See Hui W et al (1997) 56: 184-7). These levels correlate with; the number of neutrophils in SF, levels of TNF alpha (sometimes "TNF") in SF, and markers of cartilage destruction (Manicourt D H et al (2000) Arthritis Rheum 43: 281-288). Furthermore, the synovial tissue from RA patients secretes OSM spontaneously ex vivo (See Okamoto H et al (1997) Arthritis and Rheumatism 40: 1096-1105). It has also been demonstrated that OSM is present in synovial macrophages (Cawston T E et al (1998) Arthritis Rheum 41: 1760-1771) and as discussed earlier, OSM receptors and gp130 are expressed on endothelial cells, synovial fibroblasts, chonodrocytes and osteoblasts. Furthermore, cells infiltrating atherosclerotic plaques and aortic aneurysms express OSM suggesting an association of this cytokine with chronic inflammation (See Mirshahi F et al (2001) Ann NY Acad Sci 936: 621-4).

In Vitro Evidence

Endothelial cells express ten to twenty times the number of OSM receptors than other cell types (See Brown T J et al (1991) J Immunol 147: 2175-2180, Linsley P S et al (1989) J Biol Chem 264: 4282-4289). OSM alone, or synergistically in combination with other cytokines, activates endothelium to release cytokines and chemokines and bind neutrophils, monocytes and lymphocytes mediating their extravasation into synovial tissue (See Modur V et al (1997) J Clin Invest 100: 158-168). OSM has also been demonstrated to be a potent stimulator of angiogenesis (See Vasse M et al (1999) Aterioscler Thromb Vasc Biol 19: 1835-1842) and activation and proliferation of synovial fibroblast (FLS) cells (thus facilitating the formation of pannus tissue, the release of IL-6, MMPs) and acts synergistically with TNF and IL-1 to induce this mediator release (See Langdon C et al (2000) Am J Pathol 157: 1187-1196). OSM has also been demonstrated to induce (with IL-1) collagen and proteoglycan release from cartilage (See Cawston T et al (1995) Biochem Biophys Res Commun 215: 377-385). Furthermore, OSM induces acute phase protein release and production of IL-6 receptor from hepatocytes (See Cichy J et al (1997) J Immunol 159: 5648-5643, Kurash J K (2004) Exp Cell Res 292: 342-58) and may therefore contribute to the systemic effects of rheumatoid inflammation including fatigue. In addition, OSM induces osteoclast differentiation and activity in vitro (See Palmqvist P et al (2002) J Immunol 169: 3353-3362).

In Vivo Evidence

Adenoviral expression of murine OSM (mOSM) in the joints of normal mice results in a severe inflammatory and erosive arthritis (See Langdon C et al (2000) Am J Pathol 157: 1187-1196). Similarly aggressive disease is seen in knockout mice lacking TNF, IL-1, IL-6 and iNOS following adenoviral mOSM delivery (See de Hooge A S K et al (2003) Arthritis and Rheumatism 48:1750-1761), demonstrating that OSM can mediate all aspects of arthritis pathology. Mouse OSM expression using an adenovirally expressed mOSM vector causes damage to the growth plate typical of Juvenile Idiopathic Arthritis (See de Hooge A S K et al (2003) Arthritis and Rheumatism 48:1750-1761). In an experimental model of collagen induced arthritis, an anti-OSM antibody administered therapeutically to mice prevented all further progression of disease. Similar results were seen when anti-OSM was administered prophylatically to mice with pristane induced arthritis, a relapsing/remitting model reminiscent of the human disease (See Plater-Zyberk C et al (2001) Arthritis and Rheumatism 44: 2697-2702). In monkeys, OSM injected subcutaneously induces an acute phase response and local chronic inflammation (See Loy J K et al (1999) Toxicol Pathol 27: 151-155). OSM has been demonstrated to induce mononuclear and PMN infiltration and proteoglycan release when injected into goat joints (See Bell M C et al (1999) Arthritis Rheum 42: 2543-2551). Transgenic over-expression of mOSM in mouse lymph nodes results in extrathymic T cell maturation, proliferation of memory T cells and failure to deplete autoimmune T cells (See Louis I et al (2003) Blood 102: 1397-1404). Transgenic over-expression of OSM in the pancreas causes extensive fibrosis similar to that seen in advanced RA synovium (See Malik N et al (1995) Mol Cell Biol 15: 2349-2358).

In WO99/48523, we disclose the use of OSM antagonists in the treatment of inflammatory diseases and disorders. This disclosure used an anti-mouse OSM antibody in a murine model of arthritis.

All patent and literature references disclosed within the present specification are expressly and entirely incorporated herein by reference.

SUMMARY OF THE INVENTION

The present inventors postulate that modulating (in particular blocking) the interaction between Site II of hOSM and gp130, with an antibody that specifically binds hOSM will modulate signalling by all of the potential OSM receptor complexes, effectively neutralising the biological activity of the cytokine to a therapeutically significant degree. Notwithstanding this, the present inventors have found that blockade of both the Site II and Site III sites of hOSM surprisingly improves neutralisation of this cytokine. Furthermore, the present inventors have found that the glycosylation of hOSM plays an unexpected role in the binding event between hOSM and an antibody that specifically binds hOSM.

The present invention therefore provides a therapeutic antibody 15E10 or 10D3 (which maybe chimaeric, human, humanised, bispecific or antigen binding fragments thereof) which specifically binds hOSM and interacts with Site II of hOSM. See Table A below.

In one embodiment of the present invention there is provided a therapeutic antibody or antigen binding fragment thereof which specifically binds hOSM and modulates (i.e inhibits or blocks) the interaction between Site II of hOSM and gp130. In some embodiments, the therapeutic antibody or antigen binding fragment thereof specifically binds Site II of hOSM.

In another embodiment, there is provided a therapeutic antibody or antigen binding fragment thereof which specifically binds hOSM and comprises the following CDRH3: SEQ. I.D. NO: 3 or SEQ. I.D. NO:42.

In another embodiment of the present invention there is provided a therapeutic antibody or antigen binding fragment thereof which specifically binds to hOSM and comprises the following CDRs:

CDRH1: SEQ. I.D. NO: 1

CDRH2: SEQ. I.D. NO: 2

CDRH3: SEQ. I.D. NO: 3

CDRL1: SEQ. I.D. NO: 4

CDRL2: SEQ. I.D. NO: 5

CDRL3: SEQ. I.D. NO: 6

In another embodiment of the present invention there is provided a therapeutic antibody or antigen binding fragment thereof which specifically binds to hOSM and comprises the following CDRs:

CDRH1: SEQ. I.D. NO: 40

CDRH2: SEQ. I.D. NO: 41

CDRH3: SEQ. I.D. NO: 42

CDRL1: SEQ. I.D. NO: 43

CDRL2: SEQ. I.D. NO: 44

CDRL3: SEQ. I.D. NO: 45

Throughout this specification, the terms "CDR", "CDRL1", "CDRL2", "CDRL3", "CDRH1", "CDRH2", "CDRH3" follow the Kabat numbering system as set forth in Kabat et al; *Sequences of proteins of Immunological Interest* NIH, 1987. Therefore the following defines the CDRs according to the invention:

CDR: Residues

CDRH1: 31-35B

CDRH2: 50-65

CDRH3: 95-102

CDRL1: 24-34

CDRL2: 50-56

CDRL3: 89-97

In another embodiment of the invention there is provided a murine therapeutic antibody or antigen binding fragment thereof comprising a $V_H$ domain having the sequence: SEQ. I.D. NO: 7 and a $V_L$ domain having the sequence: SEQ. I.D. NO: 8.

In another embodiment of the invention there is provided a murine therapeutic antibody or antigen binding fragment thereof comprising a $V_H$ domain having the sequence: SEQ. I.D. NO: 46 and a $V_L$ domain having the sequence: SEQ. I.D. NO: 47.

In one embodiment of the invention there is provided a humanised therapeutic antibody or antigen binding fragment thereof comprising a $V_H$ chain having the sequence set forth in SEQ. I.D. NO: 9 and a $V_L$ domain having the sequence set forth in SEQ. I.D. NO:10.

In one embodiment of the invention there is provided a humanised therapeutic antibody or antigen binding fragment thereof comprising a $V_H$ chain having the sequence set forth in SEQ. I.D. NO: 48 and a $V_L$ domain having the sequence set forth in SEQ. I.D. NO:49.

In another embodiment of the invention there is provided a humanised therapeutic antibody, which antibody comprises a heavy chain having the sequence set forth in SEQ. I.D. NO: 11 and a light chain having the sequence set forth in SEQ. I.D. NO:12.

In another embodiment of the invention there is provided a humanised therapeutic antibody, which antibody comprises a heavy chain having the sequence set forth in SEQ. I.D. NO: 50 and a light chain having the sequence set forth in SEQ. I.D. NO:51.

In another embodiment of the invention there is provided a humanised therapeutic antibody or antigen binding fragment thereof which modulates (i.e. inhibits or blocks) the interaction between hOSM and gp130.

In another embodiment of the invention there is provided an isolated $V_H$ domain of an antibody comprising (or consisting essentially of) SEQ. I.D. NO: 7 or SEQ. I.D. NO:9 or SEQ. I.D. NO:46 or SEQ. I.D. NO:48.

In another embodiment of the invention there is provided a therapeutic antibody or antigen binding fragment thereof comprising a $V_H$ domain selected from the group consisting of;

SEQ. I.D. NO: 7, SEQ. I.D. NO:9, SEQ. I.D. NO:46, SEQ. I.D. NO:48.

In another embodiment of the present invention there is provided a therapeutic antibody or antigen binding fragment thereof which competitively inhibits the binding of the therapeutic antibody comprising a CDRH3 of SEQ. I.D. NO:3.

In another embodiment of the invention there is provided a therapeutic antibody or antigen binding fragment thereof which competitively inhibits the binding of the therapeutic antibody comprising CDRs of SEQ. I.D. NO: 1, 2, 3, 4, 5 and 6 with hOSM.

In another embodiment there is provided therapeutic antibody or antigen binding fragment thereof which competitively inhibits the binding of the therapeutic antibody comprising a heavy chain of SEQ. I.D. NO:11 and a light chain of SEQ. I.D. NO:12 with hOSM.

In another embodiment of the invention there is provided a method of treating a human patient afflicted with a disease or disorder responsive to modulation of the interaction between hOSM and gp130 which method comprises the step of administering to said patient a therapeutically effective amount of the therapeutic antibody or antigen binding fragment thereof as described herein.

In another embodiment of the present invention there is provided a method of treating a human patient afflicted with an inflammatory disease or disorder which method comprises the step of administering to said patient a therapeutically effective amount of the therapeutic antibody or antigen binding fragment thereof as described herein.

In another embodiment of the present invention there is provided a method of treating a human patient afflicted with an arthritic disease, particularly rheumatoid arthritis, juvenile onset arthritis or osteoarthritis which method comprises the step of administering to said patient a therapeutically effective amount of the therapeutic antibody or antigen binding fragment thereof as described herein.

In another embodiment of the invention there is provided a method of reducing or preventing cartilage degradation in a human patient afflicted with (or susceptible to) such degradation which method comprises the step of administering a therapeutically effective amount of a therapeutic antibody or antigen binding fragment thereof to said patient as described herein.

In another embodiment of the present invention there is provided a method of reducing TNF alpha production in a patient afflicted with a disease or disorder responsive to TNF alpha reduction which method comprises administering to said patient a therapeutically effective amount of a therapeutic antibody or antigen binding fragment thereof as described herein In another embodiment of the invention there is provided a method of treating the extraarticular manifestations of an arthritic disease or disorder which method comprises the step of administering a therapeutically effective amount of a therapeutic antibody or antigen binding fragment thereof as described herein to the human patient afflicted with the extraarticular manifestations of an arthritic disease or disorder.

In another embodiment of the present invention there is provided a method of treating a human patient afflicted with a disease of endothelial cell origin which method comprises the steps of administering to said patient a therapeutically effective amount of a therapeutic antibody or antigen binding fragment thereof as described herein.

Use of the therapeutic antibody or antigen binding fragment thereof as described herein in the manufacture of a medicament for the treatment of diseases and disorders as described herein is also provided.

In another embodiment of the invention there is provided a process for the manufacture of a therapeutic antibody or antigen binding fragment thereof as described herein.

In another embodiment of the invention there is provided an assay (particularly an ELISA assay) for studying the interaction between OSM (particularly hOSM) and an interacting partner (such as gp130, LIFR, OSMR), which assay comprises the step of providing for said studying, a sample of glycosylated OSM (typically glycosylated by a vertebrate host cell such as mammalian host cell e.g. CHO glycosylated).

In a further embodiment of the present invention we provide a therapeutic antibody that specifically binds native glycosylated hOSM and modulates (i.e. inhibits or blocks) the interaction between native glycosylated hOSM and an interacting partner selected from the group consisting of gp130, LIFR, OSMRβ.

We further provide a method of producing a pharmaceutical composition comprising a therapeutic antibody which specifically binds hOSM and modulates (i.e. inhibits or blocks) the interaction between hOSM and gp130 which method comprises the steps of;

(a) providing a candidate antibody;
(b) providing glycosylated OSM (particularly hOSM produced by a recombinantly transformed or transfected mammalian host cell such as a recombinantly transformed CHO cell and/or native glycosylated hOSM);
(c) contacting the antibody of step (a) with hOSM of step (b) under conditions permissive for binding;
(d) determining whether the antibody of step (c) modulates the interaction between hOSM and gp130;
(e) optionally humanising said antibody of step (a) or (d);
(f) incorporating said antibody of step (d) or (e) into a pharmaceutical composition.

Other aspects, objects and advantages of the present invention will be apparent from the description below.

BRIEF DESCRIPTION OF THE DRAWINGS

FIG. 11 illustrates the KB assay of CHO produced hOSM, FIG. 12 of CHO produced cOSM, FIG. 13 of CHO produced hOSM in 25% human AB serum, FIG. 14 of CHO produced cOSM in 25% human AB serum, FIG. 15 of neutrophil OSM, FIG. 16 of OSM isolated from cells SF of RA patients.

FIG. 34b illustrates that two samples had particularly high OSM synovial fluid concentrations.

DETAILED DESCRIPTION OF THE INVENTION

1. Antibody Structures 1.1 Intact Antibodies

Figure 1:
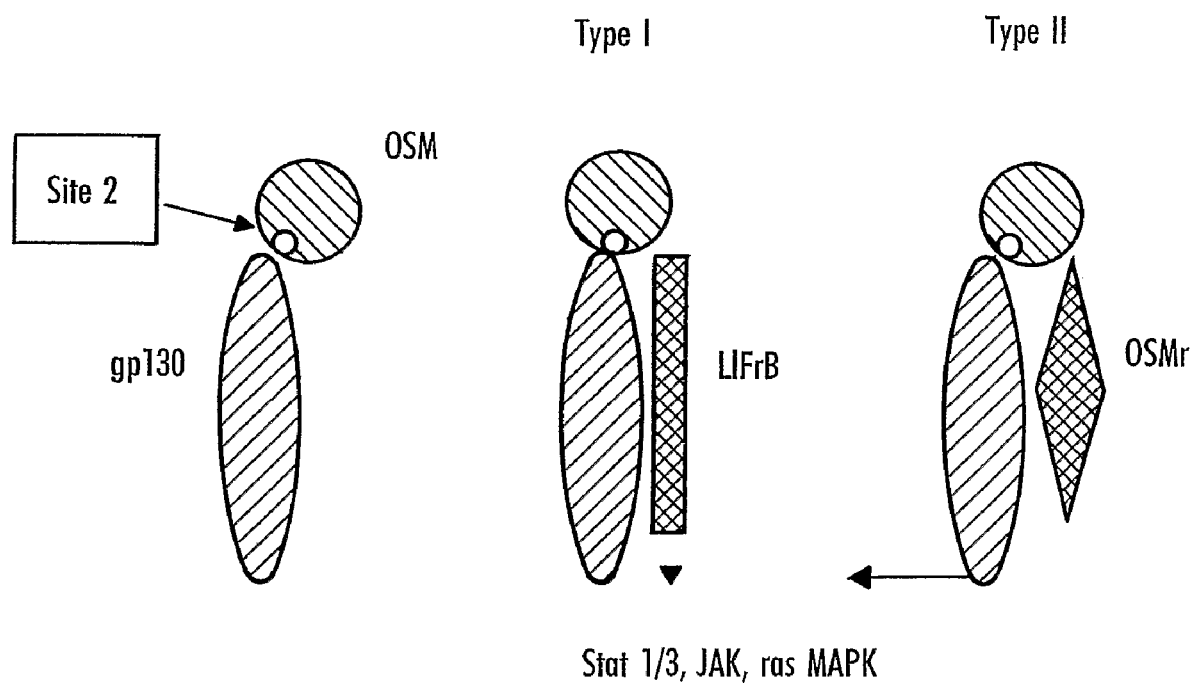
FIG. 1 is a schematic illustration of the interaction between OSM and gp130, LIFR and OSMRβ.

Intact antibodies are usually heteromultimeric glycoproteins comprising at least two heavy and two light chains. Aside from IgM, intact antibodies are heterotetrameric glycoproteins of approximately 150 Kda, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain ($V_H$) followed by a number of constant region. Each light chain has a variable domain ($V_L$) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

In one embodiment therefore we provide an intact therapeutic antibody that specifically binds hOSM, which antibody modulates the interaction between hOSM and gp130. The antibody may specifically bind Site II of hOSM and inhibit or block the interaction between hOSM and its corresponding residues on gp130 involved in OSM interaction. The ELISA protocol of the examples may be used to determine whether any particular antibody or antigen binding fragment thereof modulates the interaction between hOSM and gp130. The intact therapeutic antibody may comprise a constant region (either heavy or light) of any isotype or subclass thereof described supra. In one embodiment, the antibody is of the IgG isotype, particularly IgG1. The antibody may be rat, mouse, rabbit, primate or human. In one typical embodiment, the antibody is primate (such as cynomolgus, Old World monkey or Great Ape, see e.g. WO99/55369, WO93/02108) or human.

In another embodiment there is provided an intact therapeutic antibody comprising a CDRH3 of SEQ. I.D. NO: 3 or SEQ. I.D. NO:42. In another embodiment there is provided an intact therapeutic antibody comprising a variable region having CDRs of SEQ. I.D. NO: 1, 2,3,4,5 and 6 or a variable region of SEQ. I.D. NO:40, 41,42,43,44 and 45.

In another embodiment, there is provided a murine intact therapeutic antibody or antigen binding fragment thereof comprising a $V_H$ domain having the sequence of SEQ. I.D. NO: 7 and a $V_L$ domain of the sequence of SEQ. I.D. NO: 8.

In another embodiment, there is provided a murine intact therapeutic antibody or antigen binding fragment thereof comprising a $V_H$ domain having the sequence of SEQ. I.D. NO: 46 and a $V_L$ domain of the sequence of SEQ. I.D. NO: 47.

1.1.2 Human Antibodies

Human antibodies may be produced by a number of methods known to those of skill in the art. Human antibodies can be made by the hybridoma method using human myeloma or mouse-human heteromyeloma cells lines see Kozbor J. Immunol 133, 3001, (1984) and Brodeur, *Monoclonal Antibody Production Techniques and Applications*, pp 51-63 (Marcel Dekker Inc, 1987). Alternative methods include the use of phage libraries or transgenic mice both of which utilize human V region repertoires (see Winter G, (1994), Annu. Rev. Immunol 12, 433-455, Green L L (1999), J. Immunol. methods 231, 11-23).

Several strains of transgenic mice are now available wherein their mouse immunoglobulin loci has been replaced with human immunoglobulin gene segments (see Tomizuka K, (2000) PNAS 97, 722-727; Fishwild D. M (1996) Nature Biotechnol. 14, 845-851, Mendez M J, 1997, Nature Genetics, 15, 146-156). Upon antigen challenge such mice are capable of producing a repertoire of human antibodies from which antibodies of interest can be selected.

Of particular note is the Trimera™ system (see Eren R et al, (1998) Immunology 93:154-161) where human lymphocytes are transplanted into irradiated mice, the Selected Lymphocyte Antibody System (SLAM, see Babcook et al, PNAS (1996) 93:7843-7848) where human (or other species) lymphocytes are effectively put through a massive pooled in vitro antibody generation procedure followed by deconvulated, limiting dilution and selection procedure and the Xenomouse II™ (Abgenix Inc). An alternative approach is available from Morphotek Inc using the Morphodoma™ technology.

Phage display technology can be used to produce human antibodies (and fragments thereof), see McCafferty; Nature, 348, 552-553 (1990) and Griffiths A D et al (1994) EMBO 13:3245-3260. According to this technique antibody V domain genes are cloned in frame into either a major or minor coat of protein gene of a filamentous bacteriophage such as M13 or fd and displayed (usually with the aid of a helper phage) as functional antibody fragments on the surface of the phage particle. Selections based on the functional properties of the antibody result in selection of the gene encoding the antibody exhibiting those properties. The phage display technique can be used to select antigen specific antibodies from libraries made from human B cells taken from individuals afflicted with a disease or disorder described above or alternatively from unimmunized human donors (see Marks; J. Mol. Bio. 222, 581-597, 1991). Where an intact human antibody is desired comprising a Fc domain it is necessary to redone the phage displayed derived fragment into a mammalian expression vectors comprising the desired constant regions and establishing stable expressing cell lines.

The technique of affinity maturation (Marks; Bio/technol 10, 779-783 (1992)) may be used to improve binding affinity wherein the affinity of the primary human antibody is improved by sequentially replacing the H and L chain V regions with naturally occurring variants and selecting on the basis of improved binding affinities. Variants of this technique such as "epitope imprinting" are now also available see WO 93/06213. See also Waterhouse; Nucl. Acids Res 21, 2265-2266 (1993).

Thus in another embodiment there is provided a human intact therapeutic antibody or antigen binding fragment thereof which specifically binds hOSM and modulates (i.e. inhibits or blocks) the interaction between hOSM and gp130. In another embodiment there is provided a human intact therapeutic antibody or antigen binding fragment thereof which specifically binds Site II of hOSM and modulates (i.e. inhibits or blocks) the interaction between hOSM and gp130.

In another aspect there is provided a human intact therapeutic antibody or antigen binding fragment thereof comprising a CDRH3 of SEQ. I.D. NO: 3 or SEQ. I.D. NO:42 which specifically binds hOSM and modulates (i.e. inhibits or blocks) the interaction between hOSM and gp130. In another embodiment there is provided a human intact therapeutic antibody or antigen binding fragment thereof comprising a variable region having CDRs of SEQ. I.D. NO: 1, 2, 3, 4, 5 and 6 or a variable region having SEQ. I.D. NO:40, 41,42,43, 44 and 45.

1.2 Chimaeric and Humanised Antibodies

The use of intact non-human antibodies in the treatment of human diseases or disorders carries with it the now well established problems of potential immunogenicity especially upon repeated administration of the antibody that is the immune system of the patient may recognise the non-human intact antibody as non-self and mount a neutralising response. In addition to developing fully human antibodies (see above) various techniques have been developed over the years to overcome these problems and generally involve reducing the composition of non-human amino acid sequences in the intact therapeutic antibody whilst retaining the relative ease in obtaining non-human antibodies from an immunised animal e.g. mouse, rat or rabbit. Broadly two approaches have been used to achieve this. The first are chimaeric antibodies, which generally comprise a non-human (e.g. rodent such as mouse) variable domain fused to a human constant region. Because the antigen-binding site of an antibody is localised within the variable regions the chimaeric antibody retains its binding affinity for the antigen but acquires the effector functions of the human constant region and are therefore able to perform effector functions such as described supra. Chimaeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody of the invention, e.g. DNA encoding SEQ. I.D. NO 1,2,3,4,5 and 6 described supra). Hybridoma cells serve as a typical source of such DNA. Once isolated, the DNA is placed into expression vectors which are then transfected into host cells such as *E. Coli*, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions see e.g. Morrison; PNAS 81, 6851 (1984).

The second approach involves the generation of humanised antibodies wherein the non-human content of the antibody is reduced by humanizing the variable regions. Two techniques for humanisation have gained popularity. The first is humanisation by CDR grafting. CDRs build loops close to the antibody's N-terminus where they form a surface mounted in a scaffold provided by the framework regions. Antigen-binding specificity of the antibody is mainly defined by the topography and by the chemical characteristics of its CDR surface. These features are in turn determined by the conformation of the individual CDRs, by the relative disposition of the CDRs, and by the nature and disposition of the side chains of the residues comprising the CDRs. A large decrease in immunogenicity can be achieved by grafting only the CDRs of a non-human (e.g. murine) antibodies ("donor" antibodies) onto a suitable human framework ("acceptor framework") and constant regions (see Jones et al (1986) Nature 321, 522-525 and Verhoeyen M et al (1988) Science 239, 1534-1536). However, CDR grafting per se may not result in the complete retention of antigen-binding properties and it is frequently found that some framework residues of the donor antibody need to be preserved (sometimes referred to as "backmutations") in the humanised molecule if significant antigen-binding affinity is to be recovered (see Queen C et al (1989) PNAS 86, 10,029-10,033, Co, M et al (1991) Nature 351, 501-502). In this case, human V regions showing the greatest sequence homology (typically 60% or greater) to the non-human donor antibody maybe chosen from a database in order to provide the human framework (FR). The selection of human FRs can be made either from human consensus or individual human antibodies. Where necessary key residues from the donor antibody are substituted into the human acceptor framework to preserve CDR conformations. Computer modelling of the antibody maybe used to help identify such structurally important residues, see WO99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan E. A. et al; (1991) Mol. Immunol. 28, 489-498 and Pedersen J. T. et al (1994) J. Mol. Biol. 235; 959-973). Therefore it is possible to reduce the immunogenicity of a non-human Fv by replacing exposed residues in its framework regions that differ from those usually found in human antibodies. Because protein antigenicity can be correlated with surface accessibility, replacement of the surface residues may be sufficient to render the mouse variable region "invisible" to the human immune system (see also Mark G. E. et al (1994) in *Handbook of Experimental Pharmacology vol* 113: *The pharmacology of monoclonal Antibodies*, Springer-Verlag, pp 105-134). This procedure of humanisation is referred to as "veneering" because only the surface of the antibody is altered, the supporting residues remain undisturbed. A further alternative approach is set out in WO04/006955.

Thus another embodiment of the invention there is provided a chimaeric therapeutic antibody comprising a non-human (e.g. rodent) variable domain fused to a human constant region (which maybe of a IgG isotype e.g. IgG1) which specifically binds hOSM and modulates the interaction between Site II of hOSM and gp130.

In another embodiment there is provided a chimaeric therapeutic antibody comprising a non-human (e.g. rodent) variable region and a human constant region (which maybe of an IgG isotype e.g. IgG1) which specifically binds hOSM, which antibody further comprises a CDRH3 of SEQ. I.D. NO:3 or SEQ. I.D. NO:42. Such antibodies may further comprise a human constant region of the IgG isotype, e.g. IgG1

In another embodiment there is provided a chimaeric therapeutic antibody comprising a non-human (e.g. rodent) variable region and a human constant region (which maybe of a IgG isotype e.g. IgG1) which specifically binds hOSM having the CDRs of SEQ. I.D. NO: 1, 2,3,4,5 and 6 or SEQ. I.D. NO:40, 41,42,43,44 and 45.

In another embodiment there is provided a humanised therapeutic antibody or antigen binding fragment thereof which specifically binds hOSM and modulates (i.e. inhibits or blocks) the interaction between Site II of hOSM and gp130.

In another embodiment there is provided a humanised therapeutic antibody or antigen binding fragment thereof which specifically binds hOSM and comprises a CDRH3 of SEQ. I.D. NO: 3 or SEQ. I.D. NO:42. Such antibodies may comprise a human constant region of the IgG isotype, e.g. IgG1.

In another embodiment there is provided a humanised therapeutic antibody or antigen binding fragment thereof which specifically binds hOSM and comprises CDRs of SEQ. I.D. NO: 1, 2,3,4,5 and 6 or SEQ. I.D. NO:40, 41,42,43,44 and 45. Such antibodies may comprise a human constant region of the IgG isotype, e.g. IgG1.

In another embodiment there is provided a humanised therapeutic antibody or antigen binding fragment thereof which specifically binds hOSM and modulates the interaction between hOSM and gp130 and comprises (or consists essentially of) the heavy chain of SEQ. I.D. NO: 11 and a light chain of SEQ. I.D. NO: 12.

In another embodiment there is provide a humanised therapeutic antibody or antigen binding fragment thereof which specifically binds hOSM and modulates the interaction between hOSM and gp130 which antibody comprises (or consists essentially of) a heavy chain of SEQ. I.D. NO:50 and a light chain of SEQ. I.D. NO:51.

In another embodiment there is provided a humanised therapeutic antibody or antigen binding fragment thereof which specifically binds hOSM and modulates the interaction between hOSM and gp130 wherein said antibody or fragment thereof comprises CDRH3 of SEQ. I.D. NO: 3 optionally further comprising CDRs of SEQ. I.D. NO: 1,2,4,5 and 6 wherein the residues at positions 28, 29, 30, 71 and 94 of the human acceptor heavy chain framework region and positions 49 and 71 of the human acceptor light chain framework are substituted by the corresponding residues found in the donor antibody framework from which CDRH3 is derived.

In another embodiment there is provided a humanised therapeutic antibody or antigen binding fragment thereof which specifically binds hOSM and modulates the interaction between hOSM and gp130 wherein said antibody or fragment thereof comprises CDRH3 of SEQ. I.D. NO: 42 optionally further comprising CDRs of SEQ. I.D. NO: 40,41,43,44,45 wherein the residues at positions 28,44,48,67,69,71,73 of the human acceptor heavy chain framework region and positions 36,38,46,47,71 of the human acceptor light chain framework are substituted by the corresponding residues found in the donor antibody framework from which CDRH3 is derived It will be apparent to those skilled in the art that the term "derived" is intended to define not only the source in the sense of it being the physical origin for the material but also to define material which is structurally identical to the material but which does not originate from the reference source. Thus "residues found in the donor antibody from which CDRH3 is derived" need not necessarily have been purified from the donor antibody.

In another embodiment there is provided a humanised therapeutic antibody or antigen binding fragment thereof which specifically binds hOSM wherein said antibody or fragment thereof comprises CDRH3 of SEQ. I.D. NO: 3 optionally further comprising CDRs of SEQ. I.D. NO: 1,2,4,5 and 6 wherein the human heavy chain framework comprises one or more (e.g. all) of the following residues (or a conservative substitute thereof):

| Position | Residue |
|---|---|
| 28 | S |
| 29 | L |
| 30 | T |
| 71 | K |
| 94 | K | and the human light chain comprises either or both of the following residues (or conservative substitute thereof);

| Position | Residue |
|---|---|
| 49 | E |
| 71 | Y |

In another embodiment there is provided a humanised therapeutic antibody or antigen binding fragment thereof which specifically binds hOSM wherein said antibody or fragment thereof comprises CDRs of SEQ. I.D. NO: 1,2,3,4,5 and 6 wherein the human heavy chain framework comprises one or more (e.g. all) of the following residues (or a conservative substitute thereof):

| Position | Residue |
|---|---|
| 28 | S |
| 29 | L |
| 30 | T |
| 71 | K |
| 94 | K | and the human light chain comprises either or both of the following residues (or conservative substitute thereof);

| Position | Residue |
|---|---|
| 49 | E |
| 71 | Y |

In another embodiment there is provided a humanised therapeutic antibody or antigen binding fragment thereof which specifically binds to hOSM wherein said antibody or fragment thereof comprises CDRH3 of SEQ. I.D. NO:42 optionally further comprising CDRs of SEQ. I.D. NO: 40,41, 43,44,45 wherein the human heavy chain framework comprises one or more (e.g. all) of the following residues (or a conservative substitute thereof):

| Position | Residue |
|---|---|
| 28 | I |
| 48 | I |
| 44 | K |
| 67 | A |
| 69 | L |
| 71 | V |
| 73 | K | and the human light chain comprises one or more (e.g. all) of the following residues (or conservative substitute thereof);

| Position | Residue |
|---|---|
| 36 | F |
| 38 | K |
| 46 | R |
| 47 | W |
| 71 | Y |

In another embodiment there is provided a humanised therapeutic antibody or antigen binding fragment thereof which specifically binds to hOSM wherein said antibody or fragment thereof comprises CDRs of SEQ I.D. NO: 40,41, 42,43,44,45 wherein the human heavy chain framework comprises one or more (e.g. all) of the following residues (or a conservative substitute thereof):

| Position | Residue |
|---|---|
| 28 | I |
| 48 | I |
| 44 | K |
| 67 | A |
| 69 | L |
| 71 | V |
| 73 | K | and the human light chain comprises one or more (e.g. all) of the following residues (or conservative substitute thereof);

| Position | Residue |
|---|---|
| 36 | F |
| 38 | K |
| 46 | R |
| 47 | W |
| 71 | Y |

It is well recognised in the art that certain amino acid substitutions are regarded as being "conservative". Amino acids are divided into groups based on common side-chain properties and substitutions within groups that maintain all or substantially all of the binding affinity of the antibody of the invention or antigen binding fragment thereof are regarded as conservative substitutions, see the following table:

| Side chain | Members |
|---|---|
| Hydrophobic | met, ala, val, leu, ile |
| neutral hydrophilic | cys, ser, thr |

-continued

| Side chain | Members |
| --- | --- |
| Acidic | asp, glu |
| Basic | asn, gln, his, lys, arg |
| residues that influence chain orientation | gly, pro |
| aromatic | trp, tyr, phe |

1.3 Bispecific Antibodies

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one preferred approach, the bispecific antibody is composed of a H chain with a first binding specificity in one arm and a H-L chain pair, providing a second binding specificity in the other arm, see WO94/04690. See also Suresh et al Methods in Enzymology 121, 210, 1986.

In one embodiment of the invention there is provided a bispecific therapeutic antibody wherein at least one binding specificity of said antibody is for hOSM, wherein said antibody modulates (i.e. inhibits or blocks) the interaction between Site II of hOSM and gp130, Such antibodies may further comprise a human constant region of the IgG isotype, e.g. IgG1

In one embodiment of the invention there is provided a bispecific therapeutic antibody wherein at least one binding specificity of said antibody is for hOSM, wherein said antibody comprises at least one CDRH3 of SEQ. I.D. NO: 3 or SEQ. I.D. NO:42. Such antibodies may further comprise a human constant region of the IgG isotype, e.g. IgG1.

In one embodiment of the invention there is provided a bispecific therapeutic antibody wherein at least one binding specificity of said antibody is for hOSM, wherein said antibody comprises at least CDRs of SEQ. I.D. NO: 1, 2,3,4,5 and 6 or SEQ. I.D. NO:40, 41,42,43,44 and 45. Such antibodies may further comprise a human constant region of the IgG isotype, e.g. IgG1.

1.4 Antibody Fragments

In certain embodiments of the invention there is provided therapeutic antibody fragments which modulate the interaction between OSM (particularly hOSM) and gp130, Such fragments may be functional antigen binding fragments of intact and/or humanised and/or chimaeric antibodies such as Fab, Fd, Fab', F(ab')$_2$, Fv, ScFv fragments of the antibodies described supra. Traditionally such fragments are produced by the proteolytic digestion of intact antibodies by e.g. papain digestion (see for example, WO 94/29348) but may be produced directly from recombinantly transformed host cells. For the production of ScFv, see Bird et al; (1988) Science, 242, 423-426. In addition, antibody fragments may be produced using a variety of engineering techniques as described below.

Fv fragments appear to have lower interaction energy of their two chains than Fab fragments. To stablise the association of the $V_H$ and $V_L$ domains, they have been linked with peptides (Bird et al, (1988) Science 242, 423-426, Huston et al, PNAS, 85, 5879-5883), disulphide bridges (Glockshuber et al, (1990) Biochemistry, 29, 1362-1367) and "knob in hole" mutations (Zhu et al (1997), Protein Sci., 6, 781-788). ScFv fragments can be produced by methods well known to those skilled in the art see Whitlow et al (1991) Methods companion Methods Enzymol, 2, 97-105 and Huston et al (1993) Int. Rev. Immunol 10, 195-217. ScFv may be produced in bacterial cells such as E. Coli but are more typically produced in eukaryotic cells. One disadvantage of ScFv is the monovalency of the product, which precludes an increased avidity due to polyvalent binding, and their short half-life. Attempts to overcome these problems include bivalent (ScFv')$_2$ produced from ScFV containing an additional C terminal cysteine by chemical coupling (Adams et al (1993) Can. Res 53, 4026-4034 and McCartney et al (1995) Protein Eng. 8, 301-314) or by spontaneous site-specific dimerization of ScFv containing an unpaired C terminal cysteine residue (see Kipriyanov et al (1995) Cell. Biophys 26, 187-204). Alternatively, ScFv can be forced to form multimers by shortening the peptide linker to between 3 to 12 residues to form "diabodies", see Holliger et al PNAS (1993), 90, 6444-6448. Reducing the linker still further can result in ScFV trimers ("triabodies", see Kortt et al (1997) Protein Eng, 10, 423-433) and tetramers ("tetrabodies", see Le Gall et al (1999) FEBS Lett, 453, 164-168). Construction of bivalent ScFV molecules can also be achieved by genetic fusion with protein dimerizing motifs to form "miniantibodies" (see Pack et al (1992) Biochemistry 31, 1579-1584) and "minibodies" (see Hu et al (1996), Cancer Res. 56, 3055-3061). ScFv-Sc-Fv tandems ((ScFV)$_2$) may also be produced by linking two ScFv units by a third peptide linker, see Kurucz et al (1995) J. Immol 154, 4576-4582. Bispecific diabodies can be produced through the noncovalent association of two single chain fusion products consisting of $V_H$ domain from one antibody connected by a short linker to the $V_L$ domain of another antibody, see Kipriyanov et al (1998), Int. J. Can 77, 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al (1999) J. Immunol. Methods 226 179-188. Tetravalent bispecific molecules are available by e.g. fusing a ScFv fragment to the CH3 domain of an IgG molecule or to a Fab fragment through the hinge region see Coloma et al (1997) Nature Biotechnol. 15, 159-163. Alternatively, tetravalent bispecific molecules have been created by the fusion of bispecific single chain diabodies (see Alt et al, (1999) FEBS Lett 454, 90-94. Smaller tetravalent bispecific molecules can also be formed by the dimerization of either ScFv-ScFv tandems with a linker containing a helix-loop-helix motif (DiBi miniantibodies, see Muller et al (1998) FEBS Lett 432, 45-49) or a single chain molecule comprising four antibody variable domains ($V_H$ and $V_L$) in an orientation preventing intramolecular pairing (tandem diabody, see Kipriyanov et al, (1999) J. Mol. Biol. 293, 41-56). Bispecific F(ab')2 fragments can be created by chemical coupling of Fab' fragments or by heterodimerization through leucine zippers (see Shalaby et al, (1992) J. Exp. Med. 175, 217-225 and Kostelny et al (1992), J. Immunol. 148, 1547-1553). Also available are isolated $V_H$ and $V_L$ domains (Domantis plc), see U.S. Pat. No. 6,248,516; U.S. Pat. No. 6,291,158; U.S. Pat. No. 6,172,197.

In one embodiment there is provided a therapeutic antibody fragment (e.g. ScFv, Fab, Fd, Fab', F(ab')$_2$) or an engineered antibody fragment as described supra) that specifically binds to hOSM and modulates (i.e. inhibits or blocks) the interaction between Site II of hOSM and gp130. The therapeutic antibody fragment may comprise a CDRH3 having the sequence of SEQ. I.D. NO: 3 optionally together with CDRs having the sequence set forth in SEQ. I.D. NO: 1,2,4,5 and 6 or a therapeutic antibody fragment comprising a CDRH3 of SEQ. I.D. NO:42 optionally together with CDRs having the sequence set forth in SEQ. I.D. NO: 40,41,43,44 and 45.

1.5 Heteroconjugate Antibodies

Heteroconjugate antibodies also form an embodiment of the present invention. Heteroconjugate antibodies are composed of two covalently joined antibodies formed using any convenient cross-linking methods. See U.S. Pat. No. 4,676,980.

1.6 Other Modifications.

The interaction between the Fc region of an antibody and various Fc receptors (FcγR) is believed to mediate the effector functions of the antibody which include antibody-dependent cellular cytotoxicity (ADCC), fixation of complement, phagocytosis and half-life/clearance of the antibody. Various modifications to the Fc region of antibodies of the invention may be carried out depending on the desired effector property. For example, specific mutations in the Fc region to render an otherwise lytic antibody, non-lytic is detailed in EP 0629 240B1 and EP 0307434B2 or one may incorporate a salvage receptor binding epitope into the antibody to increase serum half life see U.S. Pat. No. 5,739,277. There are five currently recognised human Fcγ receptors, FcγR (I), FcγRIIa, FcγRIIb, FcγRIII a and neonatal FcRn. Shields et al (2001) J. Biol. Chem. 276, 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans R. P (1997) Immunol. Res 16. 29-57 and Ghetie et al (2000) Annu. Rev. Immunol. 18, 739-766). Human IgG1 residues determined to interact directly with human FcRn includes Ile253, Ser254, Lys288, Thr307, Gln311, Asn434 and His435. The present invention therefore concerns antibodies of the invention having any one (or more) of the residue changes detailed above to modify half-life/ clearance and/or effector functions such as ADCC and/or complement lysis. In a further aspect of the present invention there is provided a humanised therapeutic antibody which specifically binds hOSM and modulates the interaction between hOSM and gp130 having alanine (or other disrupting) substitutions at positions 235 (e.g. L235A) and 237 (e.g. G237A). In a further embodiment of the invention there is provided a humanised therapeutic antibody which specifically binds hOSM and comprises a heavy chain of SEQ. I.D. NO:61 and a light chain of SEQ. I.D. NO:12.

Other modifications include glycosylation variants of the antibodies of the invention. Glycosylation of antibodies at conserved positions in their constant regions is known to have a profound effect on antibody function, particularly effector functioning such as those described above, see for example, Boyd et al (1996), Mol. Immunol. 32, 1311-1318. Glycosylation variants of the therapeutic antibodies or antigen binding fragments thereof of the present invention wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al (2001) Biochemistry 40, 8868-8876 the terminal sialyation of a TNFR-IgG immunoadhesin was increased through a process of regalactosylation and/or resialylation using beta-1,4-galactosyltransferace and/or alpha, 2,3 sialyltransferase. Increasing the terminal sialylation is believed to increase the half-life of the immunoglobulin. Antibodies, in common with most glycoproteins, are typically produced in nature as a mixture of glycoforms. This mixture is particularly apparent when antibodies are produced in eukaryotic, particularly mammalian cells. A variety of methods have been developed to manufacture defined glycoforms, see Zhang et al Science (2004), 303, 371, Sears et al., Science, (2001) 291, 2344, Wacker et al (2002) Science, 298 1790, Davis et al (2002) Chem. Rev. 102, 579, Hang et al (2001) Acc. Chem. Res 34, 727. Thus the invention concerns a plurality of therapeutic (typically monoclonal) antibodies (which maybe of the IgG isotype, e.g. IgG1) as described herein comprising a defined number (e.g. 7 or less, for example 5 or less such as two or a single) glycoform(s) of said antibodies or antigen binding fragments thereof.

Further embodiments of the invention include therapeutic antibodies of the invention or antigen binding fragments thereof coupled to a non-proteinaeous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis I. L. et al (2000) Int. J. Pharmaceut. 198:83-95.

Delivery of therapeutic proteins to the brain has been hampered by the presence of the blood brain barrier (BBB). Where it is desired to deliver an antibody of the invention or antibody fragment of the invention across the BBB various strategies have been proposed to enhance such delivery where needed.

In order to obtain required nutrients and factors from the blood, the BBB posseses some specific receptors, which transport compounds from the circulating blood to the brain. Studies have indicated that some compounds like insulin (see Duffy K R et al (1989) Brain Res. 420:32-38), transferin (see Fishman J B et al (1987) J. Neurosci 18:299-304) and insulin like growth factors 1 and 2 (see Pardridge W M (1986) Endocrine Rev. 7:314-330 and Duffy K R et al (1986) Metabolism 37:136-140) traverse the BBB via receptor-mediated transcytosis. Receptors for these molecules thus provide a potential means for antibodies of the invention and/or antibody fragments of the invention to access the brain using so-called "vectored" antibodies (see Pardridge W M (1999) Advanced Drug Delivery Review 36:299-321). For example, an antibody to transferrin receptor has been shown to be dynamically transported into the brain parenchyma (see Friden P M et al (1991) PNAS 88:4771-4775 and Friden P M et al (1993) Science 259:373-377). Thus one potential approach is to produce a bispecific antibody or bispecific fragment such as described supra wherein a first specificity is towards Site II of hOSM (e.g. the first specificity comprises CDRH3 of SEQ. I.D. NO: 3 optionally together with CDRs of SEQ. I.D. NO: 1,2,4,5 and 6 or comprises a CDRH3 of SEQ. I.D. NO:42 optionally together with CDRs of SEQ. I.D. NO:40,41,43,44, 45) and a second specificity towards a transport receptor located at the BBB e.g. a second specificity towards the transferrin transport receptor.

2. Competing Immunoglobulins

The present invention also provides immunoglobulins, antibodies and antigen binding fragments of antibodies and other protein entities such as immunoadhesins which specifically bind hOSM and competitively inhibit, the binding between hOSM and the therapeutic antibody of the invention or antigen binding fragment thereof comprising a heavy chain of SEQ. I.D. NO:11 and a light chain of SEQ. I.D. NO:12. The competing immunoglobulin, antibody and antigen binding fragments of antibodies and other protein entity such as immunoadhesin displays, at equimolar concentrations, at least 25% inhibition, typically 35% or greater, more typically at least 50% inhibition.

Thus in one embodiment of the invention there is provided a method of screening a candidate antibody or antibody fragment to determine whether the candidate antibody or antibody fragment is a competing antibody as herein described which method comprises the steps of;

(a) incubating the candidate antibody or antibody fragment with a therapeutic antibody comprising a heavy chain of SEQ. I.D. NO:11 and a light chain of SEQ. I.D. NO:12 or antigen binding fragment thereof;

(b) determining whether the candidate antibody or antibody fragment thereof of step (a) competitively inhibits the binding between the therapeutic antibody or antigen binding fragment thereof and OSM and in particular hOSM. Typically an ELISA based assay is employed such as the ELISA set forth in the examples. Typically the OSM and/or hOSM are glycosylated. Typically the OSM and/or hOSM has been glycosylated by a mammalian cell such as a recombinantly transformed CHO, NS0 cell or human cell. In other embodiments, OSM and hOSM has been glycosylated by a native cell from which it is derived, i.e. hOSM has been glycosylated by a human cell (for example hOSM may be isolated from the human body).

Thus there is also provided a competing therapeutic antibody or antigen binding fragment thereof which competitively inhibits the binding of a therapeutic antibody or antigen binding fragment thereof which therapeutic antibody or antigen binding fragment thereof comprises CDR having the sequences set forth in SEQ. I.D. NO: 1,2,3,4,5 and 6.

There is also provided a competing therapeutic antibody or antigen binding fragment thereof which competitively inhibits the binding of a therapeutic antibody or antigen binding fragment thereof which therapeutic antibody or antigen binding fragment thereof comprises a heavy chain of SEQ. I.D. NO:11 and a light chain of SEQ. I.D. NO:12.

A competing therapeutic antibody or antigen binding fragment thereof maybe of any of the above antibody structures. For example, the competing therapeutic antibody may be a primate or human intact antibody or a humanised antibody typically of an IgG isotype e.g. IgG1 or IgG4. Competing therapeutic antibody fragments maybe Fab, Fab', Fd, F(ab')$_2$, ScFv and the like. A competing therapeutic antibody may be produced according to the methods disclosed within this present specification.

A typical protocol for the screening method described supra, is set forth in of the examples below.

10D3 is an example of a competing antibody of the invention. See Table A below.

2.1 Other Screening Methods

A further aspect of the present invention is based in part on a finding that the glycosylation of hOSM plays an unexpected role in the binding event between an anti-hOSM antibody and hOSM. The present invention therefore extends to a method of screening an antibody which specifically binds hOSM which method comprises incubating said antibody with glycosylated OSM, particularly hOSM, under conditions permissive for binding and measuring the binding affinity of the antibody. The ELISA protocol detailed below enables such a method. Antibodies (which maybe any of the structures detailed above) maybe selected on the basis of having a binding affinity (Kd) greater than 1 uM, typically greater than 100 nM, more typically greater than 1 nM e.g. 100 pM or greater.

Antibodies may be further selected on the basis of their ability to bind non-glycosylated OSM, e.g. hOSM. Thus antibodies are typically selected on the basis that they are capable of binding glycosylated OSM e.g. hOSM and further also capable of binding non-glycosylated OSM, e.g. hOSM, to the same or similar degree (e.g. have same or similar binding affinity as measured in a Biacore™ assay).

Antibodies selected according to the present method maybe further engineered (e.g. humanised if necessary by for example manipulation of polynucleotides encoding the antibody) and incorporated into a pharmaceutical composition. Antibodies selected by the present method and polynucleotides encoding such antibodies form an embodiment of the present invention. Thus the present invention provides a method of screening an antibody that putatively binds OSM, particularly hOSM (e.g. an antibody which has been raised against OSM/hOSM), which method comprises;

(a) incubating said antibody with glycosylated OSM, particularly glycosylated hOSM under conditions permissive for binding;

(b) measuring the binding affinity of said antibody;

(c) selecting said antibody if said antibody has a binding affinity of greater than 1 uM, typically greater than 100 nM;

(d) providing a polynucleotide encoding said antibody of step (c) and transforming or transfecting a mammalian host cell with a vector comprising said polynucleotide;

(e) culturing said host cell of step (d) under conditions permissive for secretion of said antibody into the culture media;

(f) optionally purifying the culture media of step (e);

(g) incorporating the antibody of step (e) or (f) into a pharmaceutical composition.

Use of an antibody identified by this method in the manufacture of a medicament for the treatment of diseases or disorders detailed below is also provided.

Use of an antibody (e.g. intact, human, humanised, chimaeric) which specifically binds native glycosylated hOSM (particularly binds a Site II epitope of native glycosylated hOSM) and modulates the interaction between said native glycosylated hOSM and gp130 in the manufacture of a medicament for the treatment of a disease or disorder detailed below is also provided. Further provided are antibodies which specifically bind native glycosylated hOSM with the same or similar binding affinity as non-glycosylated hOSM under the same experimental conditions. One embodiment of the invention is antibodies that specifically bind glycosylated OSM, particularly those that bind native glycosylated hOSM. Antibody 15E10 is an example of an antibody that specifically binds glycosylated hOSM.

In some embodiments, the method uses hOSM glycosylated by a mammalian host cell such as CHO or NS0. In other embodiments, the method uses hOSM that has been glycosylated by a human cell e.g. a recombinantly transformed or transfected human host cell or native hOSM that has been isolated from the human body (for example hOSM made by cells found in the synovial fluid of an arthritic (e.g. RA) human patient).

3. Production Methods

Antibodies of the invention maybe produced as a polyclonal population but are more typically produced as a monoclonal population (that is as a substantially homogenous population of identical antibodies directed against a specific antigenic binding site). Antibodies of the present invention may be produced in transgenic organisms such as goats (see Pollock et al (1999), J. Immunol. Methods 231:147-157), chickens (see Morrow K J J (2000) Genet. Eng. News 20:1-55), mice (see Pollock et al ibid) or plants (see Doran P M, (2000) Curr. Opinion Biotechnol. 11, 199-204, Ma J K-C (1998), Nat. Med. 4; 601-606, Baez J et al, BioPharm (2000) 13: 50-54, Stoger E et al; (2000) Plant Mol. Biol. 42:583-590). Antibodies may also be produced by chemical synthesis. However, antibodies of the invention are typically produced using recombinant cell culturing technology well known to those skilled in the art. A polynucleotide encoding the antibody is isolated and inserted into a replicable vector such as a plasmid for further cloning (amplification) or expression. One useful expression system is a glutamate synthetase system (such as sold by Lonza Biologics), particularly where the host cell is CHO or NS0 (see below). Polynucleotide encoding the antibody is readily isolated and sequenced using conventional procedures (e.g. oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotide encoding the light and heavy chains may be inserted into separate vectors and introduced (e.g. by electroporation) into the same host cell or, if desired both the heavy chain and light chain can be inserted into the same vector for transfection into the host cell. Thus according to one embodiment of the present invention there is provided a process of constructing a vector encoding the light and/or heavy chains of a therapeutic antibody or antigen binding fragment thereof of the invention, which method comprises inserting into a vector, a polynucleotide encoding either a light chain and/or heavy chain of a therapeutic antibody of the invention. See Table A below.

In other embodiment of the invention there is provided a polynucleotide encoding a murine $V_H$ domain having the sequence set forth as SEQ. I.D. NO:15 or SEQ. I.D. NO:52

In another embodiment of the invention there is provided polynucleotide encoding a murine $V_L$ domain having the sequence set forth as SEQ. I.D. NO: 16 or SEQ. I.D. NO:53.

In another embodiment there is provided a polynucletotide encoding a humanised $V_H$ domain having the sequence set forth as SEQ. I.D. NO: 17 or SEQ. I.D. NO:54.

In another embodiment there is provided a polynucleotide encoding a humanised $V_L$ chain having the sequence set forth as SEQ. I.D. NO: 18 or SEQ. I.D. NO:55.

In another embodiment there is provided a polynucleotide encoding a humanised heavy chain having the sequence set forth as SEQ. I.D. NO: 19 or SEQ. I.D. NO:56.

In another embodiment there is provided a polynucleotide encoding a humanised light chain having the sequence set forth as SEQ. I.D. NO:20 or SEQ. I.D. NO:57.

It will be immediately apparent to those skilled in the art that due to the redundancy of the genetic code, alternative polynucleotides to those disclosed herein are also available that will encode the polypeptides of the invention.

3.1 Signal Sequences

Antibodies of the present invention maybe produced as a fusion protein with a heterologous signal sequence having a specific cleavage site at the N terminus of the mature protein. The signal sequence should be recognised and processed by the host cell. For prokaryotic host cells, the signal sequence may be an alkaline phosphatase, penicillinase, or heat stable enterotoxin II leaders. For yeast secretion the signal sequences may be a yeast invertase leader, α factor leader or acid phosphatase leaders see e.g. WO90/13646. In mammalian cell systems, viral secretory leaders such as herpes simplex gD signal and a native immunoglobulin signal sequence (such as human Ig heavy chain) are available. Typically the signal sequence is ligated in reading frame to DNA encoding the antibody of the invention.

3.2 Origin of Replication

Origin of replications are well known in the art with pBR322 suitable for most gram-negative bacteria, 2μ plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

3.3 Selection Marker

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media. The selection scheme may involve arresting growth of the host cell. Cells, which have been successfully transformed with the genes encoding the therapeutic antibody of the present invention, survive due to e.g. drug resistance conferred by the selection marker. Another example is the so-called DHFR selection marker wherein transformants are cultured in the presence of methotrexate. CHO cells are a particularly useful cell line for the DHFR selection. Methods of amplifying and selecting host cells using the DHFR system are well established in the art see Kaufman R. J. et al J. Mol. Biol. (1982) 159, 601-621, for review, see Werner R G, Noe W, Kopp K, Schluter M, "Appropriate mammalian expression systems for biopharmaceuticals", Arzneimittel-Forschung.

48(8):870-80, 1998 Aug. A further example is the glutamate synthetase expression system (Lonza Biologics). A suitable selection gene for use in yeast is the trp1 gene; see Stinchcomb et al Nature 282, 38, 1979.

3.4 Promoters

Suitable promoters for expressing antibodies of the invention are operably linked to DNA/polynucleotide encoding the antibody. Promoters for prokaryotic hosts include phoA promoter, Beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter, retrovirus, hepatitis B virus, actin, rous sarcoma virus (RSV) promoter and the early or late Simian virus 40. Of course the choice of promoter is based upon suitable compatibility with the host cell used for expression.

3.5 Enhancer Element

Where appropriate, e.g. for expression in higher eukaroytics, an enhancer element operably linked to the promoter element in a vector may be used. Suitable mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer is typically located on the vector at a site upstream to the promoter.

3.6 Host Cells

Suitable host cells for cloning or expressing vectors encoding antibodies of the invention are prokaroytic, yeast or higher eukaryotic cells. Suitable prokaryotic cells include eubacteria e.g. enterobacteriaceae such as *Escherichia* e.g. *E. Coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B. subtilis* and *B. licheniformis* (see DD 266 710), *Pseudomonas* such as *P. aeruginosa* and *Streptomyces*. Of the yeast host cells, *Saccharomyces cerevisiae, schizosaccharomyces pombe, Kluyveromyces* (e.g. ATCC 16,045; 12,424; 24178; 56,500), *yarrowia* (EP402, 226), *Pichia Pastoris* (EP183, 070, see also Peng et al J. Biotechnol. 108 (2004) 185-192), *Candida, Trichoderma reesia* (EP244, 234), *Penicillin, Tolypocladium* and *Aspergillus* hosts such as *A. nidulans* and *A. niger* are also contemplated.

Although Prokaryotic and yeast host cells are specifically contemplated by the invention, typically however, host cells of the present invention are vertebrate cells. Suitable vertebrate host cells include mammalian cells such as COS-1 (ATCC No. CRL 1650) COS-7 (ATCC CRL 1651), human embryonic kidney line 293, baby hamster kidney cells (BHK) (ATCC CRL.1632), BHK570 (ATCC NO: CRL 10314), 293 (ATCC NO. CRL 1573), Chinese hamster ovary cells CHO (e.g. CHO-K1, ATCC NO: CCL 61, DHFR-CHO cell line such as DG44 (see Urlaub et al, (1986) Somatic Cell Mol. Genet. 12, 555-556)), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Thus in one embodiment of the invention there is provided a stably transformed host cell comprising a vector encoding a heavy chain and/or light chain of the therapeutic antibody or antigen binding fragment thereof as described herein. Typically such host cells comprise a first vector encoding the light chain and a second vector encoding said heavy chain.

Bacterial Fermentation

Bacterial systems are particularly suited for the expression of antibody fragments. Such fragments are localised intracellularly or within the periplasma. Insoluble periplasmic proteins can be extracted and refolded to form active proteins according to methods known to those ski lied in the art, see Sanchez et al (1999) J. Biotechnol. 72, 13-20 and Cupit P M et al (1999) Lett Appl Microbiol, 29, 273-277.

3.7 Cell Culturing Methods

Host cells transformed with vectors encoding the therapeutic antibodies of the invention or antigen binding fragments thereof may be cultured by any method known to those skilled in the art. Host cells may be cultured in spinner flasks, roller bottles or hollow fibre systems but it is preferred for large scale production that stirred tank reactors are used particularly for suspension cultures. Typically the stirred tankers are adapted for aeration using e.g. spargers, baffles or low shear impellers. For bubble columns and airlift reactors direct aeration with air or oxygen bubbles maybe used. Where the host cells are cultured in a serum free culture media it is preferred that the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly vertebrate host cells may utilise a variety of operational modes such as fed-batch, repeated batch processing (see Drapeau et al (1994) cytotechnology 15: 103-109), extended batch process or perfusion culture. Although recombinantly transformed mammalian host cells may be cultured in serum-containing media such media comprising fetal calf serum (FCS), it is preferred that such host cells are cultured in synthetic serum-free media such as disclosed in Keen et al (1995) Cytotechnology 17:153-163, or commercially available media such as ProCHO-CDM or Ultra CHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg K et al (1995) in *Animal Cell technology: Developments towards the 21st century* (Beuvery E. C. et al eds), pp 619-623, Kluwer Academic publishers).

Antibodies of the invention secreted into the media may be recovered and purified from the media using a variety of techniques to provide a degree of purification suitable for the intended use. For example the use of therapeutic antibodies of the invention for the treatment of human patients typically mandates at least 95% purity, more typically 98% or 99% purity compared to the culture media comprising the therapeutic antibodies. In the first instance, cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429, 746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g. nanofiltration using e.g. a DV-20 filter). Following these various steps, a purified (typically monoclonal) preparation comprising at least 75 mg/ml or greater e.g. 100 mg/ml or greater of the antibody of the invention or antigen binding fragment thereof is provided and therefore forms an embodiment of the invention. Suitably such preparations are substantially free of aggregated forms of antibodies of the invention.

4. Pharmaceutical Compositions

Purified preparations of antibodies of the invention (particularly monoclonal preparations) as described supra, may be incorporated into pharmaceutical compositions for use in the treatment of human diseases and disorders such as those outlined above. Typically such compositions further comprise a pharmaceutically acceptable (i.e. inert) carrier as known and called for by acceptable pharmaceutical practice, see e.g. Remingtons Pharmaceutical Sciences, 16th ed, (1980), Mack Publishing Co. Examples of such carriers include sterilised carrier such as saline, Ringers solution or dextrose solution, buffered with suitable buffers to a pH within a range of 5 to 8. Pharmaceutical compositons for injection (e.g. by intravenous, intraperitoneal, intradermal, subcutaneous, intramuscular or intraportal) or continuous infusion are suitably free of visible particulate matter and may comprise between 0.1 ng to 100 mg of antibody, typically between 5 mg and 25 mg of antibody. Methods for the preparation of such pharmaceutical compositions are well known to those skilled in the art. In one embodiment, pharmaceutical compositions comprise between 0.1 ng to 100 mg of therapeutic antibodies of the invention in unit dosage form, optionally together with instructions for use. Pharmaceutical compositions of the invention may be lyophilised (freeze dried) for reconstitution prior to administration according to methods well known or apparent to those skilled in the art. Where embodiments of the invention comprise antibodies of the invention with an IgG1 isotype, a chelator of copper such as citrate (e.g. sodium citrate) or EDTA or histidine may be added to the pharmaceutical composition to reduce the degree of copper-mediated degradation of antibodies of this isotype, see EP0612251.

Effective doses and treatment regimes for administering the antibody of the invention are generally determined empirically and are dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York but will in general be between 1 mg and 1000 mg. In one embodiment, the dosing regime for treating a human patient afflicted with RA is 100 mg or thereabout (i.e. between 50 mg to 200 mg) of antibody of the invention (or antigen binding fragment thereof, administered subcutaneously per week or every two weeks. Compositions of the present invention may also be used in prophylatically.

Depending on the disease or disorder to be treated, pharmaceutical compositions comprising a therapeutically effective amount of the antibody of the invention may be used simultaneously, separately or sequentially with an effective amount of another medicament such as an anti-inflammatory agent for example a NSAID, methotrexate, bucillamine, sodium thiomalate or one or more of an anti-TNF alpha treatment such as Enbrel™ (etanercept), Remicade™ (infliximab), Humira™ (adalimumab) and/or CDP870. Antibodies of the invention maybe used in combination with an effective amount of an anti-TNF-alpha receptor antibody, see Davis M W et al (2000) Ann Rheum Dis 59(Suppl 1): 41-43. In other embodiments, antibodies of the invention maybe used in combination with an effective amount of an agent directed against; IL-1/IL-1R (e.g. Kineret™), CTLA4-1 g, IL-6 (see Choy et al, (2002) Ann. Rheum. Dis 61 (suppl 1): 54), IL-8, IL-15, VEGF, IL-17, IL-18 (see Taylor et al (2001) Curr. Opin. Immunol. 13: 611-616), anti-ICAM and/or anti-CD4 antibodies, agents directed against a member of the MMP family e.g. MMP-1, 2, 3 and/or 13. Antibodies of the invention may also be used in combination with an agent that ablates cells known to be involved in the inflammatory process, e.g. CD20 positive B cells using for example Mabthera™. Other therapies in combination with antibodies of the invention include anti-angiogenic therapies such as antagonists of the integrin $\alpha_v\beta_3$, Kringles 1-5 (see Sumariwalla P et al (2003), Arthritis Res Ther 5:R32-R39.), soluble Flt-1 (see Miotla et al, (2000) Lab. Invest. 80:1195-1205) or an anti-COX-2 agent. Conveniently, a pharmaceutical composition comprising a kit of parts of the antibody of the invention or antigen binding fragment thereof together with such another medicaments optionally together with instructions for use is also contemplated by the present invention. The invention furthermore provides a pharmaceutical composition comprising a therapeutically effective amount of monoclonal therapeutic antibody or antigen binding fragment thereof as described herein for use in the treatment of diseases responsive to modulation of the interaction between Site II OSM and gp130. Also provided is a pharmaceutical composition comprising a therapeutically effective amount of a monoclonal therapeutic antibody which antibody comprises a heavy chain having the sequence set forth in SEQ. I.D. NO: 11 and a light chain having the sequence set forth in SEQ. I.D. NO: 12.

Also provided is a pharmaceutical composition comprising a therapeutically effective amount of a monoclonal therapeutic antibody which antibody comprises a heavy chain having the sequence set forth in SEQ. I.D. NO: 50 and a light chain having the sequence set forth in SEQ. I.D. NO: 51.

4.1 Pharmaceutical Compositions for the Modulation of Both Site II and Site III Interaction.

One aspect of the present invention is based, at least in part, on the unexpected finding that modulating the interaction of both Site II and Site III of the hOSM with their respective interacting partners (i.e. for Site II, gp130, for Site III OSMRβ and/or LIFR, and/or gp130 for binding of a second OSM molecule) displays synergy compared to modulating the interaction of either of these two sites alone.

The present invention therefore provides a method of modulating the interaction between hOSM and gp130 and LIFR and/or OSMRβ which method comprises providing a Site II antagonist capable of modulating (i.e. inhibiting or blocking) the interaction between Site II of hOSM with gp130 and providing a Site III antagonist capable of modulating (i.e. inhibiting or blocking) the interaction between Site III of hOSM and OSMR and/or LIFR, and gp130 (for binding of a second OSM molecule).

In one embodiment there is provided a pharmaceutical composition comprising a first therapeutic antibody which specifically binds hOSM and modulates the interaction between hOSM and gp130 (a Site II antibody, examples of which are provided by this specification) and a second therapeutic antibody which specifically binds hOSM and modulates the interaction between hOSM and OSMR and/or LIFR (a Site III antibody, an example of which is commercially available as MAB295, R&D systems). The second therapeutic antibody may be recognised by its ability to modulate (i.e. inhibit or block) the interaction between hOSM and OSMRβ and/or LIFR in an ELISA based assay or as set forth in the examples, i.e. by its ability to neutralise OSM in the KB assay of the examples and not inhibit the binding of OSM and gp130 in the ELISA assay of the examples.

A Site II antibody maybe recognised by its ability to inhibit OSM binding in the ELISA assay of the examples. Typically both the first and second therapeutic antibodies are monoclonal. It will of course be apparent to those skilled in the art that it is not necessary that the pharmaceutical composition comprises two antagonist entities (e.g. two therapeutic antibody entities) since it is possible to provide e.g. a bispecific antibody that specifically binds hOSM and modulates both the interaction of Site II and Site III with their respective interacting partners.

In another embodiment there is provided a kit-of-parts comprising a first pharmaceutical composition comprising a therapeutic antibody which specifically binds hOSM and modulates the interaction between Site II of hOSM and gp130 and a second pharmaceutical composition comprising a therapeutic antibody which specifically binds hOSM and modulates the interaction between Site III of hOSM and OSMRβ and/or LIFR optionally together with instructions for use.

In another embodiment there is also provided a method of treating a human patient afflicted with a disease or disorder responsive to the modulation of the interaction between hOSM and its interacting partners (e.g. gp130 and OSMRβ and/or LIFR) such as an inflammatory disease or disorder (e.g. arthritic diseases such as rheumatoid arthritis or osteoarthritis) which method comprises administering simultaneously, sequentially or separately a therapeutically effective amount of a first therapeutic antagonist (e.g. antibody) which specifically binds hOSM and modulates the interaction between Site II of hOSM and gp130 and a therapeutically effective amount of a second antagonist (e.g. antibody) which specifically binds hOSM and modulates the interaction between Site III of hOSM and OSMRβ and/or LIFR.

It will of course be apparent to those skilled in the art that at least a first antagonist (such as an antibody) that binds gp130 and modulates (e.g. blocks) the interaction between (a) gp130 and hOSM and also (b) OSMRβ and/or LIFR and hOSM may achieve the same objective as set forth above.

5. Clinical Uses

Antibodies of the invention may be used to treat a variety of diseases or disorders responsive to treatment that modulates the interaction between Site II of hOSM and gp130. Particular mention is made of diseases or disorders involving the production of pathological levels of TNF alpha (i.e. a TNF alpha mediated disease or disorder) and those diseases or disorders characterised by the breakdown or destruction of cartilage, particular articular cartilage. As described in detail supra, antibodies of the invention may be used in the treatment of inflammatory arthropathies such as RA either as a monotherapy or in combination with another treatment for such arthropathy. Antibodies of the invention may be used to treat a clinically established form of the disease in question or to prevent onset in susceptible patients or to slow or halt the progress of the disease towards clinical significance. For the treatment of RA, antibodies of the invention maybe used to prevent relapse once remission from the disease has occurred. Where the patient is afflicted with an intermittent form of the disease, antibodies of the invention may be used to prolong the time interval between acute phases of the disease. Antibodies of the invention may also be used to treat the extraarticular manifestations of RA, e.g Feltys syndrome and/or treat the formation of atherosclerotic plaques. For the treatment of RA, combinations of antibodies of the invention together with medicaments described supra may be used. Other arthritic diseases that may benefit from the administration of an antibody of the invention include Juvenile Onset arthritis, psoriatic arthritis and ankylosing spondylitis.

Osteoarthritis (OA) is a chronic, degenerative disease of unknown origin characterised by the gradual loss of articular cartilage and joint function. It is classified currently into two groups. Primary OA maybe localised or generalised, the latter more commonly found in post-menopausal women, with the development of Heberdens nodes. Secondary OA has an underlying cause such as trauma, obesity, Paget's disease or inflammatory arthritis. Loss of articular cartilage is often accompanied by hypertrophic bone changes with osteophyte formation, subchondral bone thickening and inflammation of the synovial membrane. Of particular concern is the disability afflicted to weight bearing joints such as the knee, hands and hip. OA is an extremely debilitating disease that at its severest requires joint replacement to restore mobility and to stop joint pain. Osteoarthritis of the hip has been divided into hypertrophic and atrophic forms (see Solomon L (1976) J Bone Joint Surg 58, 176) on the basis of a patient's tendency to develop large osteophytes; other joints may respond similarly to the presence of the disease. Hypertrophic OA maybe associated with pyrophosphate crystal deposition and diffuse idiopathic skeletal hyperostosis. Current treatments include the use of nonopioid analgesics such as acetaminophen, and Tramadol, NSAIDS such as a Cox-2 specific inhibitor e.g. celecoxib, rofecoxib, opioid analgesics and glucosamine and chondroitin sulphate. Thus in one embodiment of the invention there is provided a method of treating osteoarthritis (e.g primary or secondary) in a human patient afflicted with such disease, which method comprises administering to said patient a therapeutically effective amount of a therapeutic antibody or fragment thereof of the invention as described herein. The invention also concerns a combination of the therapeutic antibody of the invention together with another treatment particularly one or more of the treatments of OA described above.

Psoriasis is a chronic skin disease with significant morbidity that affects approximately 2% of the Caucasian population. While for many it may be a relatively mild disease, it can have profound effects on those affected. The disability of hospital treated patients with psoriasis has been shown to be similar to that of patients with angina and approaches that of patients with cardiac failure (Finlay et al, (1990); Br. J. Dermatol, 123, 751). The commonest form of psoriasis is chronic plaque disease. This presents as well-defined red scaly plaques typically distributed over the scalp, lower back and extensor aspects of the limbs. Clinical variants include guttate psoriasis, sebopsoriasis and pustular forms of the disease. A minority of patients also develop seronegative inflammatory arthritis. Microscopically, lesional skin shows increased proliferation and abnormal differentiation of keratinocytes, infiltration by activated T-helper lymphocytes and neutrophils and activation of the cutaneous vasculature. These changes correspond to overexpression of growth factors and their receptors, proinflammatory cytokines and angiogenic peptides. However, despite intensive investigation the aetiology and pathogenesis of this disease remains obscure although a central role played by activated T cells has been demonstrated in animal model systems (see Nickoloff et al (1999) Arch. Dermatol. 135, 546-552). Current treatments include topical treatments such as Vitamin D analogues, corticosteroids, dithranol, and retinoids such as Tazarotene gel. Phototherapy includes the use of ultraviolet B or psoralen and ultraviolet A, and excimer lasering. Systemic retinoid treatments include Etretinate and acitretin, isotretinoin, liarozole. Other treatments include methotrexate, hydroxyurea, cyclosporin and calcineurin antagonists, 6-thioguanine, azathioprine, sulfasalazine and fumaric acid esters. More recently, biological treatments such as Ontak™ (Denileukin Diftitox), Zenapax™ (Daclizumab), Basiliximab, anti-CD4 antibodies, Efalizumab, Alefacept™, Siplizumab, IDEC-114 and BMS 188667 (CTLA4lg) have been proposed or demonstrated to be useful in the treatment of this disease. Furthermore, anti-TNF alpha treatments such as Enbrel™ (etanercept), Remicade™ (infliximab), Humira™ (adalimumab) and/or CDP870 may be used in combination with antibodies of the invention for the treatment of psoriasis (including clinical variants thereof).

Evidence for the role of OSM in psoriatic lesions is found in Boifati et al (1998) Arch. Dermatol. Res 290:9, 13. Oncostatin M is secreted spontaneously by short-term organ cultures of lesional psoriatic skin (See Bonifati C et al ibid). Furthermore constitutive activation of STAT3, the major signalling molecule down-stream of the OSM receptor, in mouse keratinocytes results in spontaneous development of psoriatic lesions. (See Sano S et al (2005) Nature Medicine 11:43-49).

Antibodies of the present invention may therefore be used in the treatment of psoriasis (chronic plaque, guttate, sebopsoriasis, pustular, seronegative inflammatory arthritis associated psoriasis), atopic dermatitis/eczema, acne, ichythosis, pemphigus, viral warts either as a monotherapy or in combination with these treatments described supra.

Systemic lupus erythematosus (SLE) is a systemic autoimmune disease characterised by production of auto-antibodies, immune complex formation and immunologically mediated tissue damage (Reviewed in Rheumatology (2003). Eds Hochberg, Silman, Smolen, Weinblatt and Weisman. Pub. Mosby. 1291-1430). Pathologic manifestations include fibrinoid necrosis, hemotoxylin bodies, vascular injury, and disruption of the dermal-epidermal junction of skin, inflammatory arthritis and glomerulonephritis. SLE can present at any age including in neonates. It is is one of the most common disorders affecting women of child-bearing age, is significantly more common in women than men and affects people of African origin significantly more frequently than Caucasians. Its incidence has been estimated between 1.8 and 7.6 cases per 100,000 person-years in the US. SLE is associated with increased mortality, principally from infection, and renal and CNS complications. Treatment of lupus and its complications is determined by individual patient's needs. Non-steroidal anti-inflammatory drugs are an important first-line therapy for musculo-skeletal symptoms, constitutional signs and mild serositis. Anti-malarials (e.g hydroxychloquine, chloroquine and quinacrine) are used to treat musculo-skeletal symptoms and constitutional signs that are refractory to nos-steroidals and low-dose steroids. Most clinical manifestations of SLE respond to treatment with steroids but the side effects of these drugs may limit both dose and duration of treatment. Immunosuppressive drugs, notably Azathioprine, may be used for more severe disease. Recently, treatment with the B cell depleting antibody Rituxan has shown promising results in SLE (Reviewed in Looney R J et al (2005) Curr Dir Autoimmune 8:193-205). Oncostatin M has been found at elevated levels in serum for SLE patients and levels shown to correlate with disease activity (See Robak E et al (1997) Eur Cytokine Netw 8: 281-286). Thus the invention concerns use of antibodies of the invention in the treatment (either as a monotherapy or in combination with one or more of the current SLE treatments detailed above) of SLE.

System is sclerosis (SS) which includes variants of scleroderma and Raynauds phenomenon is a generalised disorder of the skin and internal organs. It is characterised by extracellular matrix accumulation in the skin and viscera. Oncostatin M can stimulate excessive extracellular matrix accumulation (See Bamber B et al (1997) J Mol Med Abstract Vol 76: 61-69). Oncostatin M is produced spontaneously from cultured mononuclear cells from patients with systemic sclerosis (See Hasegawa M et al (1999) Rheumatology (Oxford) 38: 612-617) and is found in bronchoalveolar lavage fluid from pulmonary fibrosis in scleroderma (Reviewed in Atama SP and White B (2003) Cytokine growth Factor Rev 14: 537-550). Thus the invention concerns the use of antibodies of the invention in the treatment of SS and variants thereof either as a monotherapy or in combination with another medicament.

OSM has been detected in the bronchoaveolar lavage fluid of patients during acute lung injury, particularly in cases of pneumonia (Tamura S et al (2002) Develop Dyman 225:327-331). Neutrophils appear to be the cellular source of OSM in these patients, and OSM concentrations in the BAL fluid correlate with PMN numbers. Since neutrophils are a source of OSM, and upon activation secrete OSM, it is probable that OSM will be present in the lungs of any patient where neutrophils are a significant component of airway inflammation, including COPD and severe asthma. In addition, OSM is also expressed by (mouse) tissue eosinophils and could be a significant source of OSM during inflammation see Tamura ibid).

Overexpression of OSM in mouse airways using an adenoviral vector induced profound eosinophilic inflammation and matrix deposition (see Langdon C et al (2003) J. Immunol. 170:548-555 and also TIMP-1 expression (see Kerr C et al (1999) J. Interfer. Cytokine Res., 19:1195-1205. Exposure of mouse lung fibroblasts to OSM stimulated release of eotaxin, a potent eosinophil chemoattractant. Moreover, OSM stimulates the proliferation, induces collagen production and prevents apoptosis of human lung fibroblasts (see Scaffidi, A. K. et al (2002) Brit. J. Pharamcol 136:793-801). Although the mechanisms behind these observations are unknown, matrix deposition could, in part, be the result of a strong, specific upregulation of $\alpha_1$ proteinase inhibitor synthesis (see Cichy, J. et al (1998) Biochem. J 329:335-339). OSM has also been found to promote fibroblast dependent mast cell proliferation and a marked increase in histamine content (see Gyotoku E et al (2001) Arch. Dermatol. Res 293:508-514). Direct instillation of OSM in isolated rat lungs induced rapid and sustained IL-6 secretion (see Li, H. L. (2002) J. Drug Targ 10:55-62). Thus the present invention concerns the use of antibodies of the invention (either as a monotherapy or in combination with another medicament) in the treatment of inflammatory lung diseases such as asthma and COPD (chronic obstructive pulmonary disorder).

OSM has been detected in the brains of multiple sclerosis (MS) patients, where it localises to microglia, astrocytes and infiltrating leukocytes (see Ruprecht K et al Journal of Neuropathology & Experimental Neurology. 60(11): 1087-98, 2001 November). OSM induces IL-6 and MCP-1 secretion from cerebral endothelial cells, and addition of TNFα with OSM causes a synergistic response. OSM also induces ICAM1 expression on cerebral microvascular endothelial cells, which could enhance leukocyte infiltration into brain tissue (Ruprecht K et al ibid). In addition to promoting inflammation in the brain, OSM may directly contribute to neuron loss. HIV patient's monocyte supernatants cause profound inhibition of neuroblast growth and also neuronal cell death, and the mediator of these effects was shown to be Oncostatin M. Since many HIV patients suffer from brain atrophy caused by neuronal cell loss, OSM may be one mediator of this pathology. Clearly, OSM could also play a role in other CNS diseases where neuronal loss occurs. Interestingly in Alzheimer's disease (AD), $α_1$ antichymotrypsin (ACT) is one of the amyloid associated proteins and its expression is dramatically increased in disease areas, perhaps facilitating deposition of abnormal proteins in amyloid plaques and neutrofibrillary tangles. OSM, which is known to be secreted by both infiltrating activated T cells and monocytes, and microglia, is a potent inducer of ACT, and could thereby contribute to the AD pathology (see Kordula T et al (1998) J. Biol. Chem. 273:4112-4118 and Kordula T Journal of Neuroscience. 20(20): 7510-6, 2000). Work by Tamura et al suggests that OSM may be involved in the development and maintenance of neuropathic pain (see Tamura S. et al (2003) Eur. J. Neurosci. 17:2287-2298). Their studies revealed a subset of nociceptive sensory neurons that express the OSMβ receptor. All the OSMβR+ve neurons also expressed VR1 and P2X3 receptors, which have been shown to be crucial for development of both neuropathic and inflammatory pain (see Jarvis M. F. et al (2002) PNAS 99:179-184 and Walker K. M et al (2003) J. Pharmacol. Exp. Ther 304, 56-62). Furthermore OSM−/− mice have reduced noxious responses to chemical, thermal, visceral and mechanical pain, correlating with a reduction of $VR1^{+ve}$ $P2X3^{+ve}$ small neurons (see Morikawa, Y. et al (2004): J Neurosci 24, 1941-1947).

Thus the present invention also concerns the use (either as a monotherapy or in combination with another medicament) of antibodies of the invention in the treatment of central nervous system diseases or disorders such as described supra such as multiple sclerosis (MS), Alzheimer's disease (AD) and other dementias and furthermore concerns the use in the treatment of pain, particularly neuropathic and/or inflammatory pain.

OSM is found in tissue macrophages in atherosclerotic lesions (see Modur V. et al J. Clin Invest. 100, 158-168) and as an angiogenic factor may promote the neovascularisation characteristic of atherosclerotic plaques that is thought to contribute to vessel wall fragility. As well as the angiogenic response, OSM causes induction of both IL-6 secretion in endothelial cells, where its effects are additive or synergistic with IL-1 and TNFα respectively, and COX-2 expression (see Brown J. T et al (1991) J. Immunol 147: 2175-2180). Endothelial cell induction of COX2 is necessary for the angiogenic properties of OSM (see Brown J. T et al, ibid). However, OSM also induces expression other angiogenic factors in endothelial cells; VEGF (Vasse, M et al (1999) Arterioscler Thromb Vasc Biol. 19:1835-1842) and bFGF (Wijelah E. S. et al (1997) J. Cell Sci 110:871-879) Interestingly, human endothelial cells have about 10-20 fold greater OSM receptor density than other cells (see Modur V. et al ibid).

In addition to effects on endothelium, OSM also induces IL-6 and COX-2 expression in vascular smooth muscle cells (VSMC) as well as causing striking changes in cell morphology (Bernard C. et al (1999) Circ. Res. 85:1124-1131). Calcium deposits are usually found in advanced atherosclerotic lesions where macrophages are the predominant inflammatory cell. Macrophages are a major source of OSM and interestingly, this cytokine can induce bone-type alkaline phosphatase and calcium deposition in VSMC cultures (Shioi A. et al (2002) Circ. Res. 91:9-16). OSM also respectively induces and depresses tissue factor (TF) and TF pathway inhibitor (TFPI) secretion from VSMCs, resulting in a potent procoagulant activity in VSMC culture supernatants (Mirshahi F. et al (2002) Blood Coag. Fibrinol. 13:449-455). Furthermore, OSM affects von-Willebrand factor, tissue-type plasminogen activator and PAI-1 secretion from endothelial cells in a way that suggests that "OSM could play a key role in the development of atherosclerotic lesions" (Portau J et al (1998) Blood Coag. Fibrinol. 9, 609-615).

Plasma levels of fibrinogen are an important vascular risk factor and OSM is a potent inducer of fibrinogen secretion in studies with a hepatoma cell line (Vasse. M et al (1996) Haemostasis 26, Suppl 4, 331-339). However, at high concentrations (50 ng/ml) OSM also increased human LDL receptor expression (Liu et al (2003) Aterio. Thromb. Vasc. Biol. 23: 90-96). Finally, OSM promotes cholesterol esterification in J774 monocyte-macrophages, and may therefore contribute to this process during Foam cell development in atherosclerotic lesions (Maziere C et al (1996) Biochem. Biophys Acta 1300, 30-34).

Thus the present invention concerns the use of antibodies of the invention in the treatment of diseases or disorders of the cardiovascular system. Also contemplated is use of anti bodies of the invention in the treatment of atherosclerosis and diseases of endothelial cell origin. Further contemplated is the use of antibodies of the invention in treating patients afflicted with HIV, particularly to treat conditions resulting from infection with the virus such as Karposi sarcoma.

Antibodies of the invention may also be used in diseases of cell cycle regulation e.g. cancer (such as prostate cancer), myeloma.

Although the present invention has been described principally in relation to the treatment of human diseases or disorders, the present invention may also have applications in the treatment of similar diseases or disorders in non-human mammals.

TABLE A

| Protein or Polynucleotide (PN) | Antibody 15E10 | Antibody 10D3 |
|---|---|---|
| CDRH1 | SEQ. I.D. NO: 1 | SEQ. I.D. NO: 40 |
| CDRH2 | SEQ. I.D. NO: 2 | SEQ. I.D. NO: 41 |
| CDRH3 | SEQ. I.D. NO: 3 | SEQ. I.D. NO: 42 |
| CDRL1 | SEQ. I.D. NO: 4 | SEQ. I.D. NO: 43 |
| CDRL2 | SEQ. I.D. NO: 5 | SEQ. I.D. NO: 44 |
| CDRL3 | SEQ. I.D. NO: 6 | SEQ. I.D. NO: 45 |
| $V_H$ domain (murine) | SEQ. I.D. NO: 7 | SEQ. I.D. NO: 46 |
| $V_L$ domain (murine) | SEQ. I.D. NO: 8 | SEQ. I.D. NO: 47 |
| $V_H$ domain (humanised, B3) | SEQ. I.D. NO: 9 | SEQ. I.D. NO: 48 |
| $V_L$ domain (humanised, L2) | SEQ. I.D. NO: 10 | SEQ. I.D. NO: 49 |
| Heavy chain (humanised) | SEQ. I.D. NO: 11 | SEQ. I.D. NO: 50 |

TABLE A-continued

| Protein or Polynucleotide (PN) | Antibody 15E10 | Antibody 10D3 |
|---|---|---|
| Light chain (humanised) | SEQ. I.D. NO: 12 | SEQ. I.D. NO: 51 |
| $V_H$ domain (murine, PN) | SEQ. I.D. NO: 15 | SEQ. I.D. NO: 52 |
| $V_L$ domain (murine, PN) | SEQ. I.D. NO: 16 | SEQ. I.D. NO: 53 |
| $V_H$ domain (humanised, PN, B3) | SEQ. I.D. NO: 17 | SEQ. I.D. NO: 54 |
| $V_L$ domain (humanised, PN, L2) | SEQ. I.D. NO: 18 | SEQ. I.D. NO: 55 |
| Heavy chain (humanised, PN) | SEQ. I.D. NO: 19 | SEQ. I.D. NO: 56 |
| Light chain (humanised, PN) | SEQ. I.D. NO: 20 | SEQ. I.D. NO: 57 |
| $V_H$ domain (B4, humanised) | SEQ. I.D. NO: 21 | N/A |
| Heavy chain (humanised, $F_C$ mutated | SEQ. I.D. NO: 61 | N/A |
| Heavy chain (humanised, $F_C$ mutated, PN) | SEQ. I.D. NO: 62 | N/A |

The present invention is now described by way of example only. The appended claims may include a generalisation of one of more of the following examples.

EXEMPLIFICATION

Examples 1 to 6 concern the production and engineering of antibody 15E10. Example 7 concerns the production and engineering of antibody 10D3.

1. Generation of Monoclonal Antibodies

Monoclonal antibodies are produced by hybridoma cells generally in accordance with the method set forth in E Harlow and D Lane, Antibodies a Laboratory Manual, Cold Spring Harbor Laboratory, 1988. The result of the fusion of mouse myeloma cells with B-lymphocytes from mice immunised with the target antigen. The hybridoma cell is immortalised by the myeloma fusion partner while the capacity to produce antibodies is provided by the B lymphocyte.

Four SJL mice were immunised by intraperitoneal injection with glycosylated human OSM (hOSM) produced in CHO cells suspended in RIBI adjuvant (Sigma). The mice were boosted with hOSM only after 2 weeks then with hOSM neutralised with anti-site III monoclonal antibody (OM4/11.17; OSM:Mab 1:1.5 wt:wt) to drive the immune response towards Site II after a further 2 weeks then again with the OSM-MAb complex after another 2.5 weeks and finally with OSM only after 5 weeks. Three months after initial immunisation, spleens were removed and B lymphocytes fused with mouse myeloma cells derived from P3X cells using PEG1500 (Boehringer) to generate hybridomas. Individual hybridoma cell lines were cloned by limiting dilution (E Harlow and D Lane). Wells containing single colonies were identified microscopically and supernatants tested for activity. Cells from the most active clones were expanded for cryopreservation, antibody production etc. Initial OSM antibody selection was on the basis of specificity and potency in neutralising human glycosylated OSM assessed in the gp130 inhibition ELISA and the KB cell assay, (see below) the latter providing a check of OSM specificity. After identification of antibodies of sufficient potency and correct specificity, further selection criteria were applied:

1/ cross-reactivity against cynomolgus monkey OSM

2/ maintenance of activity against human OSM in the presence of pooled human AB serum 3/ maintenance of activity against a human neutrophil OSM library and against RA synovial fluid cell-derived OSM 1920 hybridomas were screened in the gp130 inhibition ELISA. 43 gave more than 50% inhibition and limited dose response experiments were done on 15 from which 6 were selected for further study. These were subcloned and master clones were selected.

Two antibodies, clone 15E10 and clone 10D3 (see example 7) were selected on the basis of potency. 15E10 murine antibody was consistently more potent in the gp130 inhibition ELISA but had potency similar to 10D3 in the KB cell assay when human OSM was the target antigen. However, 15E10 murine antibody was much more potent than 10D3 against cynomolgus monkey OSM in both assays.

2. Cloning of Variable Regions of Clone 15E10

Total RNA was extracted from clone 15E10 hybridoma cells and the cDNA of the heavy and light variable domains was produced by reverse transcription using primers specific for the murine leader sequence and the antibody constant regions according to the pre-determined isotype (IgG2a/κ). The cDNA of the variable heavy and light domains was then cloned into vector pCR2.1 for sequencing.

2.1 RNA Extraction

Total RNA was extracted from pellets of $10^6$ cells of hybridoma clone 15E10 using the SV Total RNA Isolation System from Promega according to manufacturer's instructions.

2.2 Reverse Transcription

RNA was reverse transcribed to produce cDNA of the variable heavy and light domains using primers specific for the murine leader sequences and murine IgG=2a/κ constant regions. The mixture of primers used is set forth in Jones S T and Bendig M M Bio/technology 9:88-89 (1991)

Pools of murine $V_H$ and $V_L$ leader sequence forward primers were prepared at 50 μM. Solutions of the murine γ2a and κ constant region reverse primers were also prepared at 50 μM.

2.3 Reverse Transcription PCR(RT-PCR)

Reverse transcription of the RNA encoding the variable heavy and light regions was carried out in duplicates using the Access RT-PCR System from Promega according to manufacturer's instructions. $V_H$ and $V_L$ forward and reverse primers were as described above.

3. Cloning of PCR Product of 2.3

3.1 Gel Purification

The products of RT-PCR ($2 \times V_H$ and $2 \times V_L$) were loaded in gel loading solution on a preparative 1% agarose gel containing 0.01% ethidium bromide and run in TAE buffer at 100V for 1 hour and the V region bands excised. A 100 bp DNA ladder was also run on the gel to allow identification of the $V_H$ and $V_L$ bands.

The DNA fragments were extracted and purified from the gel using the QIAquick™ Gel extraction kit from Qiagen according to manufacturer's instructions.

3.2 Ligation

The purified RT-PCR fragments ($2 \times V_H$ and $2 \times V_L$) were cloned into the pCR2.1 vector using the TA cloning kit from Invitrogen according to manufacturer's instructions.

3.3 Transformation

Ligated plasmids were transformed into TOP10F' cells according to TA cloning kit instructions. 50 µl and 200 µl of transformed cells were spread on L-agar plates containing 100 µg/ml ampicillin and coated with 8 µl of 500 mM IPTG solution and 16 µl of 50 mg/ml X-Gal solution in DMF. Plates were incubated overnight at 37° C.

3.4 Sequencing 5 white colonies were cultured overnight at 37° C. in 5 ml LB medium supplemented with 100 µg/ml ampicillin.

pCR2.1 plasmids containing 15E10 $V_H$ and $V_L$ domains were extracted and purified using the Qiagen QIAprep Spin Miniprep kit according to manufacturer's instructions.

The $V_H$ and $V_L$ domains were sequenced using primers T7, M13 for and M13 rev.

15E10 $V_H$ domain amino acid sequence (consensus of 10 clones from 2 RT-PCR reactions): SEQ. I.D. NO:7

15E10 $V_L$ domain amino acid sequence (consensus of 10 clones from 2 RT-PCR reactions): SEQ. I.D. NO:8

4. Chimaeric Antibody

A chimaeric antibody consisting of parent murine V regions of 3.4 grafted onto human IgG1/k wild type C regions was designed to confirm the cloning of the correct murine V regions and also to be used as a reference when testing humanised constructs. The chimaeric antibody was expressed in CHO cells, purified and tested for affinity to OSM site II in the gp130 inhibition ELISA and KB cell assay (see below).

The cloned murine V regions were amplified by PCR to introduce restriction sites required for cloning into mammalian expression vectors Rld and Rln. Hind III and Spe I sites were designed to frame the $V_H$ domain and allow cloning into a modified Rld vector containing the human γ1 wild type C region. Hind III and BsiW I sites were designed to frame the $V_L$ domain and allow cloning into a modified Rln vector containing the human κ C region.

4.1 PCR Amplification

```
V_H forward primer:
                                       (SEQ. I.D. NO:22)
5'-GAT GAA GCT TGC CAC CAT GGC TGT CCT AGG GCT ACT
C-3'
```

The Hind III restriction site is underlined and Kozak sequence in bold.

```
V_H reverse primer:
                                       (SEQ. I.D. NO:23)
5'-GAT GGA CTA GTG TCC CTG TGC CCC AGA C-3'
```

The Spe I restriction site is underlined.

```
V_L forward primer:
                                       (SEQ. I.D. NO:24)
5'-GAT GAA GCT TGC CAC CAT GGA TTT TCA GGT GCA GAT
T-3'
```

The Hind III restriction site is underlined and Kozak sequence in bold.

```
V_L reverse primer:
                                       (SEQ. I.D. NO:25)
5'-GAT GCG TAC GTT TGA TTT CCA ACT TTG TCC C-3'
```

The BsiW I restriction site is underlined

| PCR reaction: | water | 66 µl |
|---|---|---|
| | 10× PCR buffer | 10 µl |
| | dNTP (2 mM) | 10 µl |
| | primer 1 (5 µM) | 4 µl |
| | primer 2 (5 µM) | 4 µl |
| | AmpliTaq polymerase | 2 µl |
| | purified plasmid | 4 µl |
| | total vol | 100 µl |

Primer 1: $V_H$ or $V_L$ forward primer

Primer 2: $V_H$ or $V_L$ reverse primer

Purified plasmid: pCR2.1 $V_H$ or $V_L$ plasmid purified by Qiagen Minipreps (diluted 200×)

| PCR cycle: | 1- 95° C. for 4 min |
|---|---|
| | 2- 95° C. for 1 min |
| | 3- 55° C. for 1 min |
| | 4- 72° C. for 1 min |
| | 5- 72° C. for 7 min |
| | steps 2 to 4: were repeated 30 times |

4.2 Cloning into Mammalian Expression Vectors

The PCR products were purified using the MinElute PCR Purification kit from Qiagen according to manufacturer's instructions.

4.2.1 Restriction Digests

The $V_H$ PCR product and Rld hCγ1 wt mammalian expression vector were digested Hind III-Spe 1:

| 10× buffer (NEBuffer2) | 5 µl |
|---|---|
| BSA 100× (NEB) | 0.5 µl |
| DNA | 5 µl |
| Hind III (Promega) | 2 µl |
| Spe I (NEB) | 2 µl |
| water | 35.5 µl |
| total vol | 50 µl |

DNA: purified $V_H$ PCR product or Rld hCγ1wt vector (at 0.25 mg/ml) Incubated at 2 h at 37° C.

The $V_L$ PCR product and Rln hCκ mammalian expression vector were digested Hind III-BsiW I:

| 10× buffer (NEBuffer2) | 5 µl |
|---|---|
| DNA | 5 µl |
| Hind III (Promega) | 2 µl |
| water | 38 µl |
| total vol | 50 µl |

DNA: purified $V_L$ PCR product or Rln hCκ vector (at 0.25 mg/ml) Incubated at 2 h at 37° C.

2 µl of BsiW I (NEB) was added and incubated 2 h at 55° C.

4.2.2 Gel Purification

The products of restriction digests were loaded in gel loading solution on a preparative 1% agarose gel containing 0.01% ethidium bromide and run in TAE buffer at 100 V for 1 hour and the Rld and Rln vector as well as $V_H$ and $V_L$ PCR fragment bands were excised. A 100 bp DNA ladder was also run on the gel to allow identification of the $V_H$, $V_L$ and vector bands. The DNA was extracted and purified from the gel using the QIAquick Gel extraction kit from Qiagen according to manufacturer's instructions.

4.2.3 Ligation

The $V_H$ PCR fragment Hind III-Spe I digested was ligated into the Rld hCγ1 wt vector Hind III-Spe I digested.

The $V_L$ PCR fragment Hind III-BsiW I digested was ligated into the Rln hCκ vector Hind III-BsiW I digested.

The ligation was carried out using the LigaFast Rapid DNA Ligation System from Promega according to manufacturer's instructions providing:

| | |
|---|---|
| $V_H$: | vector: Rld hCγ1wt Hind III-Spe I digested |
| | insert: $V_H$ PCR fragmem Hind III-Spe I digested |
| $V_L$: | vector: Rln hCκ Hind III-BsiW I digested |
| | insert: $V_L$ PCR fragment Hind III-BsiW I digested |

4.2.4 Transformation

Ligated products were transformed into DH5α competent cells:

200 µl DH5α vials were thawed on ice.

50 µl aliquots were prepared in transformation tubes.

2 µl of ligation mixture was added and mixed gently with a pipette tip followed by incubation for 30 min on ice.

The mixture was incubated for 45 sec at 42° C. without shaking.

This was then transferred to ice for 2 min.

450 µl SOC medium was added and the tubes incubated for 1 h at 37° C. on shaker incubator.

100 µl of culture was spread on L-agar plates supplemented with 100 µg/ml ampicillin and incubated overnight at 37° C.

4.2.5 Sequencing $V_H$ and $V_L$ clones were cultured overnight at 37° C. in 5 ml LB medium supplemented with 100 µg/ml ampicillin.

Rld and Rln plasmids containing $V_H$ and $V_L$ domains respectively were extracted and purified using the QIAprep Spin Miniprep kit from Qiagen according to manufacturer's instructions.

The $V_H$ region was sequenced using forward primers in the Rld vector and signal sequence and reverse primer in the human $Cγ_1$ region.

The $V_L$ region was sequenced using forward primers in the Rln vector and signal sequence and reverse primer in the human Cκ region.

Clones with the correct $V_H$ and $V_L$ sequences were identified and plasmids prepared for expression in CHO cells.

4.3 Chimaeric Antibody Expression in CHO Cells

Rld and Rln plasmids containing 15E10 $V_H$ and $V_L$ domains respectively were transiently co-transfected into CHO cells and expressed. The chimaeric antibody produced was purified from cell culture supernatant by affinity chromatography on rProtein A Sepharose and its affinity for OSM was evaluated in the gp130 inhibition ELISA and KB cell assay (see below).

4.3.1 Plasmid Purification

DH5α cells containing Rld-15E10$V_H$ and Rln-15E10$V_L$ plasmids were cultured in 5 ml of LB media supplemented with 100 µg/ml ampicillin for 8 h at 37° C. in a shaker incubator.

200 ml of LB media supplemented with 100 µg/ml ampicillin was inoculated with 1 ml of day culture and incubated overnight at 37° C. in a shaker incubator.

The plasmids were extracted and purified using the QIAfilter Plasmid Maxi kit from Qiagen according to manufacturer's instructions. The ethanol pellet was resuspended in 200 µl TE buffer and plasmid concentration was measured by absorbance at 260 nm after 100-fold dilution of stock solution.

4.3.2 Transfection

CHO cells were cultured to confluence in Dulbecco's MEM with Glutamax-1 (DMEM) media supplemented with Ultra Low Fetal Bovine Serum and 1% Penicillin-Streptomycin in 4×175 cm² BD Falcon tissue culture flasks at 37° C.

For each flask, in a 50 ml Falcon tube, the following were added and mixed:

8 ml Optimem 1 with Glutamax-1

20 µg Rld-15E10$V_H$ purified plasmid

20 µg Rln-15E10$V_L$ purified plasmid

240 µl TransFast Transfection Reagent under vortex

The mixture was incubated for 10-15 min at room temperature (RT). DMEM media was removed from flask then the mixture was vortexed and added to flask.

The mixture was incubated at 37° C. for 1 h.

32 ml Optimem was added to the flask and incubated at 37° C. for 48-72 h.

4.3.3 Purification of Chimaeric Antibody

Media from all 175 cm² flasks were pooled and centrifuged at 1500 rpm for 3 min on an MSE Mistral 2000 and supernatant passed through a 500 mL Filter System 0.22 µm CA.

The antibody was purified from clarified supernatant on an Amersham Biosciences Akta Explorer using Unicorn software.

The column used was a 1 ml HiTrap rprotein A Sepharose FF.

The flow rate was 1 ml/min.

The column was equilibrated with 10 CV of Dulbecco's PBS then loaded with clarified supernatant through pump A.

The column was washed with 20 CV of Dulbecco's PBS, pump A was washed to waste and a further 10 CV of Dulbecco's PBS was passed through the column to ensure complete clearance of supernatant.

The antibody was eluted with 10 CV of ImmunoPure IgG Elution Buffer (Pierce) and collected in 1 ml fractions containing 100 µl of 1M Trizma-HCl pH8.0 neutralisation buffer.

The column was re-equilibrated with 5 CV of Dulbecco's PBS.

Antibody in eluate fractions was quantified by reading the absorbance at 280 nm against a blank solution containing 10 volumes of ImmunoPure IgG Elution Buffer+1 volume of 1M Trizma-HCl pH8.0 and fractions with sufficient amounts of pure antibody were pooled and stored in 100 µl aliquots at −20° C.

4.4 Analysis of Chimaeric Antibody

Purified 15E10 and 10D3 (see below) chimaeric antibodies was analysed in the gp130 inhibition ELISA and KB cell assay for their potency in neutralising both human and cynomolgus OSM (hOSM and cOSM). Protocols for the gp130 inhibition ELISA and KB cell assay are set forth below.

TABLE 1

IC50 (µg/ml) values for 15E10 and
10D3 murine and chimeric antibodies

|  | gp130 ELISA | KB cell assay |
|---|---|---|
| 15E10 murine | 0.059 | 0.195 |
| 15E10 chimaeric | 0.036 | 0.110 |
| 10D3 murine | 0.107 | 0.114 |
| 10D3 chimaeric | 0.057 | 0.107 |

Figure 2:
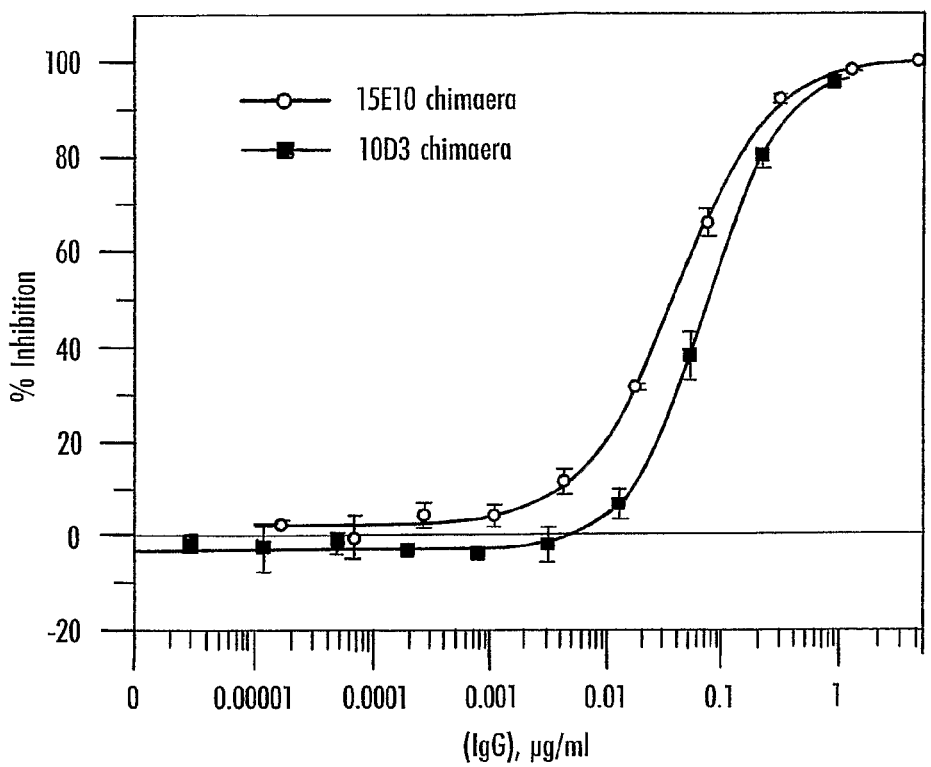
FIG. 2 illustrates the gp130 inhibition ELISA using hOSM (upper panel) and cOSM (lower panel) following the protocol of set forth below of the examples using the 15E10 and 10D3 chimaeric antibodies. See the description below for further details.
Figure 2:
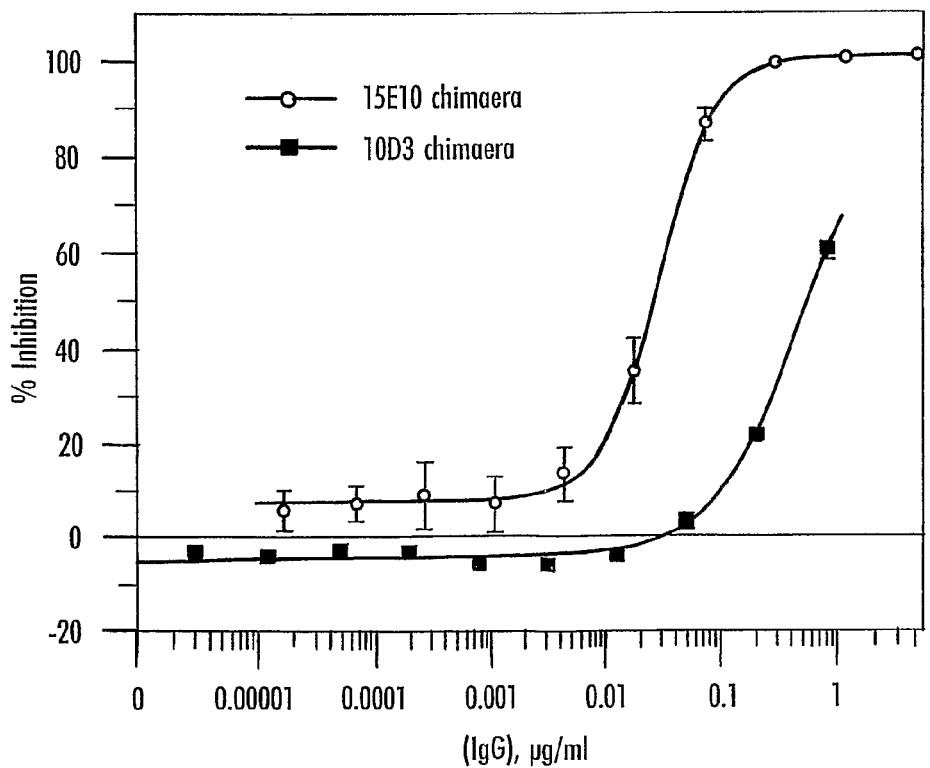
Figure 3:
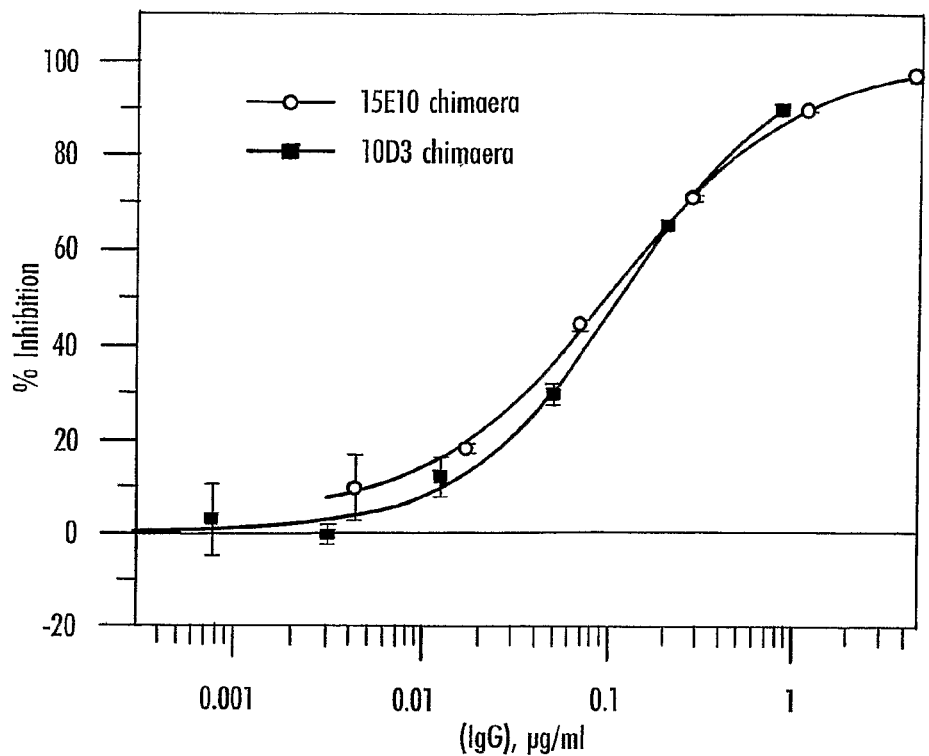
FIG. 3 illustrates the KB cell assay using hOSM (upper panel) and cOSM (lower panel) following the protocol of the examples using the 15E10 and 10D3 chimaera antibodies of the examples.
Figure 3:
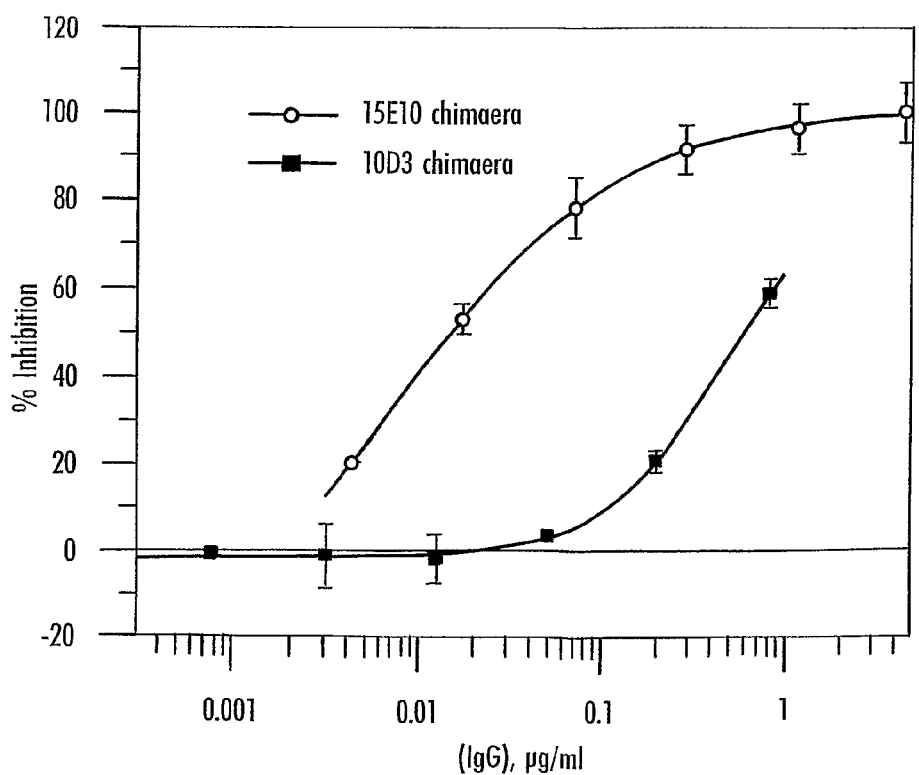

Both 15E10 and 10D3 Chimaeric antibodies neutralise hOSM and cOSM in the gp130 inhibition ELISA (FIG. 2) and KB cell assay (FIG. 3). Chimaeric 15E10 has a higher affinity for cynomolgus OSM than chimaeric 10D3 as observed with the parent murine antibody. Both chimaeric antibodies have curve profiles and IC50 values similar to the parent murine antibodies (Table 1). The amino acid sequence and a cDNA sequence for cynomolgus OSM (cOSM) is set forth as SEQ. I.D. NO:63 and 64 respectively;

SEQ. I.D. NO:63:
MGVPLTRRTLLSLILALLFPSMASMAAMGSCSKEYRMLLGQLQKQTDLMQ
DTSRLLDPYIRIQGLDIPKLREHCRESPGAFPSEETLRGLGRRGFLQTLN
ATLGCVLHRLDLEQHLPKAQDLERSGLNIEDLEKLQMARPNVLGLRNNVY
CMAQLLDNSDMTEPTKAGRGTPQPPTPTPTSDVFQRKLEGCSFLRGYHRF
MHSVGRIFSKWGESPNRSRRHSPHQALRKGVRRTRPSRKGNRLMPRGQLP
R

SEQ. I.D. NO:64:
ATGGGGGTACCGCTCACACGGAGGACGCTGCTCAGTCTGATCCTTGCACT
CCTGTTTCCAAGCATGGCAAGGATGGCGGCTATGGGCAGCTGCTCGAAAG
AGTACCGCATGCTCCTTGGCCAGCTCCAGAAGCAGACAGATCTCATGCAG
GACACCAGCAGGCTCCTGGACCCCTATATACGTATCCAAGGCCTGGATAT
TCCTAAACTGAGAGAGCACTGCAGAGAGAGCCCTGGGGCCTTCCCCAGCG
AGGAGACCCTGAGGGGGCTGGGCAGGCGGGGCTTCCTACAGACGCTCAAT
GCCACACTGGGCTGCGTCCTGCACAGACTGGCCGACTTAGAGCAGCATCT
CCCCAAGGCCCAGGACTTGGAGAGGTCTGGGCTGAACATAGAGGACTTAG
AGAAGCTGCAGATGGCGAGGCCGAATGTCCTCGGGCTCAGGAACAACGTC
TACTGCATGGCCCAGCTGCTGGACAACTCAGACATGACTGAGCCCACGAA
CGCCGGCCGGGGGACCCCTCAGCCGCCCACCCCCACCCCTACCTCAGATG
TTTTTCAGCGCAAGCTGGAGGGCTGCAGTTTCCTGCGTGGCTACCATCGC
TTCATGCACTCAGTGGGGCGGATCTTCAGCAAGTGGGGGGAGAGCCCGAA
CCGCAGCCCGAGACACAGCCCCCACCAGGCCCTGCGGAAGGGGGTGCGCA
CGACGAGACCCTCCAGGAAAGGCAATAGACTCATGCCCAGGGGACAGCTG
CCCCGGTAG

These results confirm that the correct 15E10 variable regions have been cloned successfully to produce an antigen binding chimaeric antibody capable of binding both human and cynomologus OSM site II. The 15E10 variable heavy and light domains can now be humanised.

5.1.1 Search of the Mouse Database 15 mouse sequences with the highest homology for the 15E10 $V_H$ amino acid sequence and 10 mouse sequences with the highest homology for the $V_L$ amino acid sequence were identified by searching a peptide database.

The 15E10 $V_H$ amino acid sequence was compared to all 15 mouse sequences from the database search and the following framework residues were identified as significant:

| Position | 15E10 $V_H$ | mouse | occurence |
|---|---|---|---|
| 75 | R | K | 15/15 |
| 105 | T | Q | 14/15 |

Position is according to the Kabat et al numbering system, supra The 15E10 $V_L$ amino acid sequence was compared to 10 mouse sequences from the database search and the following framework residues were identified as significant:

| Position | 15E10 $V_L$ | mouse | occurence |
|---|---|---|---|
| 9 | T | A | 8/10 |
| 38 | E | Q | 10/10 |
| 49 | E | Y | 10/10 |
| 60 | A | V | 10/10 |

5.1.2. Search of the Human Database

Human framework sequences with the highest homology to 15E10 $V_H$ and $V_L$ frameworks were identified using the EasyBlast in a peptide database.

Two sets of human sequences were identified for 15E10 $V_H$:

Group A of which the following framework was selected for humanisation:

| Position (Kabat#) | 15E10 $V_H$ | Group A | Group B |
|---|---|---|---|
| 27 | F | G | F |
| 28 | S | S | T |
| 29 | L | I | F |
| 30 | T | S | S |
| 48 | L | I | V |
| 49 | G | G | A |
| 67 | L | V | F |
| 71 | K | V | R |
| 73 | N | T | N |
| 78 | V | F | L |
| 94 | K | R | R |

The CDRs are underlined.

And

Group B of which the following was selected for humanisation:

(SEQ. I.D. NO:26)
QVQLQESGPGLVKPSETLSLTCTVSGGSISSYYWSWIRQPPGKGLEWIGY

IYYSGSTNYNPSLKSRVTISVDTSKNQFSLKLSSVTAADTAVYYCARSPS

SGSYYYYYGMDVWGQGTTVTVSS

The CDRs are underlined

The following framework residues were identified as potentially important in recovering affinity and may need to be backmutated:

(SEQ. I.D. NO:27)
QVQLVESGGGVVQPGRSLRLSCAASGFTFSSYGMHWVRQAPGKGLEWVAV

IWYDGSNKYYADSVKGRFTISRDNSKNTLYLQMNSLRAEDTAVYYCARDL

GGPLYWYFDLWGRGTLVTVSS 8 humanised $V_H$ constructs with different backmutations were designed, 4 based on group A human frameworks (A1, A2, A3 and A4) and 4 based on group B human frameworks (B1, B2, B3 and B4).

One set of human sequences was identified for 15E10 V$_L$ of which the following was selected for humanisation:

(SEQ. I.D. NO:28)
EIVLTQSPATLSLSPGERATLSC<u>RASQSVSKYLA</u>WYQQKPGQAPRLLIY<u>D
ASNRAT</u>GTPARFSGSGSGTDFTLTISNLEPEDFAVYYC<u>QQRSNWPPT</u>FGQ
GTKLEI

The CDRs are underlined.

The following residues were identified as potentially important in recovering affinity and may need to be backmutated:

| Position (Kabat#) | 15E10 V$_L$ | Human V$_L$ |
|---|---|---|
| 49 | E | Y |
| 71 | Y | F |

Two constructs were designed, one as a straight graft (L1), the other with backmutations at both residues (L2).

Humanised V$_H$ Construct A1:

(SEQ. I.D. NO:29)
QVQLQESGPGLVKPSETLSLTCTVSGFSLTNYGVHWIRQPPGKGLEWIGV
IWRGGSTDYNAAFMSRVTISVDTSKNQVSLKLSSVTAADTAVYYCAKSPN
SNFYWYFDVWGQGTTS

Humanised V$_H$ Construct A2:

(SEQ. I.D. NO:30)
QVQLQESGPGLVKPSETLSLTCTVSGFSLTNYGVHWIRQPPGKGLEWIGV
IWRGGSTDYNAAFMSRVTISKDTSKNQVSLKLSSVTAADTAVYYCAKSPN
SNFYWYFDVWGQGTTS

Humanised V$_H$ Construct A3:

(SEQ. I.D. NO:31)
QVQLQESGPGLVKPSETLSLTCTVSGFSLTNYGVHWIRQPPGKGLEWIGV
IWRGGSTDYNAAFMSRVTISKDTSKNQVSLKLSSVTAADTAVYYCAKSPN
SNFYWYFDVWGQGTTS

Humanised V$_H$ Construct A4:

(SEQ. I.D. NO:32)
QVQLQESGPGLVKPSETLSLTCTVSGFSLTNYGVHWIRQPPGKGLEWIGV
IWRGGSTDYNAAFMSRVTISKDTSKNQVSLKLSSVTAADTAVYYCAKSPN
SNFYWYFDVWGQGTTS

Humanised V$_H$ Construct B1:

(SEQ. I.D. NO:33)
QVQLVESGGGVVQPGRSLRLSCAASGFSLTNYGVHWVRQAPGKGLEWVAV
IWRGGSTDYNAAFMSRFTISRDNSKNTLYLQMNSLRAEDTAVYYCARSPN
SNFYWYFDVWGRGTLV

Humanised V$_H$ Construct B2:

(SEQ. I.D. NO:34)
QVQLVESGGGVVQPGRSLRLSCAASGFSLTNYGVHWVRQAPGKGLEWVAV
IWRGGSTDYNAAFMSRFTISRDNSKNTLYLQMNSLRAEDTAVYYCAKSPN
SNFYWYFDVWGRGTLV

Humanised V$_H$ Construct B3:

(SEQ. I.D. NO:35)
QVQLVESGGGVVQPGRSLRLSCAASGFSLTNYGVHWVRQAPGKGLEWVAV
IWRGGSTDYNAAFMSRFTISKDNSKNTLYLQMNSLRAEDTAVYYCAKSPN
SNFYWYFDVWGRGTLV

Humanised V$_H$ Construct B4:

(SEQ. I.D. NO:36)
QVQLVESGGGVVQPGRSLRLSCAASGFSLTNYGVHWVRQAPGKGLEWVAV
IWRGGSTDYNAAFMSRLTISKDNSKNTLYLQMNSLRAEDTAVYYCAKSPN
SNFYWYFDVWGRGTLV

Humanised V$_L$ Construct L1:

(SEQ. I.D. NO:37)
EIVLTQSPATLSLSPGERATLSCSGSSSVSYMYWYQQKPGQAPRLLIYDT
SNLASGIPARFSGSGSGTDFTLTISNLEPEDFAVYYCQQWSSYPPTFGQG
TKLEIK

Humanised V$_L$ Construct L2:

(SEQ. I.D. NO:38)
EIVLTQSPATLSLSPGERATLSCSGSSSVSYMYWYQQKPGQAPRLLIEDT
SNLASGIPARFSGSGSGTDYTLTISNLEPEDFAVYYCQQWSSYPPTFGQG
TKLEIK 5.2 Humanisation of 15E10

Humanised V$_H$ and V$_L$ constructs were prepared de novo by build up of overlapping oligonucleotides including restriction sites for cloning into Rld and Rln mammalian expression vectors as well as a human signal sequence. Hind III and Spe I restriction sites were introduced to frame the V$_H$ domain containing the human signal sequence for cloning into Rld containing the human γ1 wild type constant region. Hind III and BsiW I restriction sites were introduced to frame the V$_L$ domain containing the human signal sequence for cloning into Rln containing the human kappa constant region.

Human signal sequence: MGWSCIILFLVATATGVHS (SEQ. I.D. NO:39) Eight humanised V$_H$ constructs and two humanised V$_L$ constructs were designed. This would result in 16 different chain combinations. Since oligo build up of variable regions is time consuming, it was decided initially to prepare only the least and most backmutated constructs for the V$_H$ domain (A1, A4, B1 and B4) and produce humanised antibodies in combination with the two humanised V$_L$ constructs.

10 oligonucleotides 60 bases long with a minimum of 18 base overlap were designed for build up.

5.2.1 Oligonucleotide Build-Up

Oligonucleotide pool solutions were prepared from 5 μl of each oligo stock solution at 100 μM. Synthesis of the humanised $V_H$ and $V_L$ genes by build up of overlapping oligonucleotides was carried out generally according to Stemmer W P et al (1995) Gene 164(1):49-53 using software described in Ertl P F et al (2003) Methods 31:199-206.

5.2.1.1 Assembly PCR Reaction:

| | |
|---|---|
| water | 41.5 μl |
| 10× ProofStart PCR buffer | 5 μl |
| dNTP (10 mM) | 1.5 μl |
| oligo pool | 1 μl |
| ProofStart DNA Polymerase | 1 μl |
| total vol | 50 μl |

| Assembly PCR cycle: | |
|---|---|
| | 1- 94° C. for 2 min |
| | 2- 94° C. for 30 sec |
| | 3- 40° C. for 2 min |
| | 4- 72° C. for 10 sec |
| | 5- 94° C. for 15 sec |
| | 6- 40° C. for 30 sec |
| | 7- 72° C. for 20 sec + 3 sec/cycle |
| steps 4 to 7 were repeated 25 times | |

5.2.1.2 Recovery PCR

Primers 1 and 2 were the first upper and lower oligonucleotides used in the assembly PCR. The recovery PCR allows the amplification of the complete V gene.

Recovery PCR reaction:

| | |
|---|---|
| water | 42 μl |
| 10× ProofStart PCR buffer | 4 μl |
| dNTP (10 mM) | 1.5 μl |
| primer 1 (100 μM) | 0.5 μl |
| primer 2 (100 μM) | 0.5 μl |
| assembly PCR reaction | 1 μl |
| ProofStart DNA Polymerase | 0.5 μl |
| total vol | 50 μl |

| | primer 1 | primer 2 |
|---|---|---|
| 15E10-A1/A4 | 15E10-A4-U1 | 15E10-A4-L1 |
| 15E10-B1 | 15E10-B1-U1 | 15E10-B1-L1 |
| 15E10-B4 | 15E10-B1-U1 | 15E10-B4-L1 |
| 15E10-L1/L2 | 15E10-L1-U1 | 15E10-L1-L1 |

| Recovery PCR cycle: | |
|---|---|
| | 1- 94° C. for 2 min |
| | 2- 94° C. for 45 sec |
| | 3- 60° C. for 30 sec |
| | 4- 72° C. for 2 min |
| | 5- 72° C. for 4 min |
| steps 2 to 4 were repeated 25 times | |

The recovery PCR products were purified using the MinElute PCR Purification kit from Qiagen according to manufacturer's instructions.

5.2.2 Restriction Digests

Humanised 15E10 $V_H$ constructs A1, A4, B1 and were digested Hind III-Spe I and two humanised 15E10 $V_L$ were digested Hind-III-BsiW I as described in 4.2.1.

5.2.3 Gel Purification

The products of restriction digest were purified as in 4.2.2.

5.2.4 Ligation

The 15E10 humanised $V_H$ fragments Hind III-Spe I digested were ligated into the Rld hCγ1 wt vector Hind III-Spe I digested.

The 15E10 humanised $V_L$ fragments Hind III-BsiW I digested were ligated into the Rln hCκ vector Hind III-BsiW I digested.

The ligation was carried out using the LigaFast Rapid DNA Ligation System from Promega according to manufacturer's instructions.

5.2.5 Transformation

As in 4.2.5

5.2.6 Sequencing

Colonies from each reaction plate were cultured overnight at 37° C. in 5 ml LB medium supplemented with 100 μg/ml ampicillin.

Plasmids were extracted and purified using the QIAprep Spin Miniprep kit from Qiagen according to manufacturer's instructions and sequenced using primers described in 4.2.5.

Clones with the correct humanised $V_H$ and $V_L$ sequences were identified and plasmids prepared for expression in CHO cells.

6. Expression of Humanised Antibodies in CHO Cells

Four humanised $V_H$ constructs (A1, A4, B1 and B4) and two humanised $V_L$ constructs (L1 and L2) were prepared in Rld hCγ1wt and Rln hCκ mammalian expression vectors. Eight plasmid heavy chain-light chain combinations (A1L1, A1L2, A4L2, B1L2, B4L1 and B4l2) were transiently co-transfected into CHO cells and expressed at small scale to give 8 different humanised antibodies. The antibodies produced in supernatant were analysed in the gp130 inhibition ELISA (see below).

6.1 Plasmid Purification

DH5α cells containing one of the plasmids of section 6 were cultured in 5 ml of LB media supplemented with 10 μg/ml ampicillin for 8 h at 37° C. in a shaker incubator.

200 ml of LB media supplemented with 100 μg/ml ampicillin was inoculated with 1 ml of day culture and incubated overnight at 37° C. in a shaker incubator.

The plasmids were extracted and purified using the QIAfilter Plasmid Maxi kit from Qiagen according to manufacturer's instructions. The ethanol pellet was resuspended in 200 μl TE buffer and plasmid concentration was measured by absorbance at 260 nm after 100 fold dilution of stock solution.

6.2 Transfection 9 wells of Corning Costar 3506 6-well plates were seeded with $10^6$ CHO cells and cultured overnight in Dulbecco's MEM with Glutamax-1 (DMEM) media supplemented with Ultra Low Fetal Bovine Serum and 1% Penicillin-Streptomycin at 37° C.

For each well, the following were added in a 5 ml Bijou:
1 ml Optimem 1 with Glutamax-1
5 μg plasmid carrying humanised $V_H$
5 μg plasmid carrying humanised $V_L$
30 μg TransFast Transfection Reagent under vortex so that each transfection contained a different combination of light and heavy chains. Incubation took place for 10-15 min at room temperature. DMEM media was removed from wells then vortex mixture and added to the appropriate well.

Incubation took place at 37° C. for 1 h.

2 ml Optimem was added per well and incubated at 37° C. for 48-72 h.

6.3 Analysis of Humanised Antibodies

Media from each well was recovered and centrifuged at 1300 rpm for 1 min on an Eppendorf 5415R bench centrifuge and supernatant passed through a 0.2 μm Pall Acrodisc 25 mm syringe filter.

Figure 4:
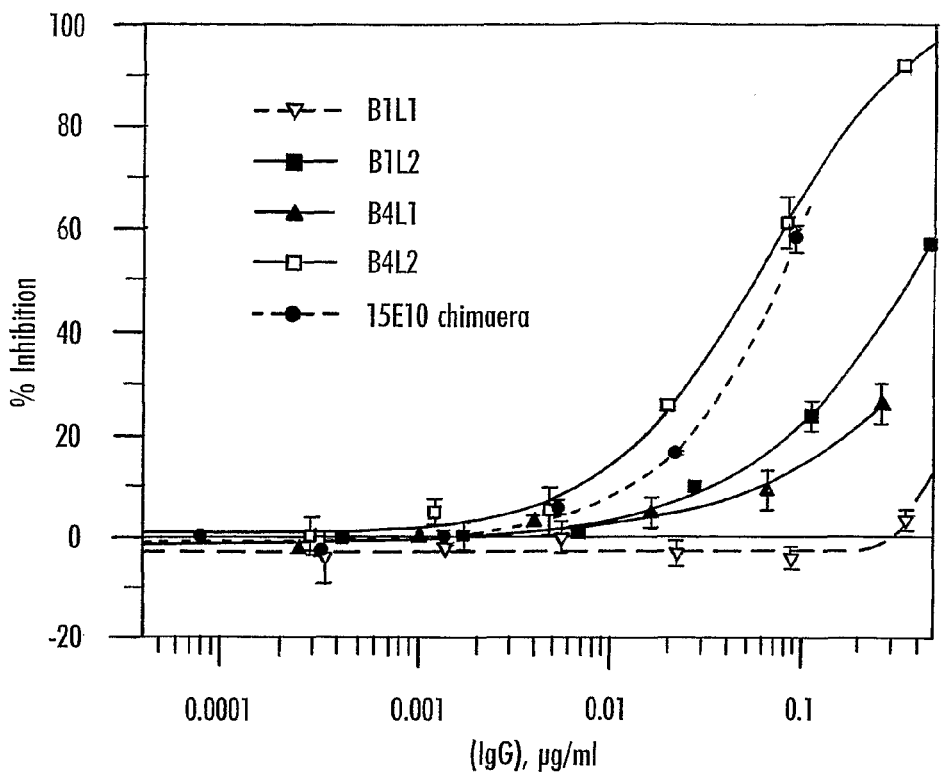
FIG. 4 illustrates gp130 inhibition ELISA against hOSM (upper panel) and cOSM (lower panel) wherein % inhibition as a function of antibody concentration for four humanised antibodies (B1L1, B1L2, B4L1, B4L2) and the chimaeric 15E10 is plotted.
Figure 4:
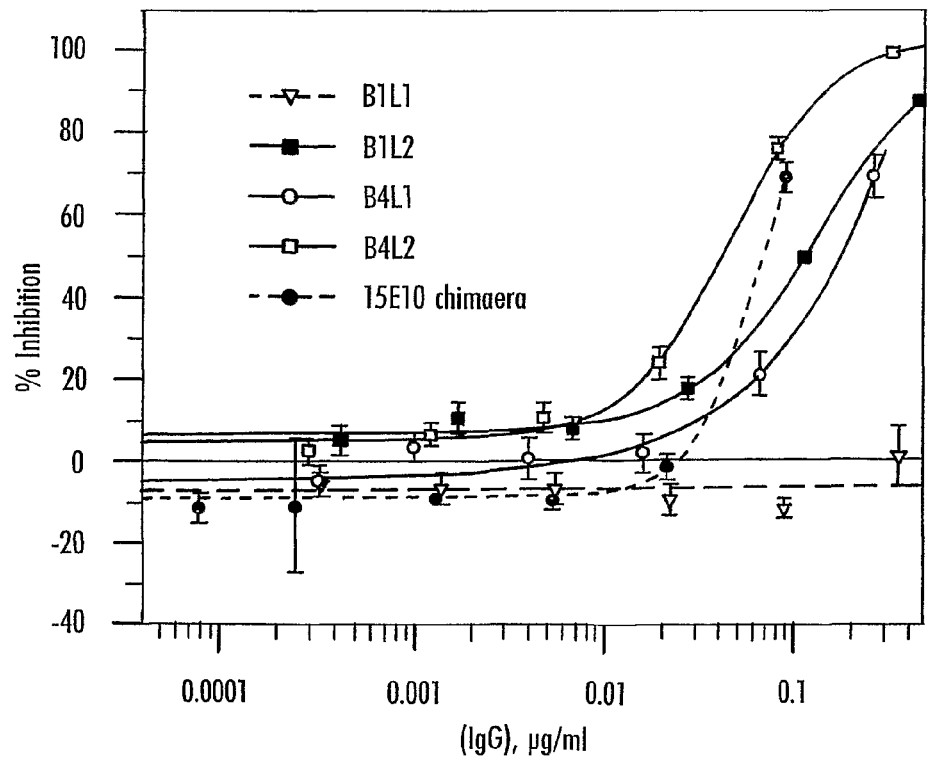
Figure 5:
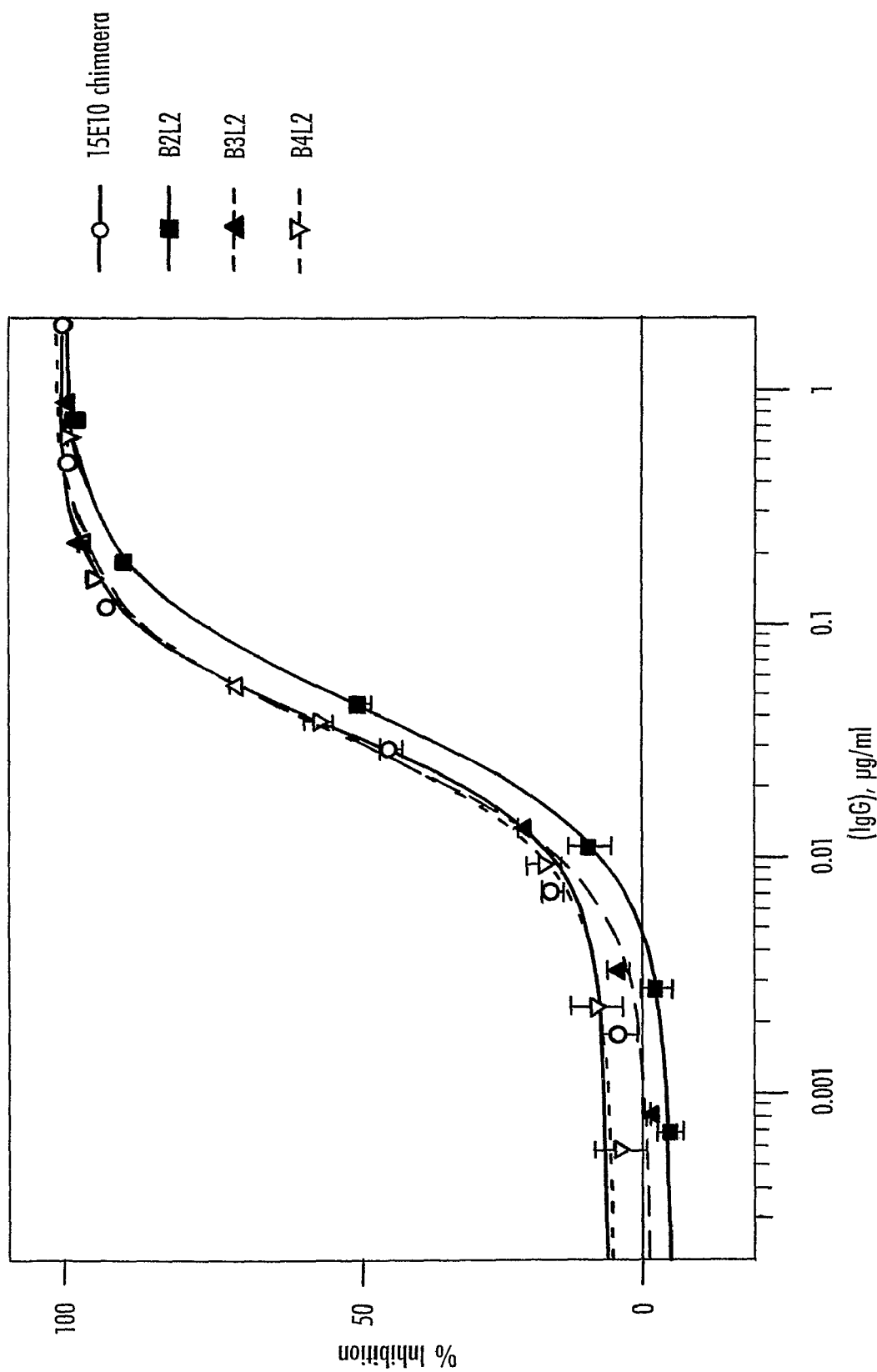
FIG. 5 illustrates the gp130 inhibition ELISA of the examples where various humanised antibodies (B2L2, B3L2, B4L2) are compared to chimaeric 15E10 for binding to CHO produced hOSM.
Figure 6:
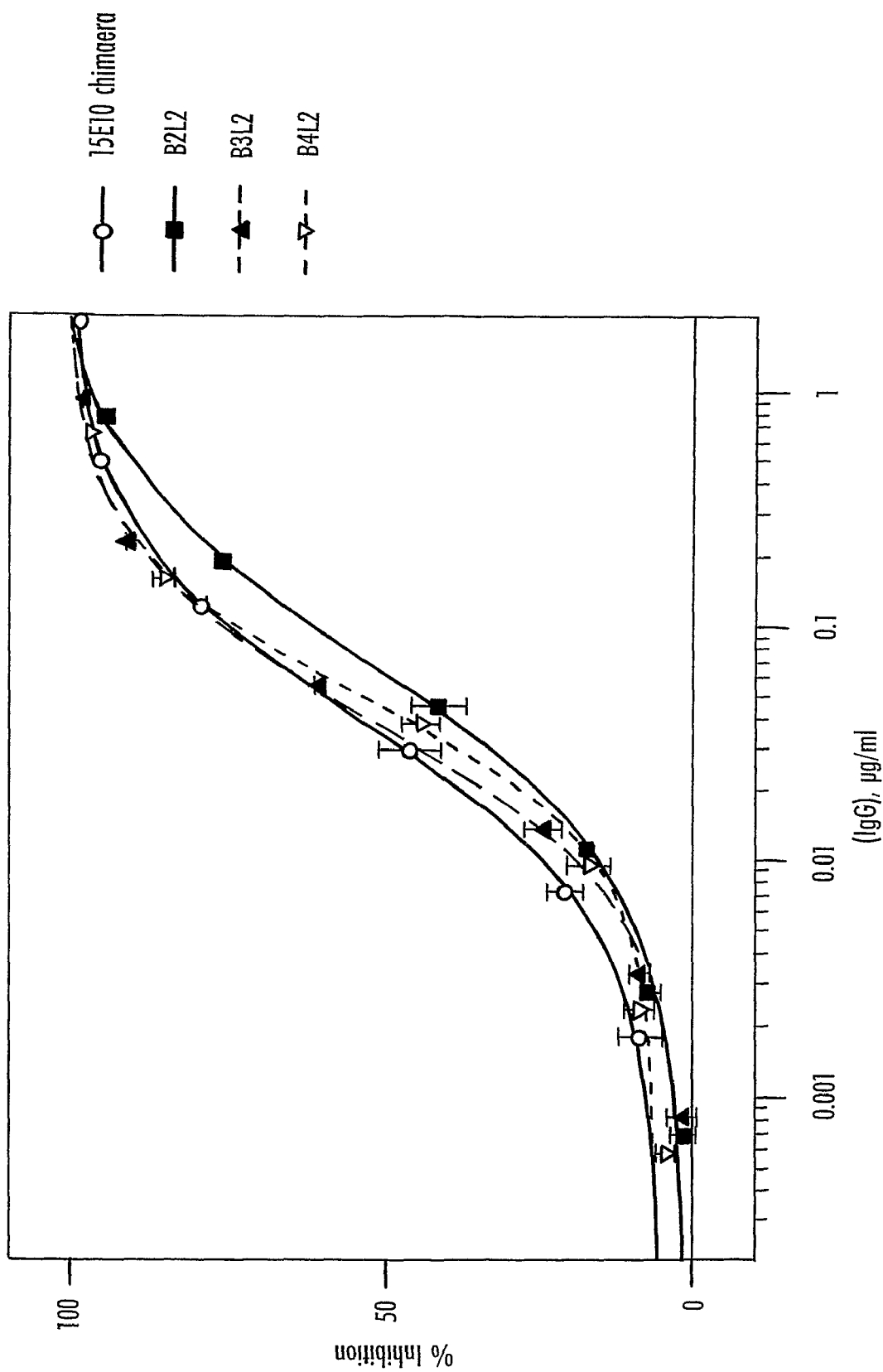
FIG. 6 illustrates the assay of FIG. 5 using cOSM instead of hOSM.
Figure 7:
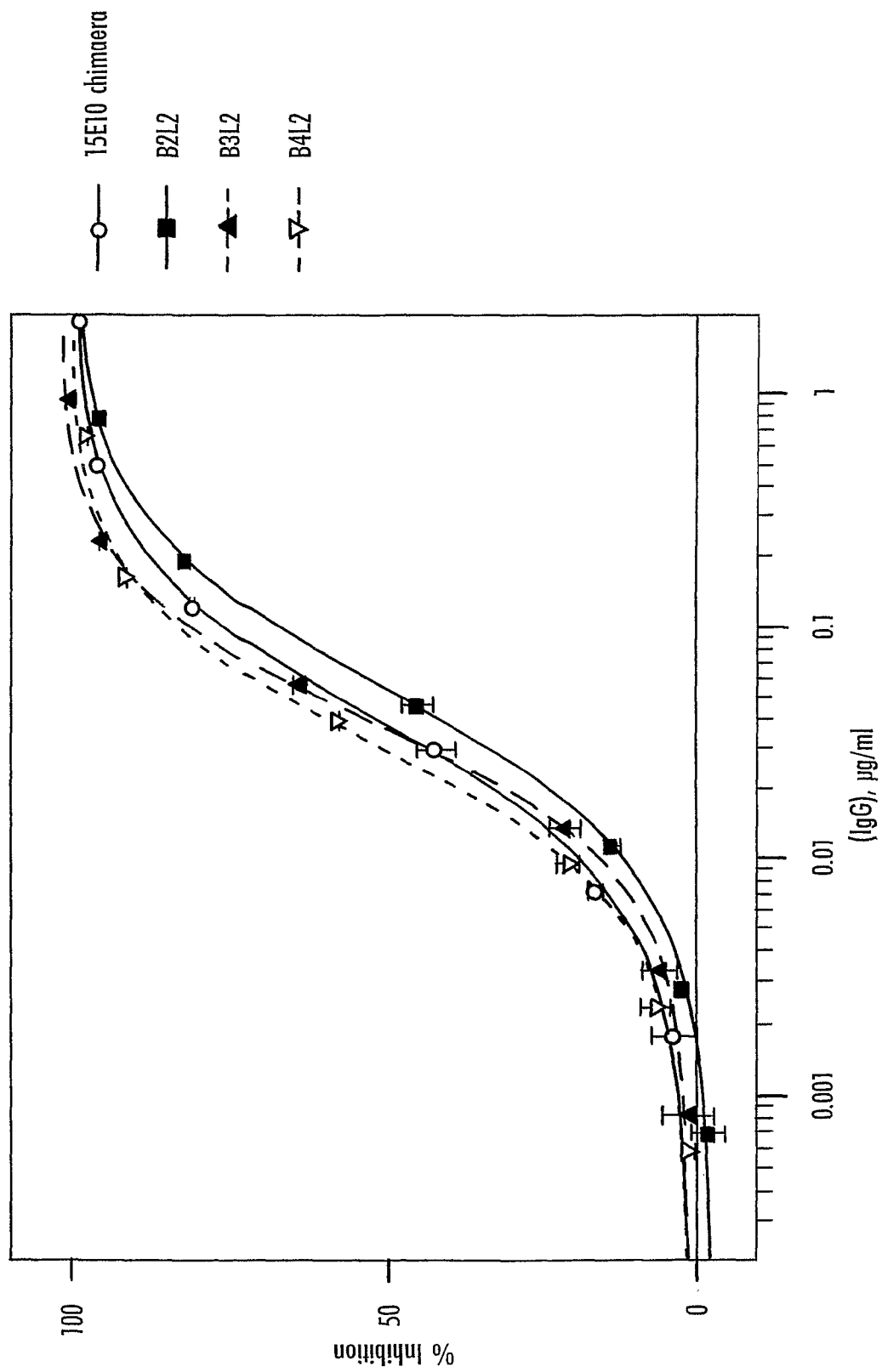
FIG. 7 illustrates the assay of FIG. 5 using CHO produced hOSM in 25% human AB serum.
Figure 8:
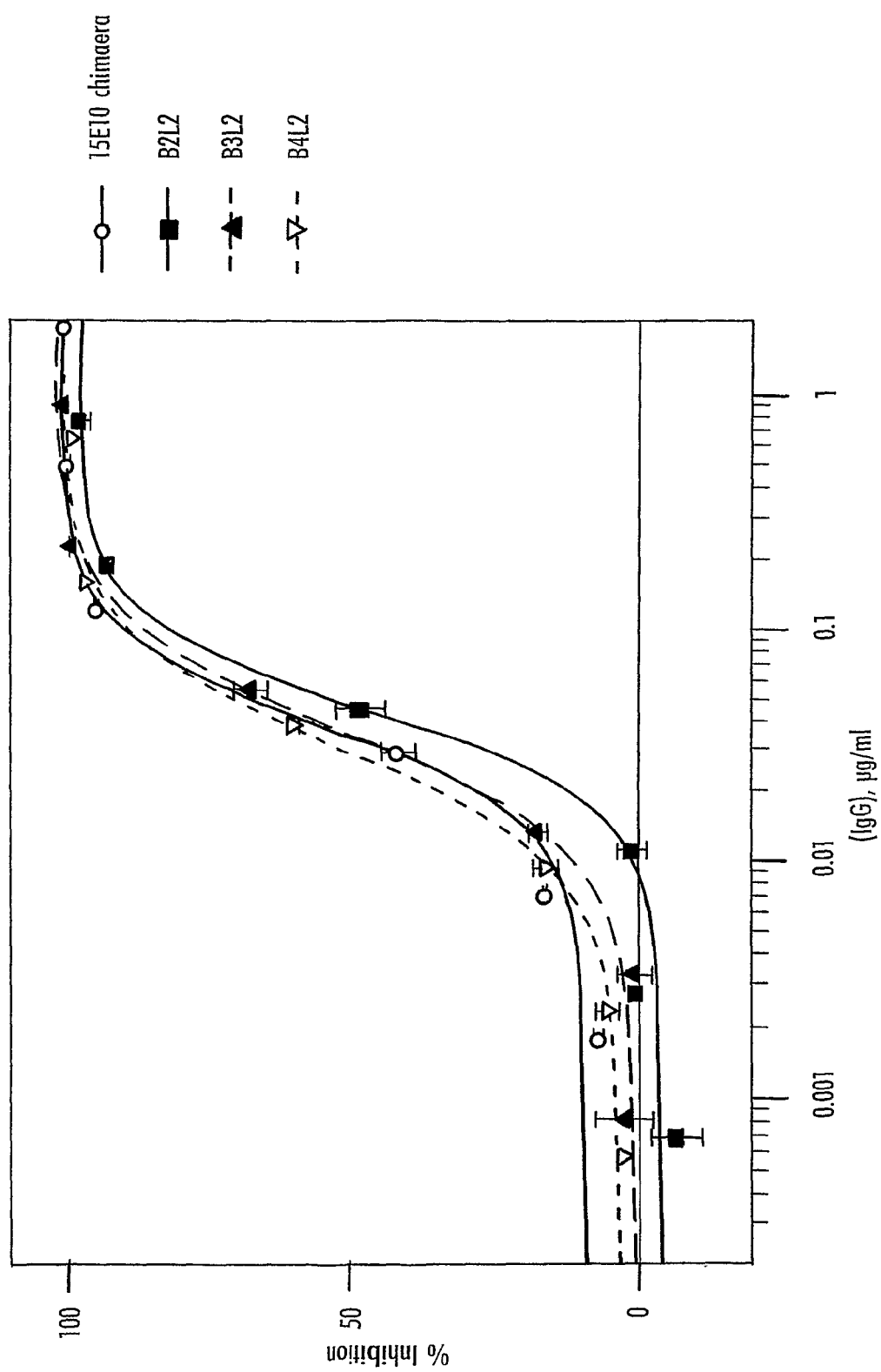
FIG. 8 illustrates the assay of FIG. 7 using cOSM instead of hOSM.
Figure 9:
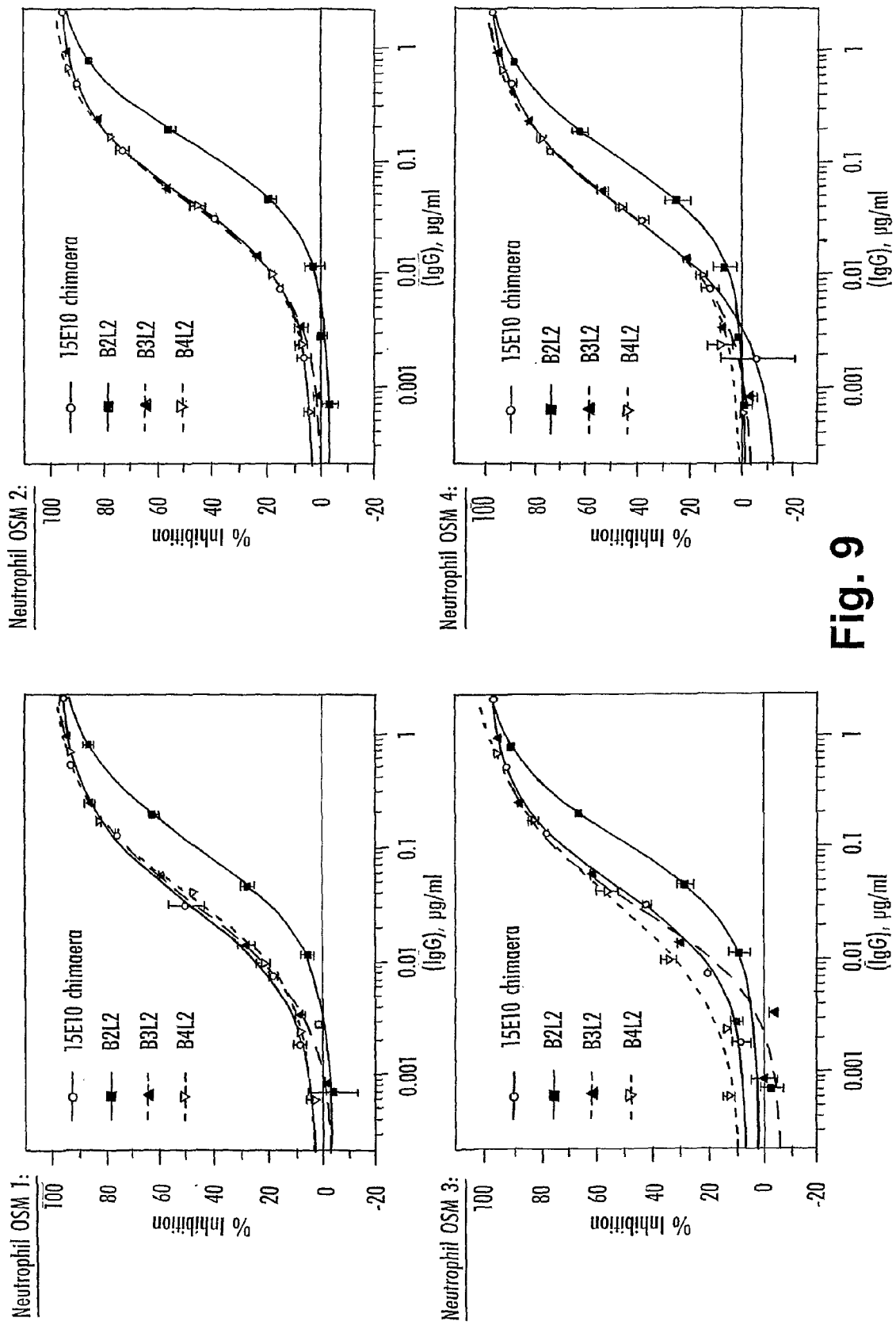
FIG. 9 illustrates the gp130 inhibition ELISA of neutrophil OSM from four different human samples using humanised antibodies B2L2, B3L2, B4L2 and chimaeric 15E10.
Figure 10:
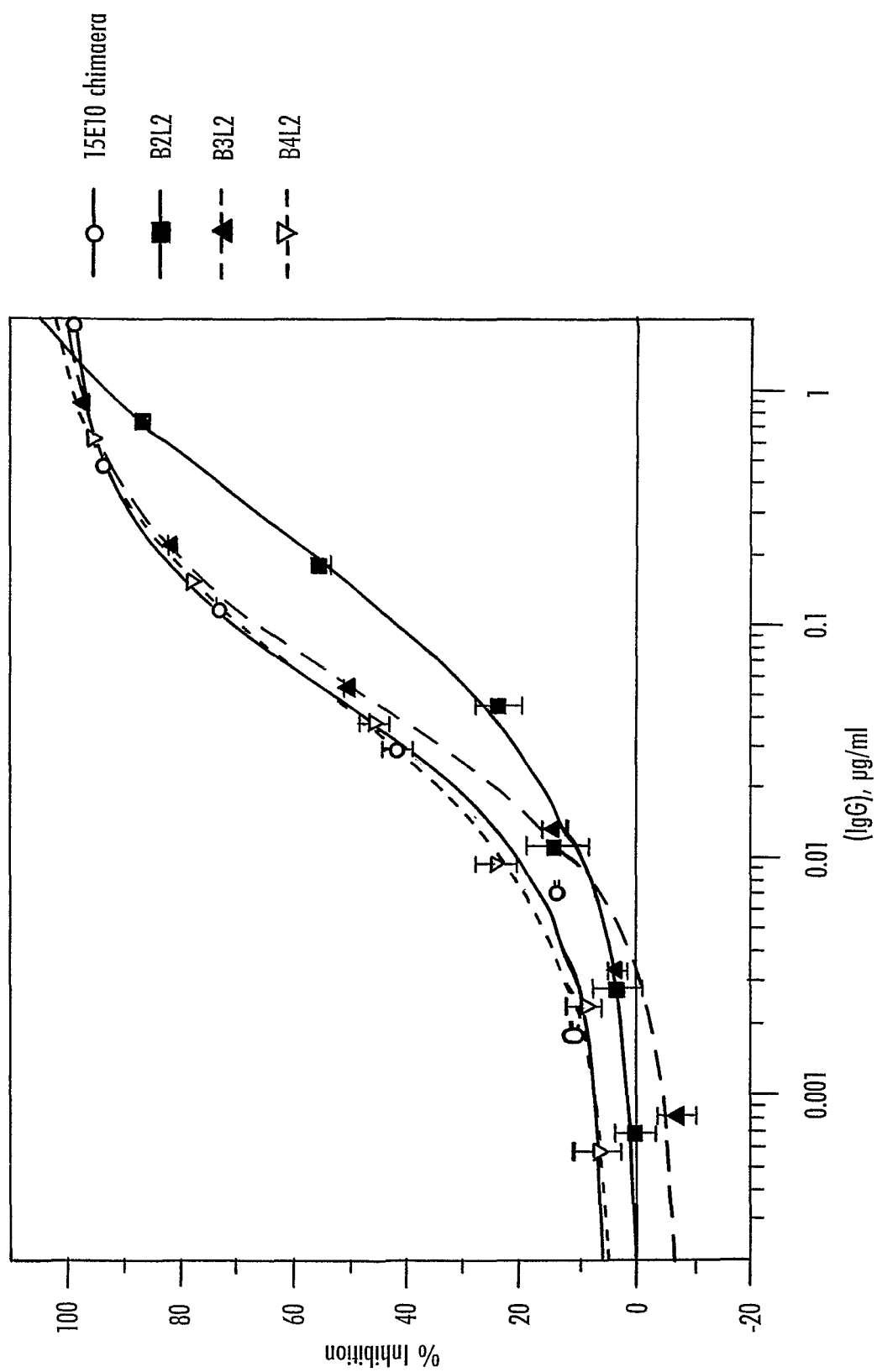
FIG. 10 illustrates the gp130 inhibition ELISA using three humanised antibodies (B2L2, B3L2, and B4L2) and 15E10 chimaeric antibody against hOSM isolated from the synovial fluid of hum an RA patients.
Figure 11:
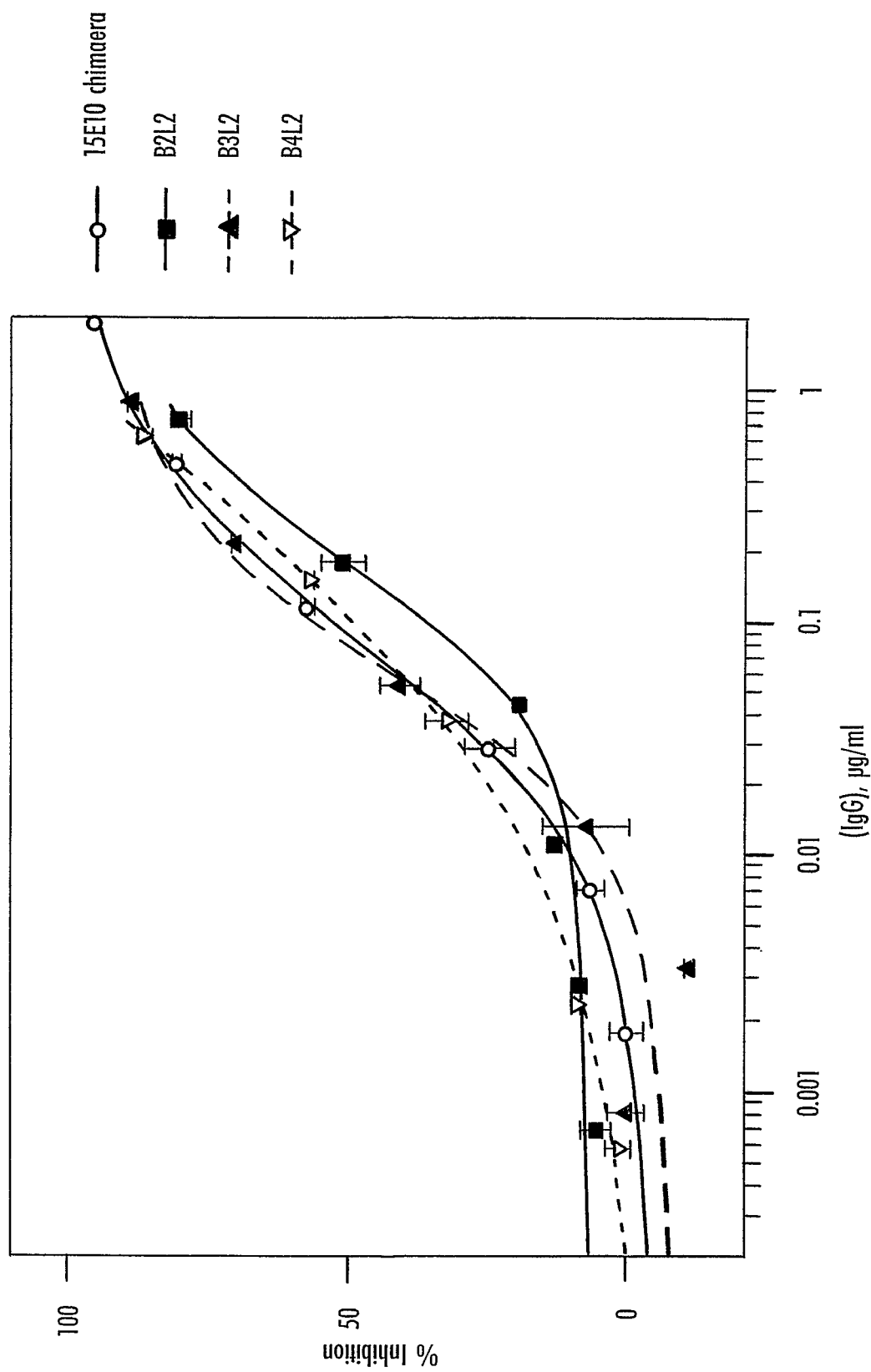
FIGS. 11 to 16 illustrate the results of the conditions of FIGS. 5 to 10 in the KB cell assay instead of gp130 inhibition ELISA with the exception that the KB cell assay of neutrophil OSM of FIG. 15 used a single human sample of neutrophil OSM. Thus
Figure 12:
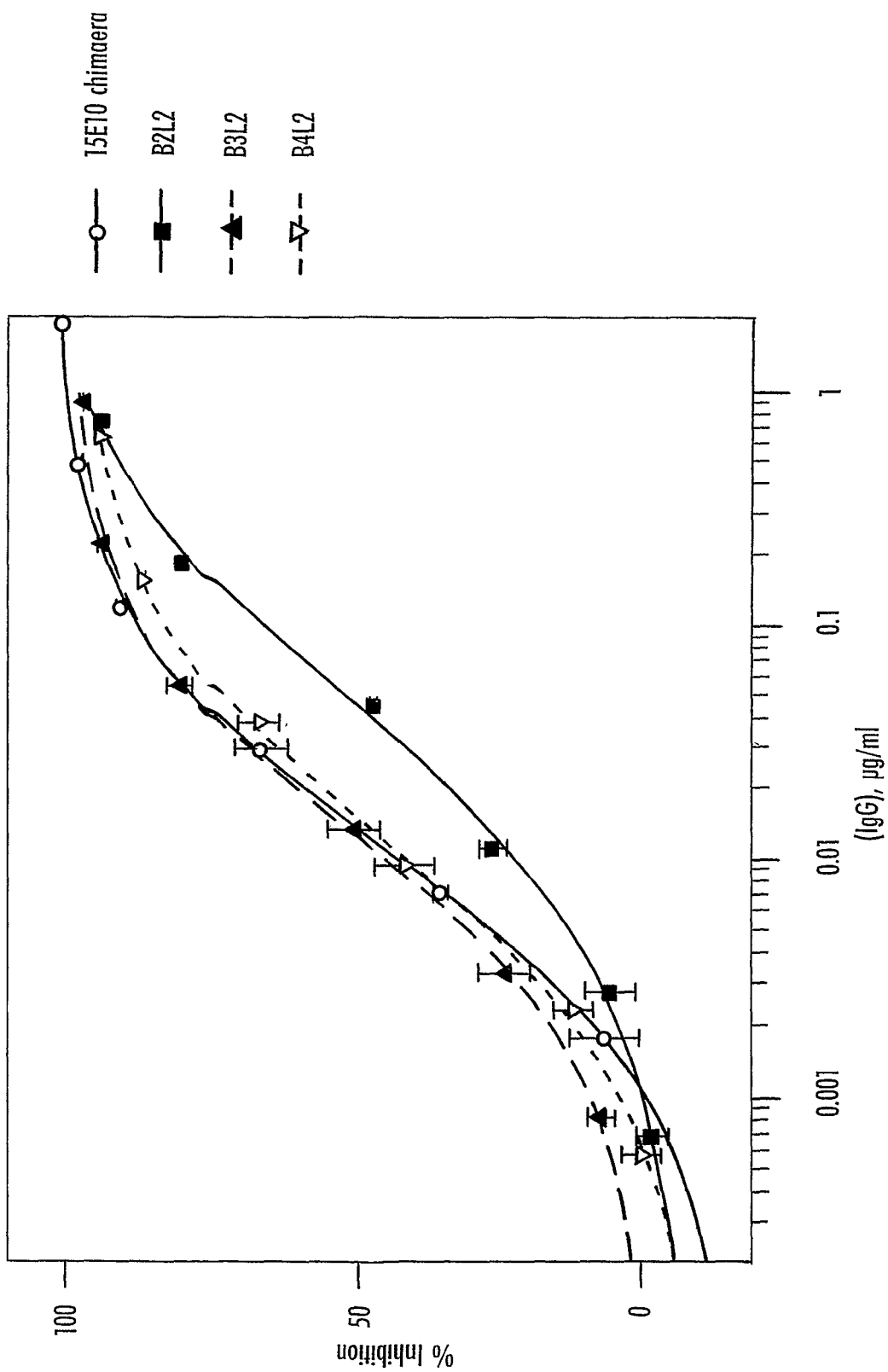
Figure 13:
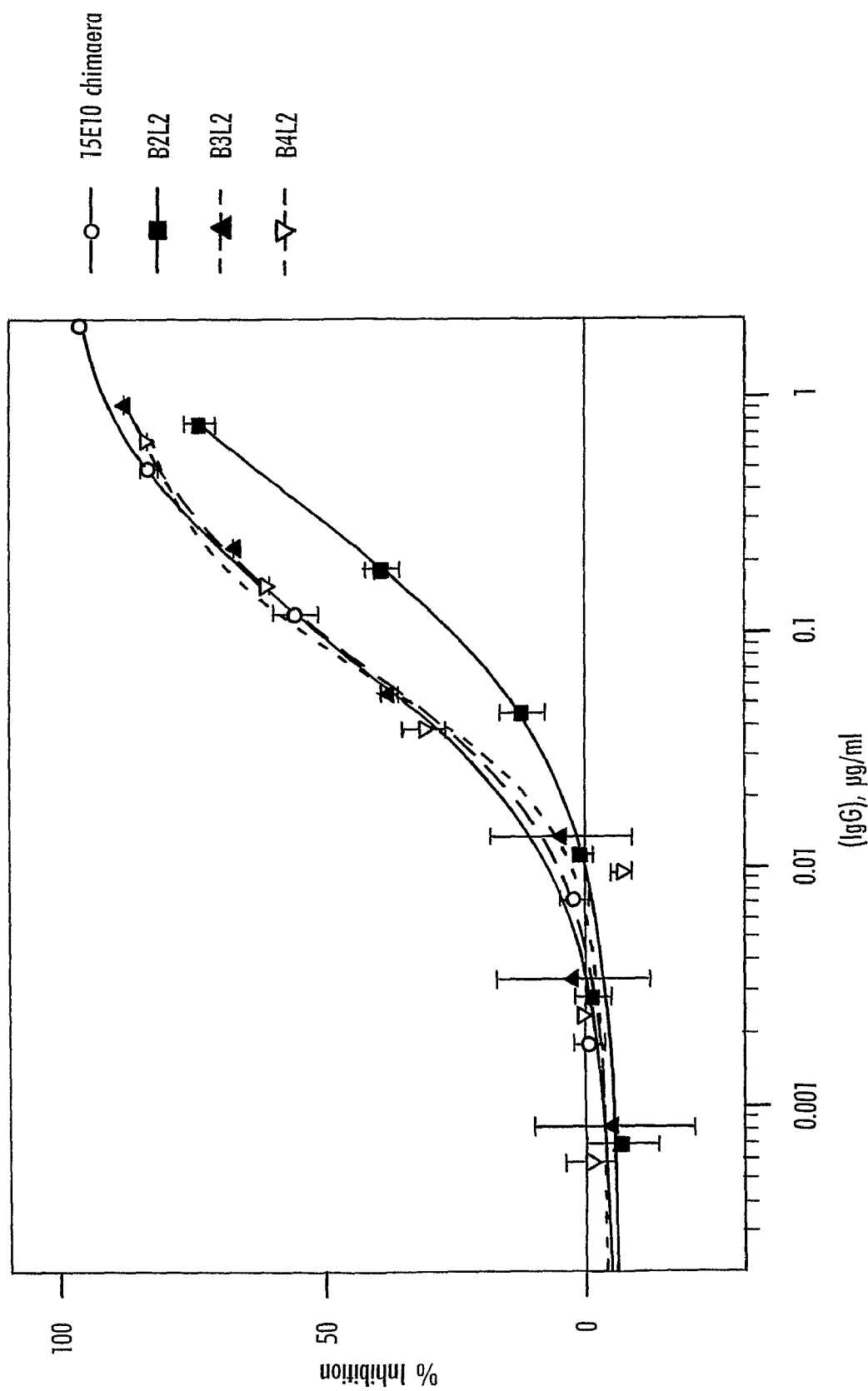
Figure 14:
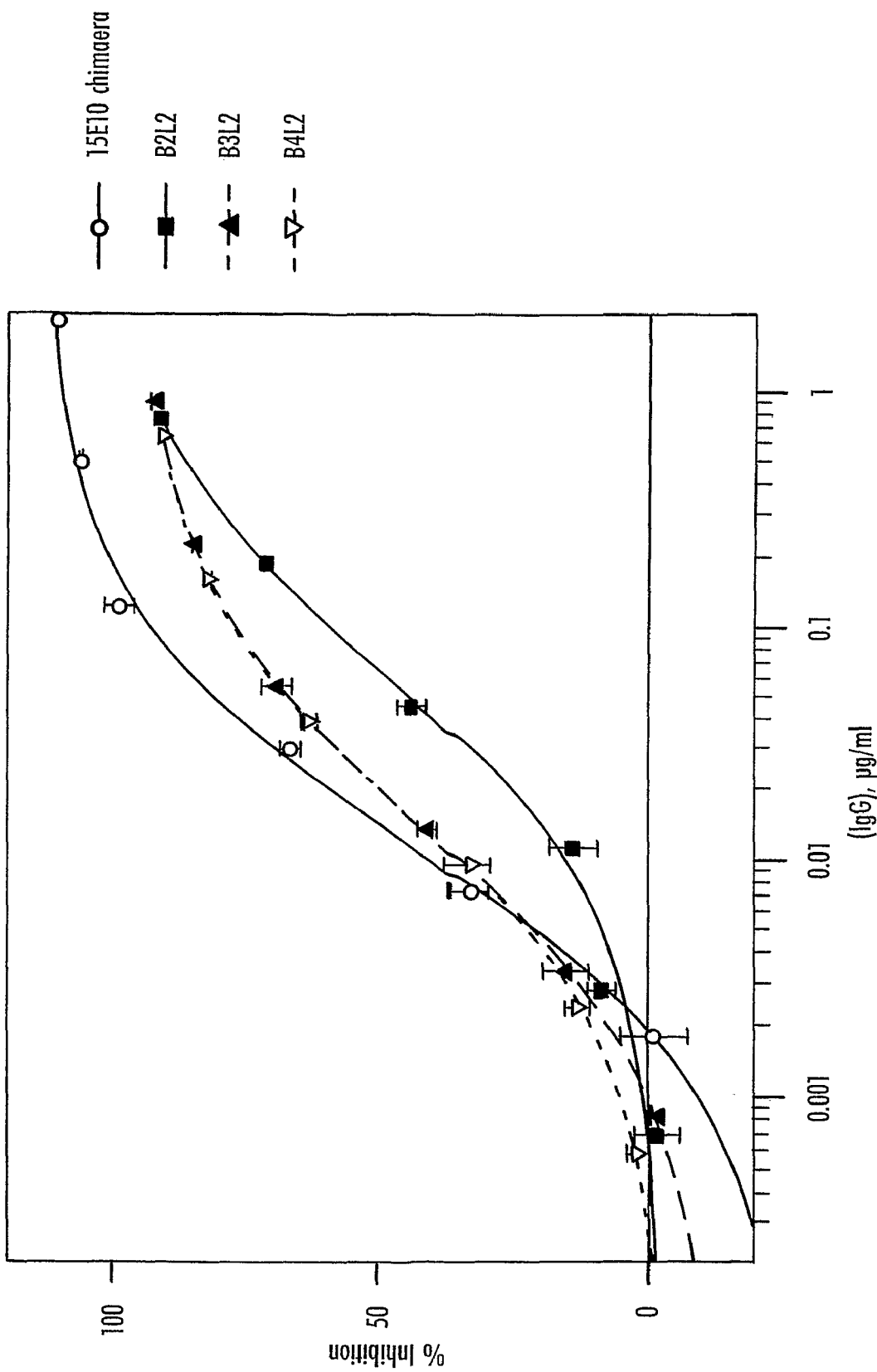
Figure 15:
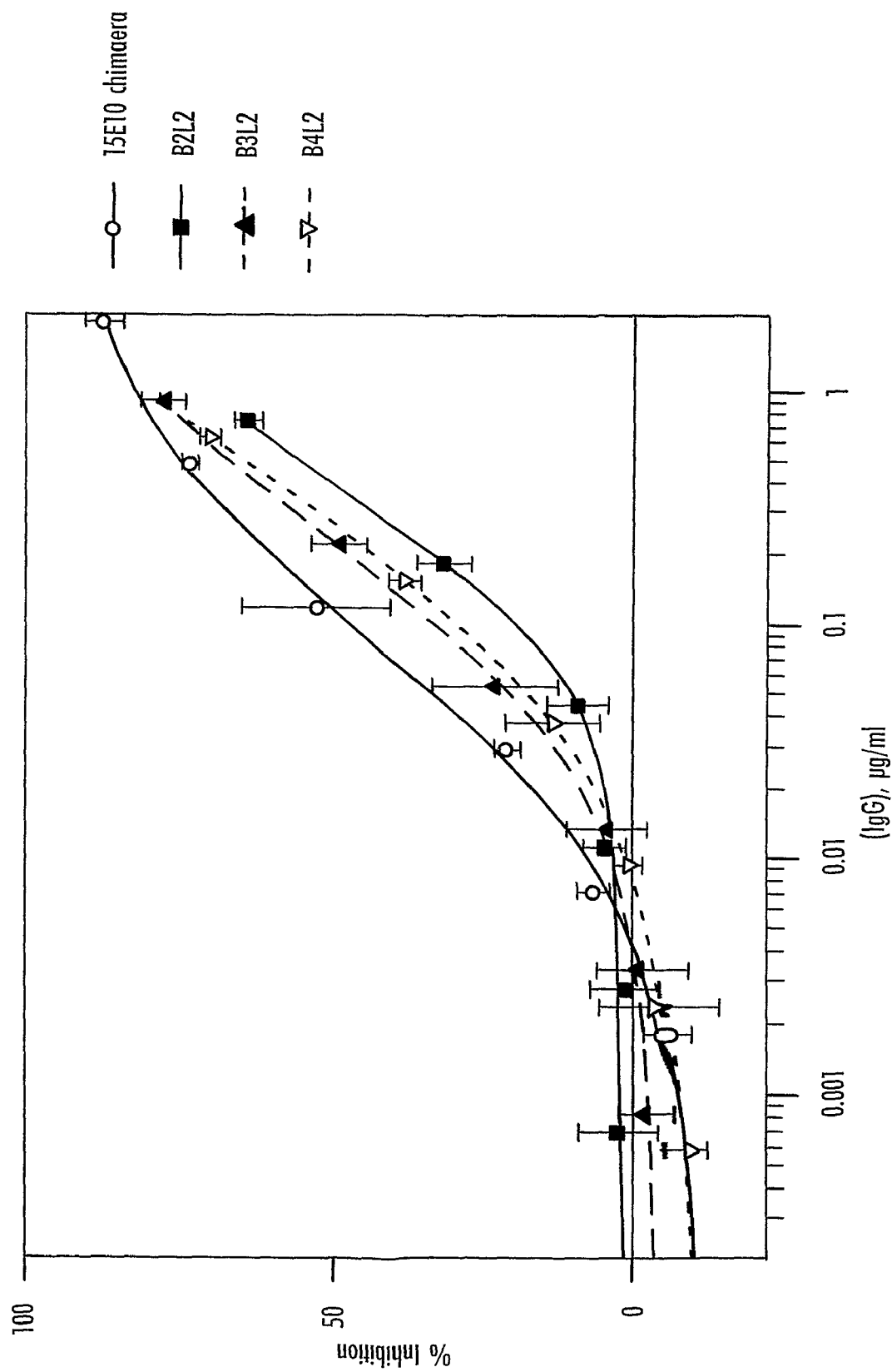
Figure 16:
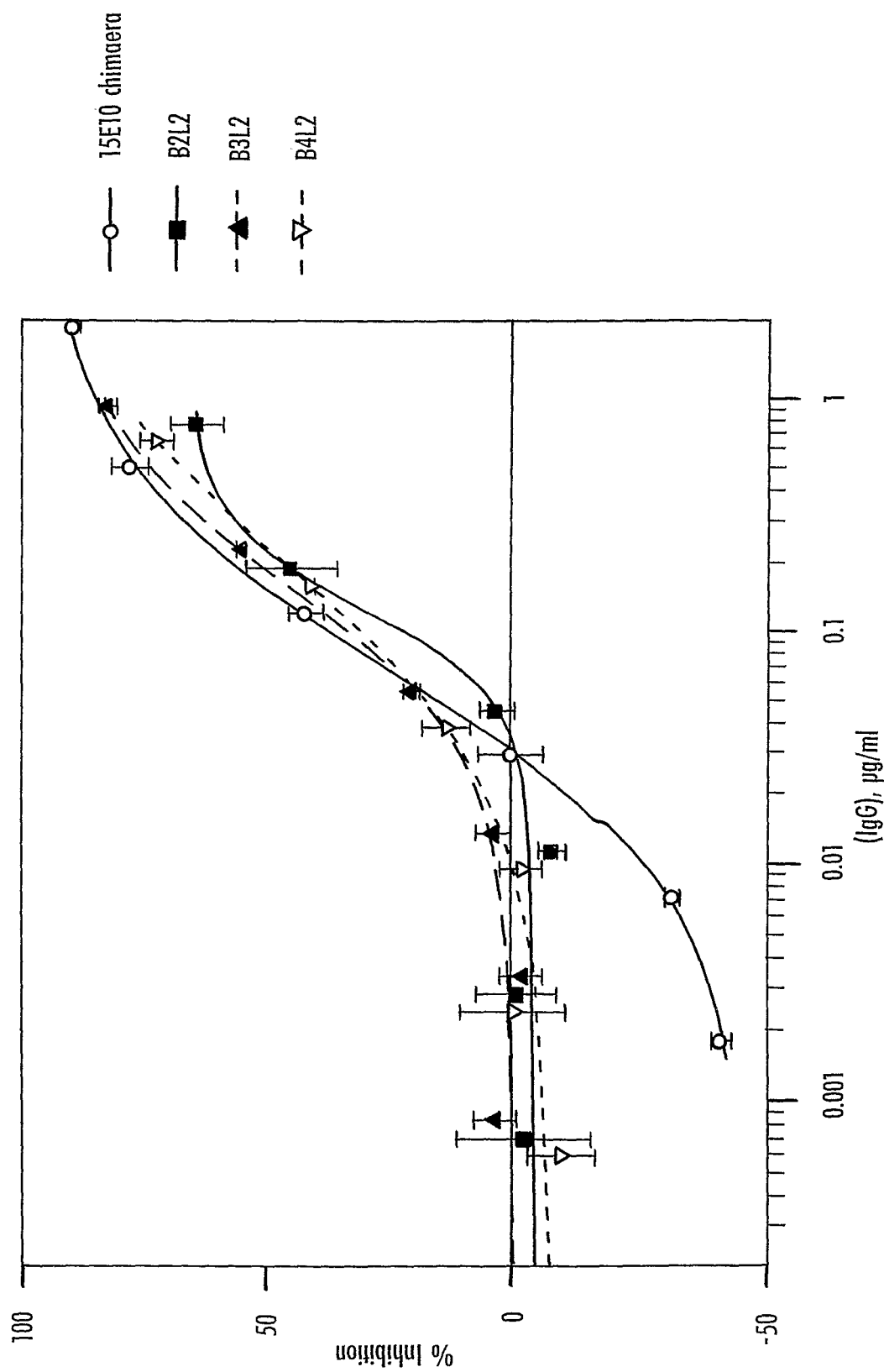

8 humanised antibodies (4 based on the group A human frameworks, 4 based on the group B human frameworks) and the 15E10 chimaeric antibodies were analysed in the gp130 inhibition ELISA for their potency in neutralising both hOSM and cOSM (see FIG. 4).

TABLE 2

IC50 values for humanised antibodies B1L1, B1L2, B4L1 and B4L2 in the gp130 inhibition ELISA

|  | Human OSM | Cynomolgus OSM |
| --- | --- | --- |
| B1L1 | NA | NA |
| B1L2 | 0.334 | 0.110 |
| B4L1 | NA | 0.167 |
| B4L2 | 0.048 | 0.040 |
| 15E10 chimaera | 0.070 | 0.060 |

IC50 values are expressed in μg/ml
NA: inhibition is less than 50%

The level of backmutations in expressed humanised antibodies had a direct effect on affinity for human and cynomologus OSM in the gp130 inhibition ELISA. The least backmutated antibody (B1L1) had no detectable affinity for cynomolgus OSM and just above background for human OSM. On the other hand, the most backmutated antibody (B4L2) had an affinity for human and cynomolgus OSM at least equivalent to that of chimaeric 15E10 antibody. The 2 humanised antibodies containing the backmutated light chain had higher affinity than the 2 humanised antibodies containing the straight graft light chain.

None of the four humanised antibodies based on the human group A frameworks gave an inhibitory signal in the gp130 ELISA assay. In fact none of these antibodies could be detected in an ELISA for complete human IgG1 antibody (where the capture antibody is a polyclonal raised against human γ heavy chain in goats and the detecting antibody is a polyclonal raised against human κ light chain in goats).

Further analysis of supernatant containing these four antibodies in human IgG heavy chain specific and light chain specific ELISAs gave a positive signal in both assays. Both ELISAs used a capture antibody raised against human IgG heavy and light chains in goats while the detection antibody was raised against human IgG γ chain for the heavy chain specific ELISA and against human IgG κ chain in the light chain specific ELISA.

These results suggest that humanised antibodies where the heavy chain was designed from group A human frameworks express both heavy and light chain but the two chains do not combine to produce a viable antibody.

The most backmutated $V_H$ construct based on human Group B frameworks (B4) in combination with the backmutated light chain (L2) proved to be the most potent humanised antibody. Three humanised antibodies comprising $V_H$ from Group B (B2L2, B3L2 and B4L2) were produced, purified and analysed to determine the humanised antibody most suitable for candidate selection.

6.4: Preparation of Humanised $V_H$ Constructs of 6.3

Two humanised constructs B2 and B3 were prepared as in 5.2.1 to 5.2.6

6.5 Expression of Humanised Antibodies in CHO Cells

Three humanised $V_H$ containing plasmids (B2, B3 and B4) in combination with the most backmutated humanised $V_L$ containing plasmid (L2) from section 6 were transiently co-transfected into CHO cells and expressed. The 3 humanised antibodies produced were purified from cell culture supernatant by affinity chromatography on rprotein A Sepharose and their affinity for OSM was evaluated in gp130 inhibition ELISA and KB cell assay using 15E10 chimaeric antibody as reference.

Plasmid purification was carried out as in 4.3.1. Transfection was carried out as in 4.3.2. Purification of humanised antibodies was carried out as in 4.3.3.

6.6 Analysis of Humanised Antibodies of Section 6.5

Purified humanised antibodies from section 6.5 were analysed in the gp130 inhibition ELISA and KB cell assay (see below) for their potency in neutralising both human and cynomolgus OSM. Assays were conducted with human OSM from a variety of sources including CHO produced, CHO produced+25% human AB serum, neutrophils and synovial fluid of RA patients.

gp130 inhibition ELISA: data from experiments are illustrated in FIG. 5 to 10.

KB cell assay: data from experiments are illustrated in FIG. 11 to 16. These results show that humanised antibodies (B3L2 and B4L2) have potency equivalent to 15E10 chimaeric antibody but higher than humanised antibody B2L2. This indicates that the humanisation strategy, especially the choice of backmutations resulted in complete recovery of affinity for antigen.

The amino acid sequence of the $V_H$ chain of B4 is (SEQ.I.D.NO:21)
QVQLVESGGGVVQPGRSLRLSCAASGFSLTNYGVHWVRQAPGKGLEWVAV

IWRGGSTDYNAAFMSRLTISKDNSKNTLYLQMNSLRAEDTAVYYCAKSPN

SNFYWYFDVWGRGTLVTVSS and the $V_L$ chain is SEQ. I.D. NO: 12.

A therapeutic antibody or antigen binding fragment thereof comprising a $V_H$ chain of SEQ. I.D. NO: 21 and a $V_L$ chain of SEQ. I.D. NO: 12 may be considered a competing antibody of the invention and therefore forms an embodiment of the invention.

6.7 Comparison of B3L2 Humanised Antibody with Chimaeric and Parent Murine Antibodies The humanised antibody B3L2 was compared to 15E10 chimaeric and parent murine antibodies in the gp130 inhibition ELISA and KB cell assay (see below) using human and cynomolgus OSM as target antigen.

Figure 17:
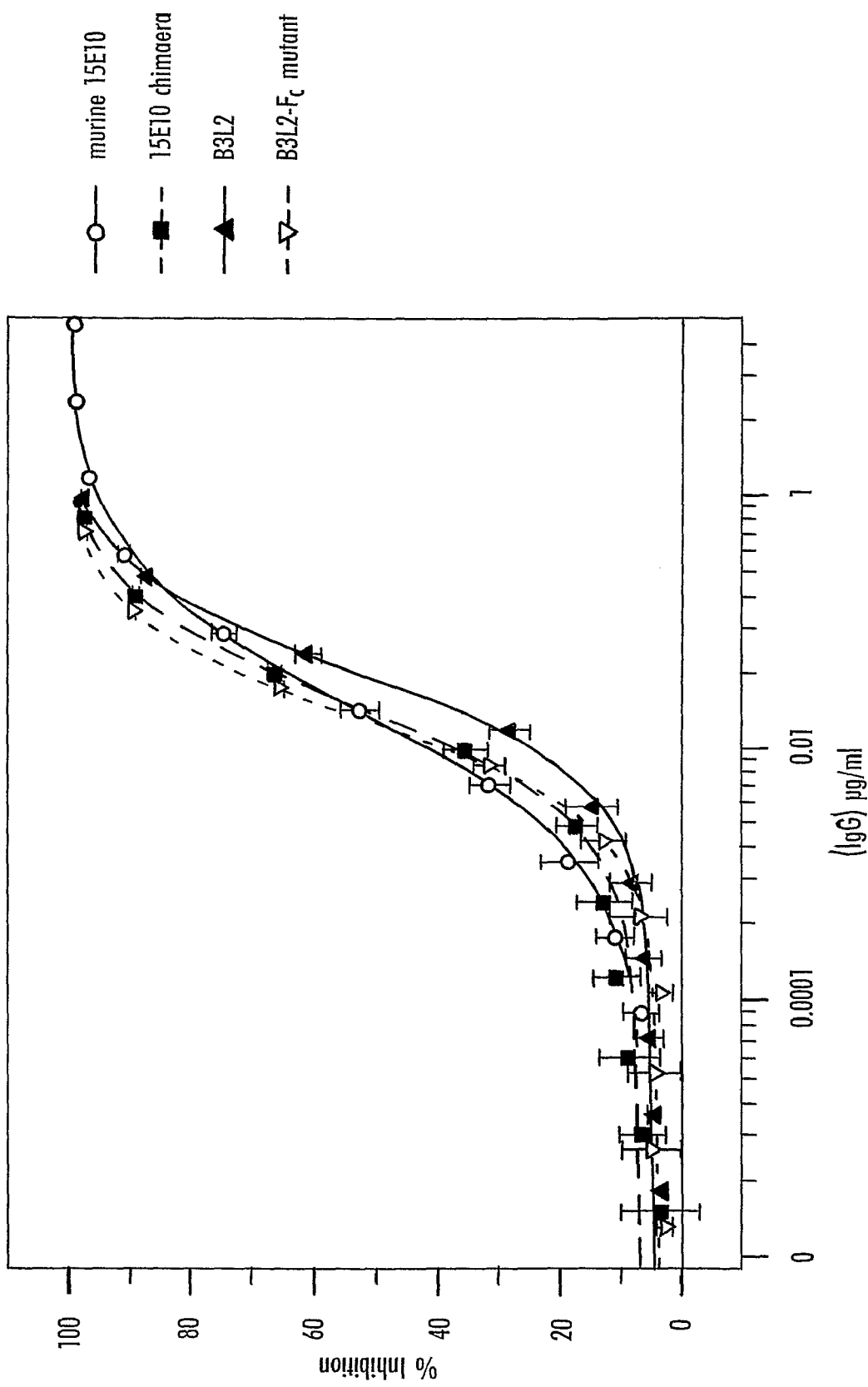
FIG. 17 illustrates the gp130 inhibition ELISA of the parent murine 15E10, the chimaeric 15E10, a humanised antibody construct B3L2, and a Fc lytic mutant of B3L2 against CHO produced hOSM. See description for more detail.
Figure 18:
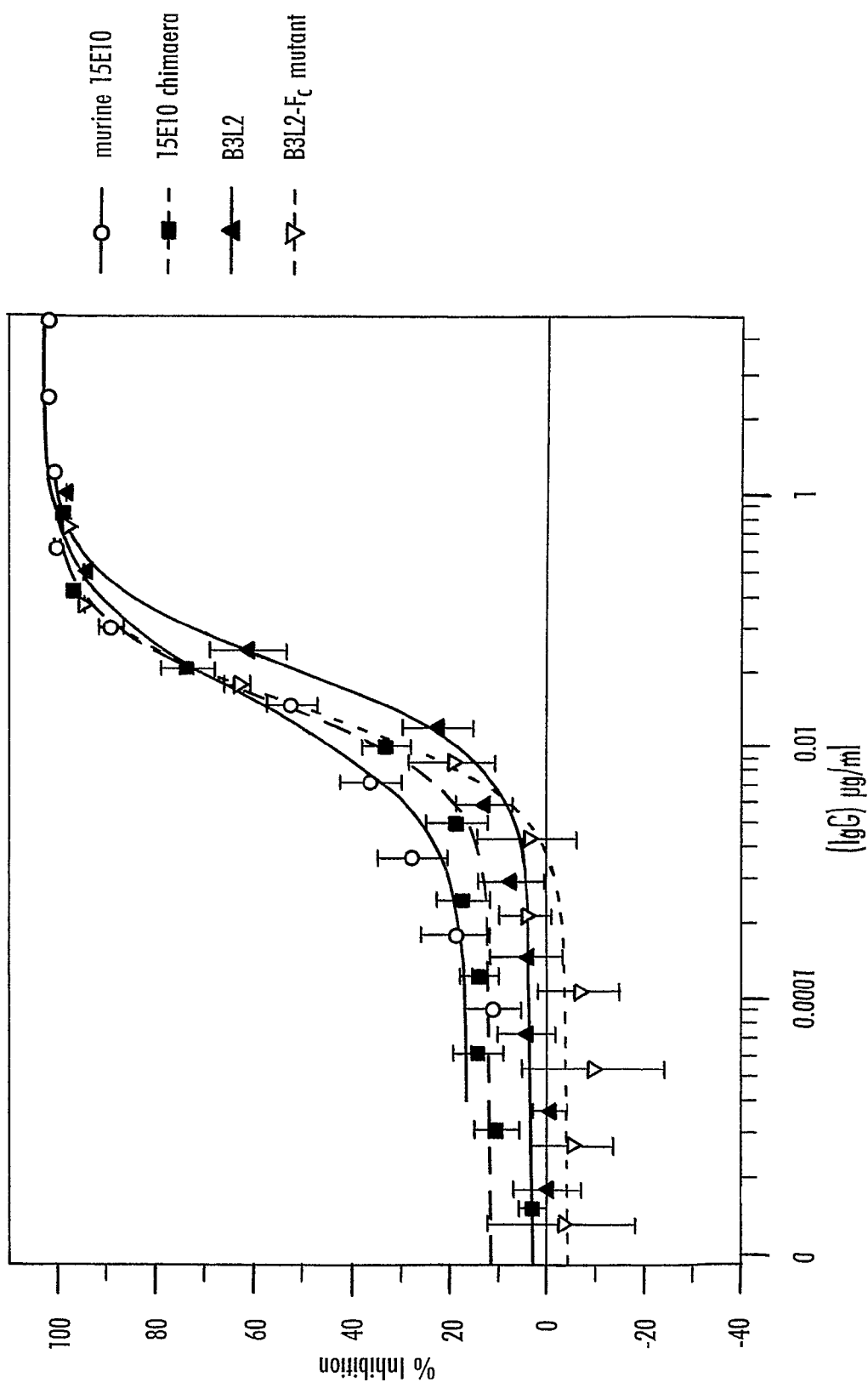
FIG. 18 illustrates the assay of FIG. 17 using cOSM.
Figure 19:
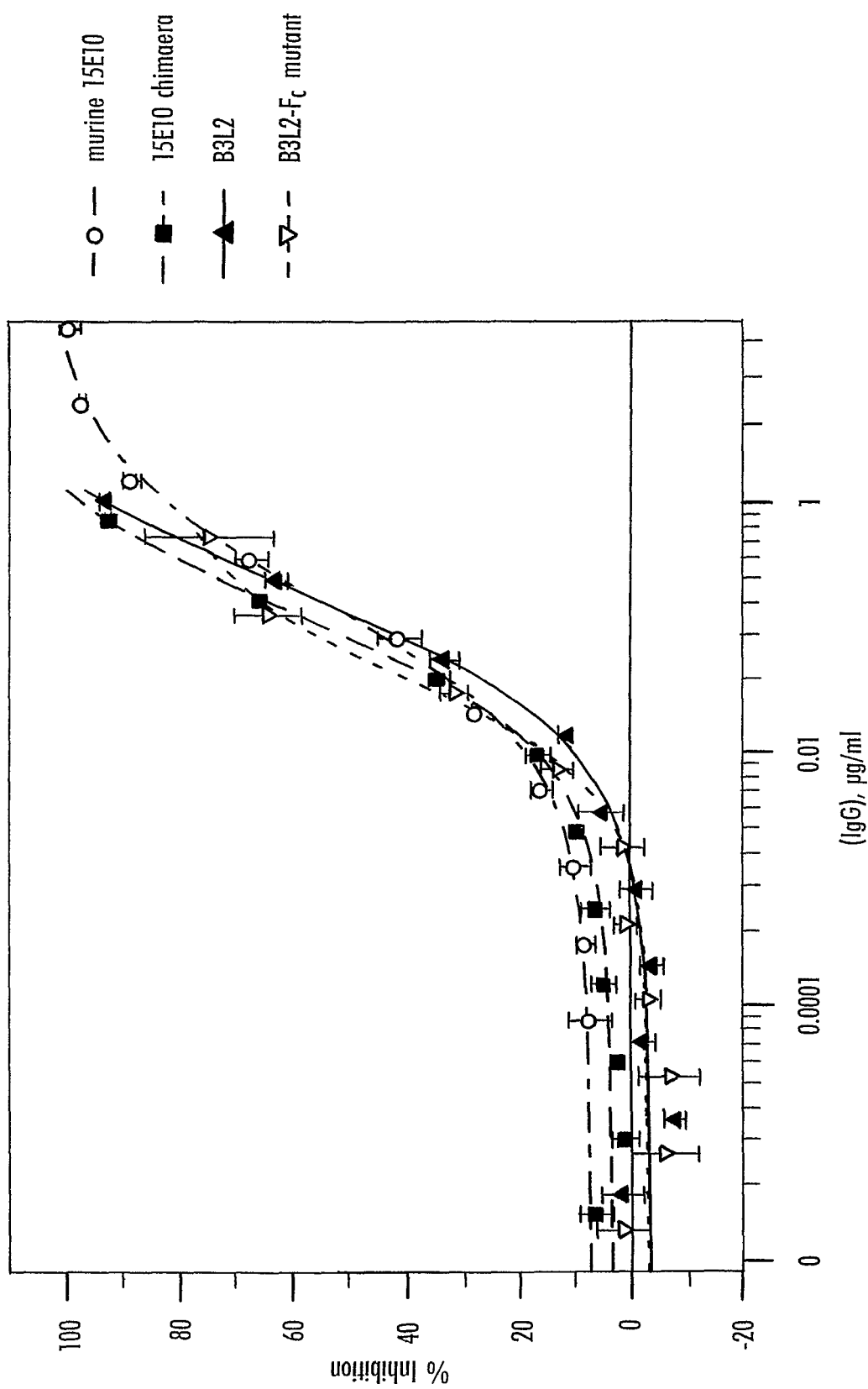
FIG. 19 illustrates the KB cell assay of the parent murine 15E10, 15E10 chimaera, humanised construct B3L2 and a Fc lytic mutant of B3L2 against CHO produced hOSM.

A humanised B3L2 antibody carrying 2 point mutations in the constant heavy chain (Ala replaces Leu at position 235 and Gly at position 237) was designed, expressed in CHO cells and purified. The mutations reduce the ability of the antibody to engage effector functions especially recruitment of complement factors. Humanised antibody candidate B3L2 with intact heavy chain is referred to as B3L2 wt (wild type) while the mutated B3L2 antibody is called B3L2 mut in the FIGS. 17 to 19.

TABLE 4

IC50 values for humanised B3L2 wild type compared
with parent murine and chimaeric antibodies in
the gp130 inhibition ELISA and KB cell assay

|  | gp130 ELISA | KB cell assay |
|---|---|---|
| Murine 15E10 | 0.009 | 0.053 |
| Chimaeric 15E10 | 0.019 | 0.079 |
| B3L2 wt | 0.035 | 0.123 |

IC50 values are in µg/ml

These results confirm that the humanised B3L2 antibody has potency equivalent to the parent murine antibody 15E10.

Amino acid sequence of humanised B3L2 heavy chain is set forth in SEQ. I.D. NO:11 and humanised B3L2 light chain is set forth in SEQ. I.D. NO:12.

Example 7

Antibody 10D3

7.1. Generation of Monoclonal Antibodies

Hybridoma 10D3 was generated as detailed in Example 1 above.

7.2. Cloning of Variable Regions of Clone 10D3

Total RNA was extracted from clone 10D3 hybridoma cells and the cDNA of the heavy and light variable domains was produced by reverse transcription using primers specific for the murine leader sequence and the antibody constant regions according to the pre-determined isotype (IgG1/κ). The cDNA of the variable heavy and light domains was then cloned into vector pCR2.1 for sequencing.

7.2.1 RNA Extraction

Total RNA was extracted from pellets of 106 cells of hybridoma clone 10D3 using the SV Total RNA Isolation System from Promega according to manufacturer's instructions.

7.2.2 Reverse Transcription

RNA was reverse transcribed to produce cDNA of the variable heavy and light domains using primers specific for the murine leader sequences and murine IgGγ2a/κ constant regions. The mixture of primers used is set forth in Jones S T and Bendig M M Bio/technology 9:88-89 (1991)

Pools of murine $V_H$ and $V_L$ leader sequence forward primers were prepared at 50 µM. Solutions of the murine γ2a and κ constant region reverse primers were also prepared at 50 µM.

7.2.3 Reverse Transcription PCR(RT-PCR)

Reverse transcription of the RNA encoding the variable heavy and light regions was carried out in duplicates using the Access RT-PCR System from Promega according to manufacturer's instructions. $V_H$ and $V_L$ forward and reverse primers were as described above.

7.3. Cloning of PCR Product of 7.2.3

7.3.1 Gel Purification

The products of RT-PCR ($2\times V_H$ and $2\times V_L$) were loaded in gel loading solution on a preparative 1% agarose gel containing 0.01% ethidium bromide and run in TAE buffer at 100V for 1 hour and the V region bands excised. A 100 bp DNA ladder was also run on the gel to allow identification of the $V_H$ and $V_L$ bands.

The DNA fragments were extracted and purified from the gel using the QIAquick™ Gel extraction kit from Qiagen according to manufacturer's instructions.

7.3.2 Ligation

The purified RT-PCR fragments ($2\times V_H$ and $2\times V_L$) were cloned into the pCR2.1 vector using the TA cloning kit from Invitrogen according to manufacturer's instructions.

7.3.3 Transformation

Ligated plasmids were transformed into TOP10F' cells according to TA cloning kit instructions. 50 µl and 200 µl of transformed cells were spread on L-agar plates containing 100 µg/ml ampicillin and coated with 8 µl of 500 mM IPTG solution and 16 µl of 50 mg/ml X-Gal solution in DMF. Plates were incubated overnight at 37° C.

7.3.4 Sequencing 5 white colonies were cultured overnight at 37° C. in 5 ml LB medium supplemented with 100 µg/ml ampicillin.

pCR2.1 plasmids containing 10D3 $V_H$ and $V_L$ domains were extracted and purified using the Qiagen QIAprep Spin Miniprep kit according to manufacturer's instructions.

The $V_H$ and $V_L$ domains were sequenced using primers T7, M13 for and M13 rev.

10D3 $V_H$ domain amino acid sequence (consensus of 10 clones from 2 RT-PCR reactions): SEQ. I.D. NO:46

10D3 $V_L$ domain amino acid sequence (consensus of 10 clones from 2 RT-PCR reactions): SEQ. I.D. NO:47

7.4. Chimaeric Antibody

A chimaeric antibody consisting of parent murine V regions of 7.3.4 grafted onto human IgG1/k wild type C regions was designed to confirm the cloning of the correct murine V regions and also to be used as a reference when testing humanised constructs. The chimaeric antibody was expressed in CHO cells, purified and tested for affinity to OSM site II in the gp130 inhibition ELISA and KB cell assay.

The cloned murine V regions were amplified by PCR to introduce restriction sites required for cloning into mammalian expression vectors Rld and Rln. Hind III and Spe I sites were designed to frame the $V_H$ domain and allow cloning into a modified Rld vector containing the human γ1 wild type C region. Hind III and BsiW I sites were designed to frame the $V_L$ domain and allow cloning into a modified Rln vector containing the human κC region.

7.4.1 PCR Amplification $V_H$ forward primer:

The Hind III restriction site is underlined and Kozak sequence in bold.

$V_H$ forward:
(SEQ.I.D.NO:58)
5'-GAT <u>GAA GCT T</u>GC CAC CAT GGG ATG GAG CTG GGT CTT T-3'

$V_H$ reverse:
(SEQ.I.D.NO;65)
5'-GAT GG<u>A CTA GTG</u> TGC CTT GGC CCC AAT A-3'

The Spe I restriction site is underlined.

$V_L$ forward primer:
$V_L$ forward:
(SEQ.I.D.NO:59)
5'-GAT <u>GAA GCT T</u>GC CAC CAT GGA TTT ACA GGT GCA GAT T-3'

The Hind III restriction site is underlined and Kozak sequence in bold.

```
V_L reverse:
                                    (SEQ.I.D.NO:60)
5'-GAT GCG TAC GTT TCA GCT CCA GCT TGG TCC C-3'
```

The BsiW I restriction site is underlined

| PCR reaction: | water | 66 µl |
|---|---|---|
| | 10× PCR buffer | 10 µl |
| | dNTP (2 mM) | 10 µl |
| | primer 1 (5 µM) | 4 µl |
| | primer 2 (5 µM) | 4 µl |
| | AmpliTaq polymerase | 2 µl |
| | purified plasmid | 4 µl |
| | total vol | 100 µl |

Primer 1: $V_H$ or $V_L$ forward primer

Primer 2: $V_H$ or $V_L$ reverse primer

Purified plasmid: pCR2.1 $V_H$ or $V_L$ plasmid purified by Qiagen Minipreps (diluted 200×)

| PCR cycle: | 1- 95° C. for 4 min |
|---|---|
| | 2- 95° C. for 1 min |
| | 3- 55° C. for 1 min |
| | 5- 72° C. for 7 min |
| | steps 2 to 4: were repeated 30 times |

7.4.2 Cloning into Mammalian Expression Vectors

The PCR products were purified using the MinElute PCR Purification kit from Qiagen according to manufacturer's instructions.

7.4.2.1 Restriction Digests

The $V_H$ PCR product and Rld hCγ1wt mammalian expression vector were digested Hind III-Spe I:

| 10× buffer (NEBuffer2) | 5 µl |
|---|---|
| BSA 100× (NEB) | 0.5 µl |
| DNA | 5 µl |
| Hind III (Promega) | 2 µl |
| Spe I (NEB) | 2 µl |
| water | 35.5 µl |
| total vol | 50 µl |

DNA: purified $V_H$ PCR product or Rld hCγ1 wt vector (at 0.25 mg/ml) Incubated at 2 h at 37° C.

The $V_L$ PCR product and Rln hCκ mammalian expression vector were digested Hind III-BsiW I:

| 10× buffer (NEBuffer2) | 5 µl |
|---|---|
| DNA | 5 µl |
| Hind III (Promega) | 2 µl |
| water | 38 µl |
| total vol | 50 µl |

DNA: purified $V_L$ PCR product or Rln hCκ vector (at 0.25 mg/ml) Incubated at 2 h at 37° C.

2 µl of BsiW I (NEB) was added and incubated 2 h at 55° C.

7.4.2.2 Gel Purification

The products of restriction digests were loaded in gel loading solution on a preparative 1% agarose gel containing 0.01% ethidium bromide and run in TAE buffer at 100V for 1 hour and the Rld and Rln vector as well as $V_H$ and $V_L$ PCR fragment bands were excised. A 100 bp DNA ladder was also run on the gel to allow identification of the $V_H$, $V_L$ and vector bands.

The DNA was extracted and purified from the gel using the QIAquick Gel extraction kit from Qiagen according to manufacturer's instructions.

7.4.2.3 Ligation

The $V_H$ PCR fragment Hind III-Spe I digested was ligated into the Rld hCγ1wt vector Hind III-Spe I digested.

The $V_L$ PCR fragment Hind III-BsiW I digested was ligated into the Rln hCκ vector Hind III-BsiW I digested.

The ligation was carried out using the LigaFast Rapid DNA Ligation System from Promega according to manufacturer's instructions providing:

| $V_H$: | vector: Rld hCγ1wt Hind III-Spe I digested |
|---|---|
| | insert: $V_H$ PCR fragment Hind III-Spe I digested |
| $V_L$: | vector: Rln hC$_k$ Hind III-BsiW I digested |
| | insert: $V_L$ PCR fragment Hind III-BsiW I digested |

7.4.2.4 Transformation

Ligated products were transformed into DH5a competent cells:

200 µl DH5α vials were thawed on ice.

50 µl aliquots were prepared in transformation tubes.

2 µl of ligation mixture was added and mixed gently with a pipette tip followed by incubation for 30 min on ice.

The mixture was incubated for 45 sec at 42° C. without shaking.

This was then transferred to ice for 2 min.

450 µl SOC medium was added and the tubes incubated for 1 h at 37° C. on shaker incubator.

100 µl of culture was spread on L-agar plates supplemented with 100 µg/ml ampicillin and incubated overnight at 37° C.

7.4.2.5 Sequencing $V_H$ and $V_L$ clones were cultured overnight at 37° C. in 5 ml LB medium supplemented with 100 µg/ml ampicillin.

Rld and Rln plasmids containing $V_H$ and $V_L$ domains respectively were extracted and purified using the QIAprep Spin Miniprep kit from Qiagen according to manufacturer's instructions.

The $V_H$ region was sequenced using forward primers in the Rld vector and signal sequence and reverse primer in the human Cγ1 region.

The $V_L$ region was sequenced using forward primers in the Rln vector and signal sequence and reverse primer in the human Cκ region.

Clones with the correct $V_H$ and $V_L$ sequences were identified and plasmids prepared for expression in CHO cells.

7.4.3 Chimaeric Antibody Expression in CHO Cells

Rld and Rln plasmids containing 10D3 $V_H$ and $V_L$ domains respectively were transiently co-transfected into CHO cells and expressed. The chimaeric antibody produced was purified from cell culture supernatant by affinity chromatography on rprotein A Sepharose and its affinity for OSM was evaluated in the gp130 inhibition ELISA and KB cell assay (see below).

7.4.3.1 Plasmid Purification

DH5α cells containing Rld-10D3$V_H$ and Rln-10D3$V_L$ plasmids were cultured in 5 ml of LB media supplemented with 100 μg/ml ampicillin for 8 h at 37° C. in a shaker incubator.

200 ml of LB media supplemented with 100 μg/ml ampicillin was inoculated with 1 ml of day culture and incubated overnight at 37° C. in a shaker incubator.

The plasmids were extracted and purified using the QIAfilter Plasmid Maxi kit from Qiagen according to manufacturer's instructions. The ethanol pellet was resuspended in 200 μl TE buffer and plasmid concentration was measured by absorbance at 260 nm after 100-fold dilution of stock solution.

7.4.3.2 Transfection

CHO cells were cultured to confluence in Dulbecco's MEM with Glutamax-1 (DMEM) media supplemented with Ultra Low Fetal Bovine Serum and 1% Penicillin-Streptomycin in 4×175 cm² BD Falcon tissue culture flasks at 37° C.

For each flask, in a 50 ml Falcon tube, the following were added and mixed:

8 ml Optimem 1 with Glutamax-1
20 μg Rld-10D3$V_H$ purified plasmid
20 μg Rln-10D3$V_L$ purified plasmid
240 μl TransFast Transfection Reagent under vortex The mixture was incubated for 10-15 min at RT.
DMEM media was removed from flask then the mixture was vortexed and added to flask.
The mixture was incubated at 37° C. for 1 h.
32 ml Optimem was added to the flask and incubated at 37° C. for 48-72 h.

7.4.3.3 Purification of Chimaeric Antibody

Media from all 175 cm² flasks were pooled and centrifuged at 150° C.) rpm for 3 min on an MSE Mistral 2000 and supernatant passed through a 500 mL Filter System 0.22 μm CA.

The antibody was purified from clarified supernatant on an Amersham Biosciences Akta Explorer using Unicorn software.

The column used was a 1 ml HiTrap rProtein A Sepharose FF.

The flow rate was 1 ml/min.
The column was equilibrated with 10 CV of Dulbecco's PBS then loaded with clarified supernatant through pump A.
The column was washed with 20 CV of Dulbecco's PBS, pump A % was washed to waste and a further 10 CV of Dulbecco's PBS was passed through the column to ensure complete clearance of supernatant.

The antibody was eluted with 10 CV of ImmunoPure IgG Elution Buffer (Pierce) and collected in 1 ml fractions containing 100 μl of 1M Trizma-HCl pH8.0 neutralisation buffer.

The column was re-equilibrated with 5 CV of Dulbecco's PBS.

Antibody in eluate fractions was quantified by reading the absorbance at 280 nm against a blank solution containing 10 volumes of ImmunoPure IgG Elution Buffer+1 volume of 1M Trizma-HCl pH8.0 and fractions with sufficient amounts of pure antibody were pooled and stored in 100 μl aliquots at −20° C.

7.4.4 Analysis of Chimaeric Antibody

The 10D3 chimaeric antibody was analysed in the gp130 inhibition ELISA and KB cell assay (see below) for their potency in neutralising both human and cynomolgus OSM.

Protocols for the gp130 inhibition ELISA and KB cell assay are set forth below.

10D3 chimaeric antibodies neutralise OSM in the gp130 inhibition ELISA and KB cell assay These results confirm that the correct variable regions have been cloned successfully to produce an antigen binding chimaeric antibody capable of binding both human and cynomolgus OSM site II.

The 10D3 variable heavy and light domains can now be humanised.

The murine variable regions were cloned and sequenced then grafted onto human γ1/k constant regions to produce a chimeric antibody. The chimeric 10D3 antibody showed potency against human and cynomolgus OSM equivalent to that of the parent murine antibody in the gp130 ELISA and KB cell assays (see below).

The murine antibody was humanised using the "best fit" strategy. For the variable heavy domain, a sequence with 65% identity was selected and the murine CDRs grafted onto the human frameworks. A number of constructs were designed with various backmutations in the frameworks to recover affinity. These constructs are:

| Construct | Backmutations |
|---|---|
| A | T28I |
| B | T28I, R71V, T73K |
| C | T28I, V67A, M69L, R71V, T73K |
| D | T28I, M48I, G44K, V67A, M69L, R71V, T73K |

For the variable light domain, a sequence with 60.0% identity was selected and the murine CDRs grafted onto the human frameworks. A number of constructs were designed with various backmutations in the frameworks to recover affinity. These constructs are:

| Construct | Backmutations |
|---|---|
| LA | none (straight graft) |
| LB | L46R, L47W |
| LC | Y36F, Q38K |
| LD | Y36F, Q38K, L46R, L47W |
| LE | Y36F, Q38K, L46R, L47W, F71Y |

Only the least and most backmutated constructs (A, D, LA, LE) were synthesised by build up of overlapping oligos. Four humanised antibody combinations (ALA, ALE, DLA, DLE) were expressed at small scale in CHO cells and the supernatant analysed for antibody affinity in the gp130 ELISA.

Only humanised antibodies ALE and DLE showed inhibition in the gp130 ELISA but the inhibition by ALE was not sufficient because of the low concentration of antibody in the supernatant so DLE was selected. Production of humanised antibody DLE was scaled up in CHO cells and the antibody purified and analysed in the gp130 ELISA and KB cell assay using 10D3 chimeric antibody as control.

IC50 values (gp130 ELISA) (µg/ml):

|  | hOSM | cOSM |
|---|---|---|
| chimera | 0.032 | 0.246 |
| DLE | 0.021 | 0.059 |

Humanised antibody 10D3 DLE is at least as potent if not more potent than the chimeric antibody against human OSM and cynomolgus OSM in the gp130 ELISA.

Humanised 10D3 DLE and 10D3 chimeric antibodies were analysed in the KB cell assay. 10D3 DLE gave IC50 values of 0.205 µg/ml against human OSM and 0.07 µg/ml against cynomolgus OSM.

In conclusion, anti-human OSM site II antibody 10D3 has been successfully humanised and shows potency equivalent to that of the parent murine antibody.

Materials

SV Total RNA Isolation System: Promega Z3100

Access RT-PCR System: Promega A1250

QIAquick Gel Extraction kit: Qiagen 28704

Gel loading solution: Sigma G7654

Agarose: Invitrogen 15510-019

Ethidium bromide: Sigma E1510

TAE buffer: in-house 100 bp DNA ladder: New England BioLabs N3231S

TA cloning kit: Invitrogen 45-0046

TOP10F' cells: Invitrogen 44-0300

L-agar+100 µg/ml ampicillin: in-house

X-Gal, 50 mg/ml in DMF: Promega V394A

AmpliTaq DNA Polymerase: Applied Biosystems

10×PCR buffer: Applied Biosystems

E-Gel 1.2% agarose: Invitrogen G501801

LB medium+100 µg/ml ampicillin: in-house

QIAprep Spin Miniprep kit: Qiagen 27106

MinElute PCR Purification kit: Qiagen 28004

NEBuffer2 10× conc: New England Biolabs B7002S

Purified BSA 100× conc: New England Biolabs B9001S

BsiW I: New England Biolabs R0553L

Hind III: Promega R604A

Spe I: New England Biolabs R0133S

LigaFast Rapid DNA Ligation System: Promega M8225

MAX Efficiency DH5α Chemically Competent cells: Invitrogen 18258-012

SOC media: in-house

QIAfilter Plasmid Maxi kit: Qiagen 12263

Dulbecco's MEM with Glutamax-1: Invitrogen 31966-021

Optimem 1 with Glutamax-1: Invitrogen 51985-026

TransFast Transfection Reagent: Promega E2431

1 ml HiTrap rprotein A Sepharose FF: Amersham Biosciences 17-5079-01

Dulbecco's PBS: Sigma D8537

ImmunoPure IgG Elution Buffer: Pierce 21009

1M Trizma-HCl pH8.0: Sigma T2694

ProofStart DNA Polymerase: Qiagen 1016816

ProofStart PCR buffer: Qiagen 1016961

Example 8 gp130 Inhibition ELISA

OSM binds sequentially to gp130 and either the OSM receptor or LIF receptor. The assay described here allows measurement of OSM (for example hOSM) bound to gp130 on an ELISA plate. In addition, the assay allows the measurement of inhibition of OSM binding to the gp130 receptor by antibodies raised against OSM site II.

8.1 Materials
1. Nunc Immunoplate 1 F96 Maxisorp (Life Technologies, 4-39454A)
2. Human gp130-Fc 100 µg/ml (R&D Systems, 671-GP-100)
3. PBS
4. BSA (Sigma A7030)
5. Human recombinant OSM 10 µg/ml (R&D Systems, non-glycosylated)
6. Biotinylated anti human OSM 50 µg/ml (R&D Systems, BAF295)
7. Streptavidin HRP (Amersham RPN4401)
8. 3,3'5,5'-tetramethylene benzidine (TMB) (Sigma)
9. Sulphuric acid
10. Tween 20 (Sigma P7949)

8.2 Preparation of Reagents
1. Preparation of plates: Dilute the human gp130-Fc to 1 µg/ml in PBS. Add 50 µl/well, cover and incubate overnight at 4° C.
2. Wash buffer: to 1 L PBS add 500 µl Tween 20 (0.05%)
3. Blocking buffer: to 500 ml PBS add 5 g BSA (1%)

8.3 Method
1. Wash plate using standard plate washer protocol and tap dry.
2. Add 200 µl/well blocking buffer and incubate for 1 hour at RT.
3. Wash as in step 1.
4. Add 50 µl/well OSM standard or sample. Cover and agitate for 2 hours at RT.
   (OSM is diluted to 100, 50, 25, 12.5, 6.25, 3.125, 1.563 and 0 ng/ml in blocking buffer or tissue culture medium depending on the sample)
5. Wash as in step 1.
6. Add 50 µl/well biotinylated anti human OSM diluted to 30 ng/ml in blocking buffer. Cover and agitate for 1 hour at RT.
7. Wash as in step 1.
8. Add 50 µl/well streptavidin HRP diluted 1/4000 in blocking buffer. Cover and agitate for 30 min. at RT.
9. Wash as in step 1.
10. Add 100 µl/well TMB substrate. Cover and agitate for 30 minutes at room temperature.
11. Add 50 µl/well 1M $H_2SO_4$.
12. Read OD $450_{nm}$.

8.4 Use of Assay for Analysis of Antibody Mediated Inhibition of gp130-OSM Binding.

1) Mix 25 ng/ml OSM with various concentrations of anti-OSM antibody, or various dilutions of antisera containing OSM antibodies. Incubate for 1 h at RT.
2) Add 50 µl/well of the antibody-OSM mixture to a 96 well plate containing bound gp130, prepared as above.
3) Proceed with assay as described above.

9. KB Assay

Introduction

KB cells (a human epithelial cell line) express mRNA for gp130 together with LIF and OSM receptors (Mosley, J. Biol. Chem., 271 (50) 32635-32643). Both OSM and LIF induce IL-6 release from KB cells. This cell line has been used to identify monoclonal antibodies modulating the interaction between OSM and gp130.

9.1 Method

KB cells were obtained from ECACC (Accession no 94050408) and maintained in DMEM+10% heat inactivated FCS, supplemented with glutamine ("KB medium"). Cells grow as a monolayer and were split twice weekly. Sigma non-enzymatic cell dissociation medium or Versene was used to detach the cells.

1. Add $2 \times 10^4$ cells/100 µl/well/96 well plate and incubate overnight (37° C., 5% $CO_2$).
2. Make up OSM standards in culture media
3. Make up 1 ng/ml OSM+antibody/sera dilutions. Incubate for 1 h at RT.
4. Carefully remove media from KB cell plate and add OSM standards and OSM-antibody mixtures.
5. Incubate for ~16-18 h at 37° C.
6. Remove culture medium and assay for IL-6.

Note:
Culture medium can be kept frozen until ready for analysis.
Culture medium should be diluted ~20 fold for assay.
In screening hybridomas, the ratio of cloning medium to KB medium should be constant, and the OSM standards should be made up in this mixture.
Stimulation of KB cells with ~100 ng/ml OSM gives maximal IL-6 output, but 1 ng/ml is sufficient to look for antibody neutralising activity.

10. Competition Assay.

Figure 20:
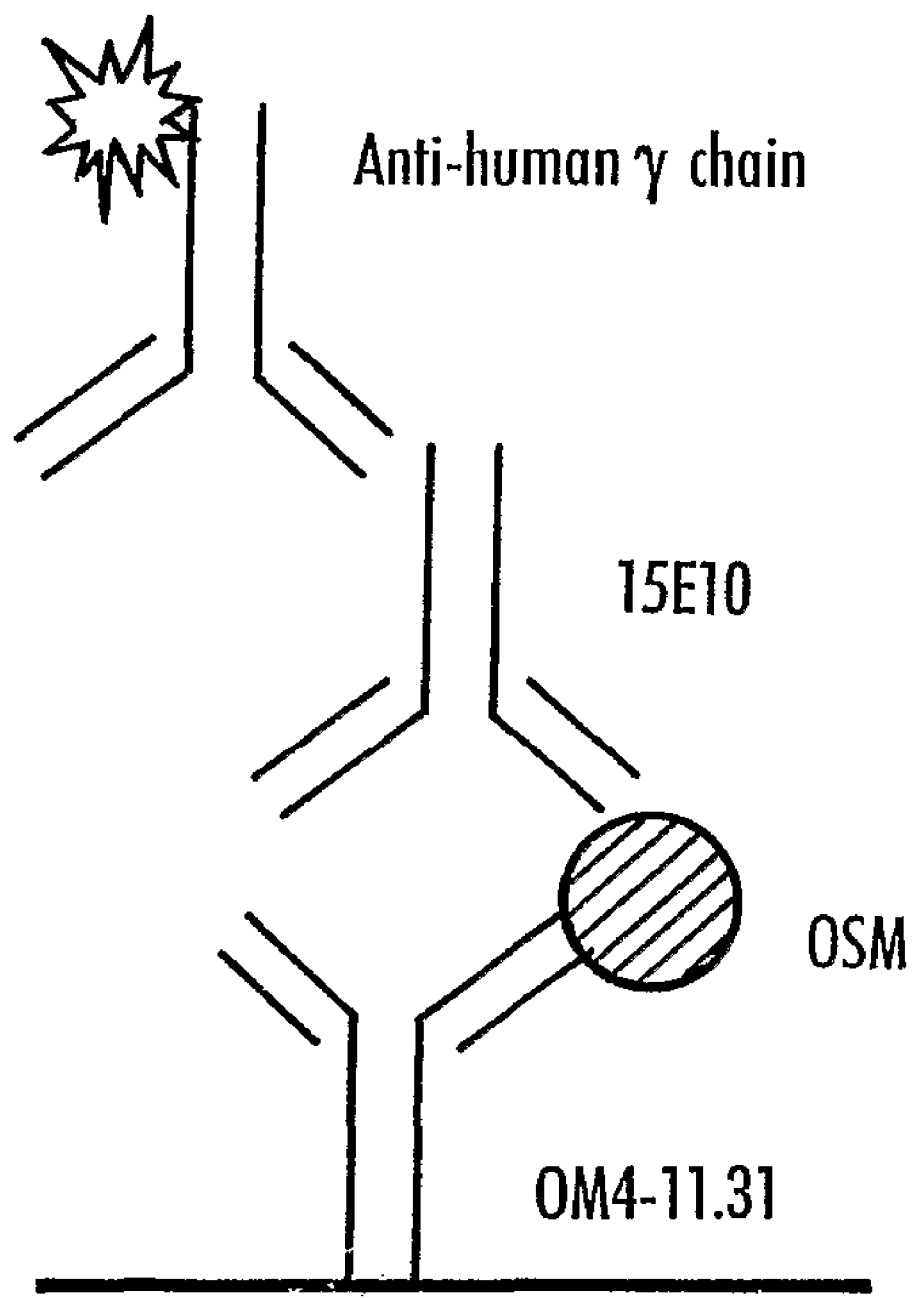
FIG. 20 is a schematic illustration of the competition assay of the examples.

This assay allows the measurement of inhibition of binding of the humanised antibody having a heavy chain of SEQ. I.D. NO: 11 and a light chain having a light chain of SEQ. I.D. NO: 12 (for the purpose of this example denoted as 15E10-B3L2) to soluble glycosylated hOSM by a candidate non-human antibody that specifically binds to Site II of hOSM. A schematic illustration of the assay of this example is set forth in FIG. 20.

The plate is coated with anti-site III monoclonal antibody (referred to herein as OM4-11.31).

For the standard curve: 15E10-B3L2 purified standard serially diluted from 1 µg/ml is incubated with soluble glycosylated human OSM at 50 ng/ml. The antibody binds to OSM through site II and the complex is then captured on the plate by the primary antibody against site III.

For the competition assay: the candidate antibody serially diluted from 1 µg/ml is incubated with soluble glycosylated human OSM at 50 ng/ml and 15E10-B3L2 at 150 ng/ml.

The presence of complexed 15E10-B3L2 is detected by an anti-human gamma chain secondary antibody.

Method:

1/ Coating
A Nunc Maxisorp Immunoplate was coated with 50 µl per well of anti-human OSM site III antibody (OM4-11.31, in-house) at 4 µg/ml in PBS. The plate was incubated overnight at 4° C.

2/ Blocking
The plate was washed 3 times with PBS+0.05% Tween (PBST). 100 µl of 1% BSA (Sigma A7030) in PBS was added to each well.
The plate was incubated at room temperature for 2 h with shaking.

3/ Pre-Incubation

15E10B3L2 Standard:
A solution of 15E10-B3L2 antibody at 1 µg/ml in 50 ng/ml human OSM in block buffer was prepared and 67 µl added to 2 wells in row A of a non-adsorbent 96-well plate. The antibody was serially diluted 1:3 in 50 µl of 50 ng/ml human OSM in block buffer from row B to G.

Competing Antibody:
A solution of competing antibody at 1 µg/ml in 150 ng/ml 15E10-B3L2+50 ng/ml hOSM in block buffer was prepared and 100 µl added to 2 wells in row A of a non-adsorbent 96-well plate. The antibody was serially diluted 1:1 in 50 µl of 150 ng/ml 15E10-B3L2+50 ng/ml human OSM in block buffer from row B to G. Two wells were incubated with diluent without competing antibody.

The pre-incubation plate was incubated at room temperature for 1 h under static conditions.

4/ Incubation
The coated plate was washed 3 times with PBST.
45 µl of each standard and sample was transferred from the pre-incubation plate to equivalent wells on the coated plate. PBS was added to blank wells.
The plate was incubated at room temperature for 2 h under shaking.

5/ Secondary Antibody
The plate was washed 3 times with PBST.
50 µl of goat anti-human γ chain-peroxidase (Sigma A6029) diluted 2000 fold in block buffer was added to each well.
The plate was incubated at room temperature for 1 h under shaking.

6/ Substrate
The plate was washed 3 times with PBST.
The OPD substrate (Sigma P9187) was prepared in water according to manufacturer's instructions.
50 µl was added to each well.
The plate was incubated at room temperature.

7/ Stop
Once the coloration had sufficiently developed, the chromogenic reaction was stopped by addition of 10 µl of 3M $H_2SO_4$ per well.
The plate was read at 490 nm in a plate reader using blank wells as 0 absorbance.
The standard curve of absorbance at 490 nm against 15E10 concentration was plotted.
The complexed 15E10 concentration in the samples containing competing antibody was read off the standard curve.
% inhibition was calculated as:

$$100 - [(15\text{E}10 \text{ conc in sample in ng/ml} \div 150 \text{ ng/ml}) \times 100]$$

The curve of % inhibition against competing antibody concentration was plotted and the % inhibition of 15E10 at equimolarity of competing antibody (150 ng/ml of competing antibody) was read off the curve.

Example 10.1

10D3 as Competing Antibody

Murine 10D3 clone E9 antibody at 267 µg/ml (stock) was used as the competitor of 15E10. 10D3 has the light and heavy chain CDRs as set forth in Table A above.
Results:

| 10D3 (µg/ml) | Complexed 15E10 (µg/ml) | % inhibition |
|---|---|---|
| 1 | 0.019 | 87.3 |
| 0.5 | 0.029 | 80.7 |
| 0.25 | 0.044 | 70.7 |
| 0.125 | 0.062 | 58.7 |
| 0.062 | 0.092 | 38.7 |
| 0.031 | 0.132 | 12.0 |
| 0.016 | 0.146 | 2.7 |

Figure 21:
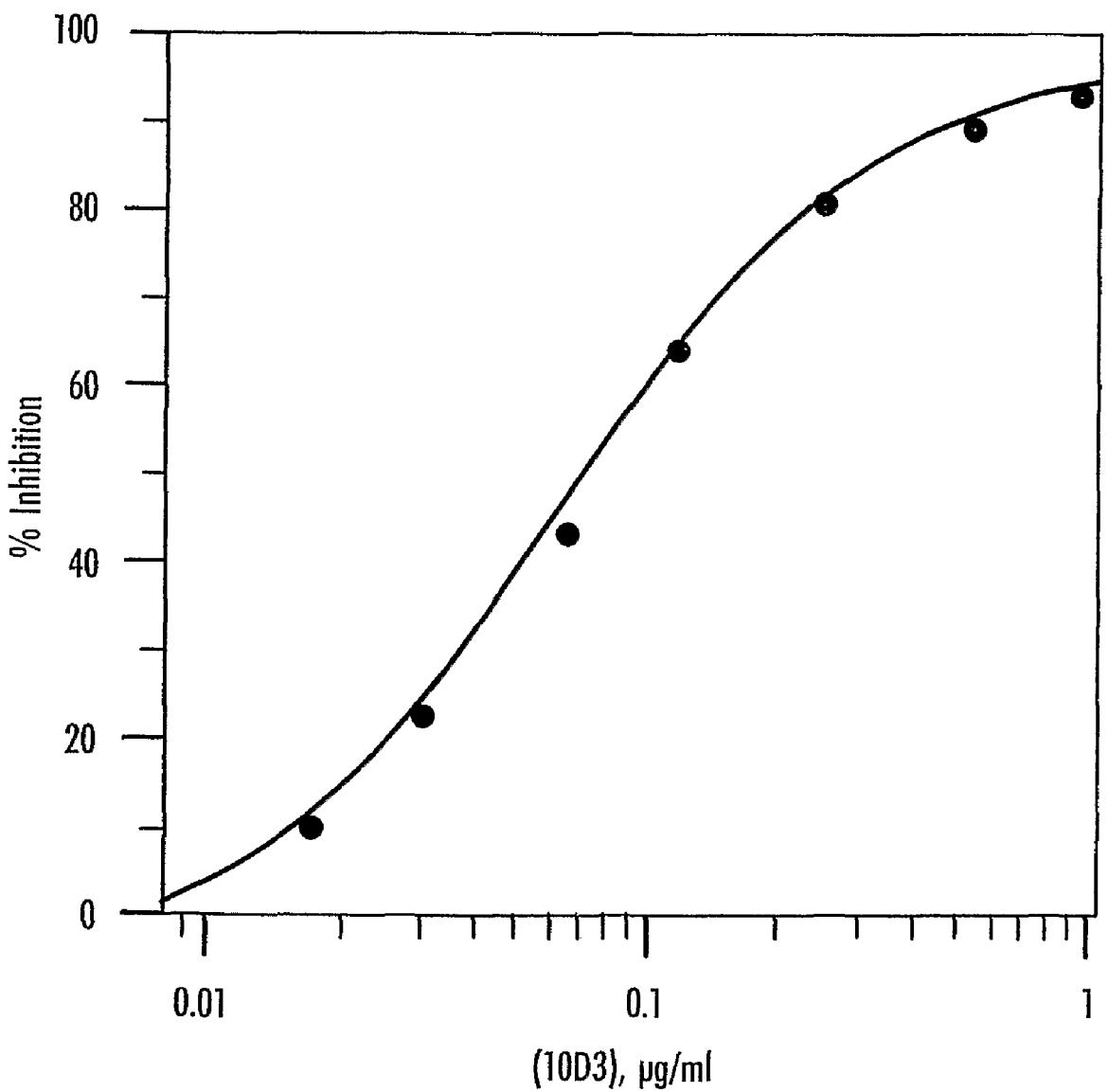
FIG. 21 illustrates the inhibition of 15E10 (B3L2 humanised construct) by murine 10D3 competitor antibody of the examples. The percentage inhibition of 15E10 by 10D3 competitor at equimolarity (0.15 ug/ml):62.3%.

% inhibition of 15E10 by 10D3 competitor at equimolarity (0.15 µg/ml): 62.3%. See FIG. 21.

Example 11

Identification of Antibodies that Bind OSM and are Specific for Site II or Site III of OSM For biological function, OSM has to interact with both gp130 and LIFR or OSMRβ. The initial interaction of OSM with gp130 involves OSM site II, whilst OSM interaction with the OSMRβ or LIFR occurs via site III. It follows that antibodies that target either site II or site III OSM sequences, or epitopes sufficiently near these sites such that antibody binding would occlude these sites, would neutralise OSM activity.

Figure 22:
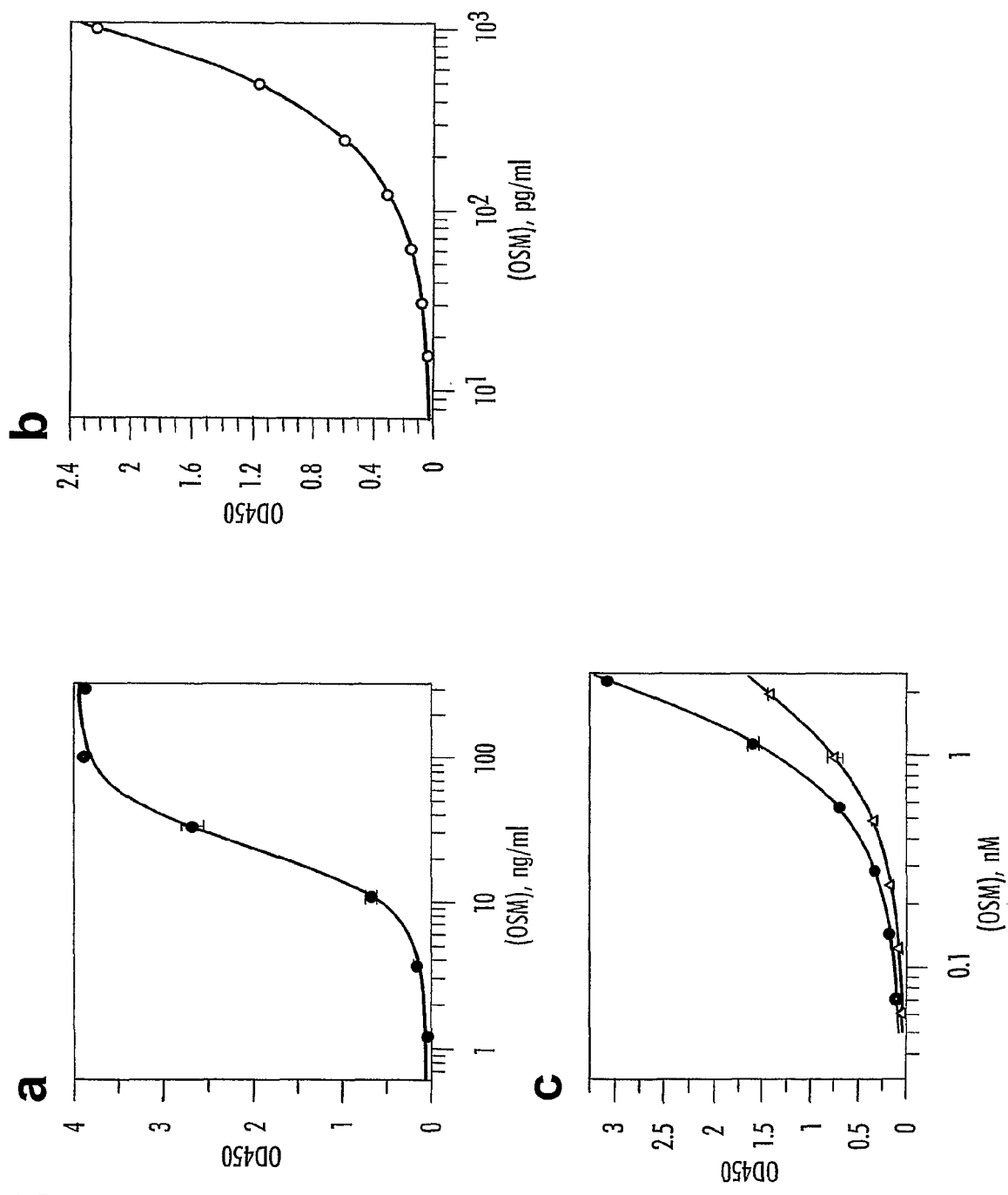
FIG. 22a illustrates a typical standard curve in the gp130-OSMELISA using non-glycosylated OSM. and where the gp130 concentration for coating the ELISA plate is 1 μg/ml.
FIG. 22b illustrates the increased sensitivity of the gp130-OSM ELISA when the gp130 concentration used for coating the plate is increased to 4 μg/ml
FIG. 22c illustrates that the gp130-OSM ELISA works with both glycosylated and non-glycosylated OSM. Non-glycosylated OSM; filled circles, glycosylated OSM; open triangles. Note the sensitivity of the ELISA is greater for non-glycosylated OSM, possibly as a result of glycosylation masking epitopes recognised by the detection antibody used.

An assay for measuring OSM-gp130 binding is set forth in Example 8. A typical standard curve (at 1 µg/ml, gp130) is set forth in FIG. 22.

By changing conditions of the assay (to 4 µg/ml), the sensitivity could be greatly improved as illustrated in FIG. 22b.

Moreover, although the above data was generated using non-glycosylated OSM, glycosylated OSM also binds to gp130 in this assay. See FIG. 22c.

Figure 23:
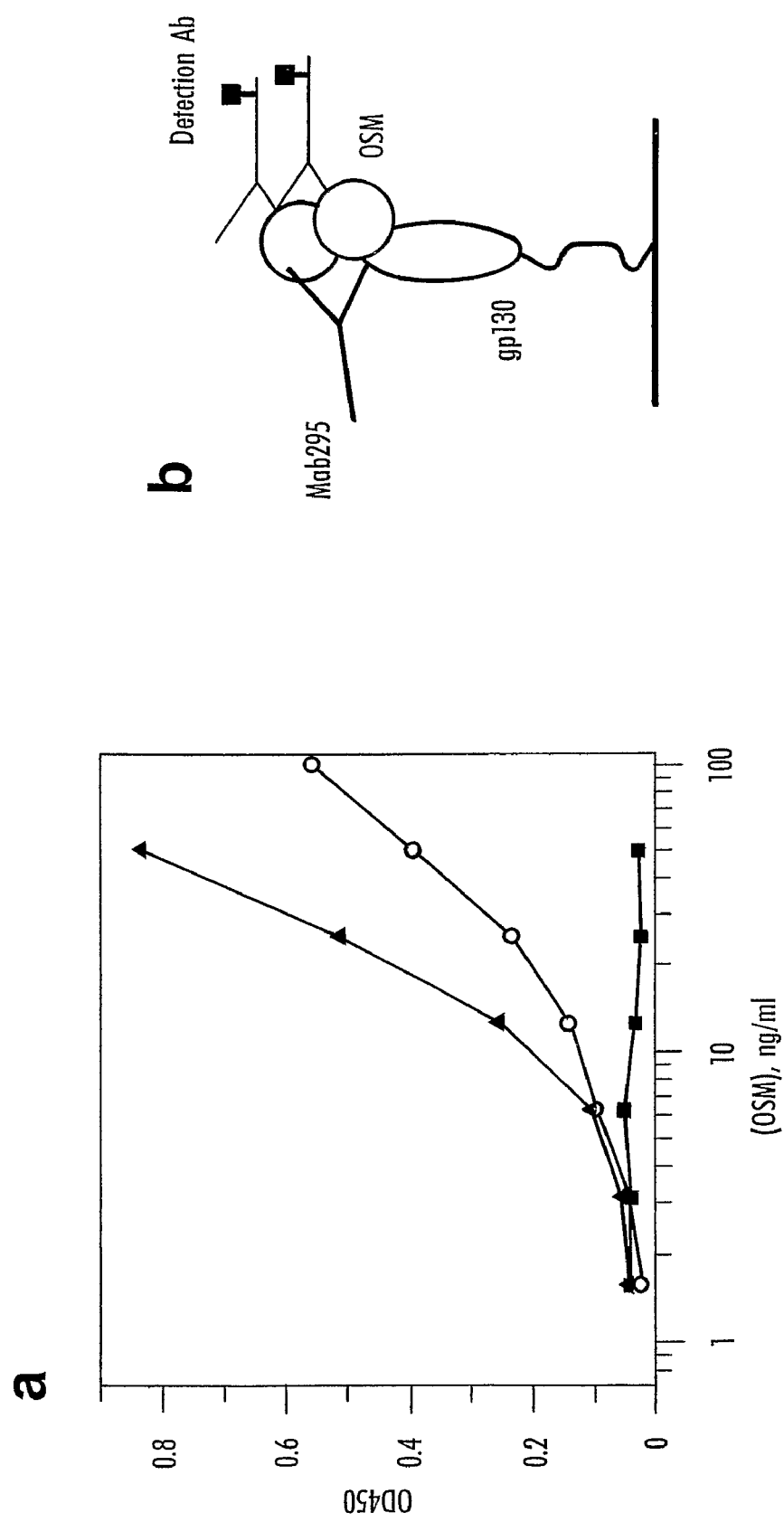
FIG. 23a illustrates the effect of the OSM neutralising antibody, Mab295 (R&D Systems) in the gp130-OSM ELISA. OSM only; open circles, OSM+Mab296; filled triangles, OSM+MAb295 but with no gp130 on the ELISA plate; filled squares.
FIG. 23b is a schematic illustration of how Mab295 might potentiate the OSM signal in the gp130-OSM ELISA.

A commercially available neutralising anti OSM antibody (Mab 295, R&D Systems) was used in this assay to see if it would block OSM-gp130 interaction. Surprisingly, it potentiated the OSM signal, as illustrated in FIG. 23.

Figure 24:
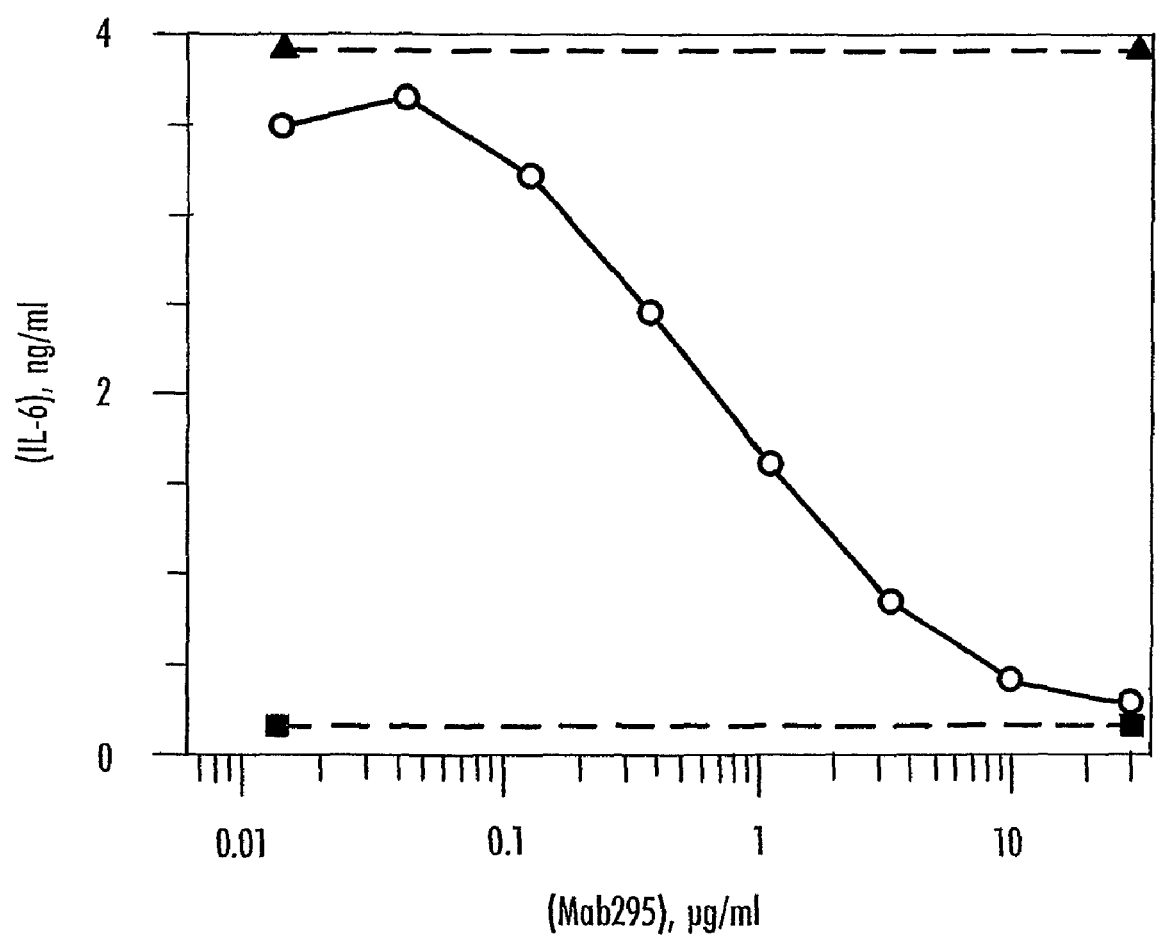
FIG. 24 illustrates data from the KB cell assay showing the effectiveness of OSM neutralisation by Mab 295. Cells were stimulated with 1 ng/ml OSM only, or this concentration of OSM mixed with various concentrations of Mab295 before the assay. OSM only; filled triangles, OSM+Mab295; open circles, no OSM stimulation; filled squares.

When Mab 295 (30 µg/ml) is added to OSM it approximately doubles the OD reading from the ELISA compared with OSM alone for OSM concentrations >10 ng/ml. If gp130 is omitted from the plate, then the signal generated by OSM+ Mab295 is reduced to background. The inventors postulate the following interpretation; Mab295 does not bind to or block OSM site II. At low OSM concentrations, antibody molecules of MAB295 only bind one OSM, which however, is free also to bind to gp130, since site II is available. At higher concentrations, antibody molecules bind two OSM molecules, either of which is available for binding to gp130, thus giving a possible 2 OSM molecules bound for each gp130 molecule, one binding directly to gp130, and the other tethered as a consequence of the bivalent nature of the antibody. It is anticipated that any non-site II OSM antibody would have this effect, but since Mab 295 is a neutralising antibody (see FIG. 24), it must be binding to, or blocking OSM site III. Thus the use of the gp130-OSM ELISA assay of Example 8 and the KB cell assay of example 9 allows identification of neutralising OSM antibodies as site II or site III specific. More particularly a Site III antibody will neutralise OSM in the KB assay but will not neutralise OSM-gp130 binding in the ELISA assay. A Site II antibody will neutralise OSM in both the ELISA and KB assay.

The gp130-OSM ELISA assay was used as a primary hybridoma screen to detect antibodies generated in Example 1 that inhibited gp130-OSM interaction. In addition, hybridomas were also screened for detection of OSM binding activity. Hybridoma supernatants showing high OSM binding, but which did not inhibit OSM-gp130 binding in the ELISA assay of Example 8 were tested in the KB cell assay of Example 9 for OSM neutralisation. This identified a number of site III specific OSM antibodies. One such antibody is referred to as OM4-11.31.

Figure 25:
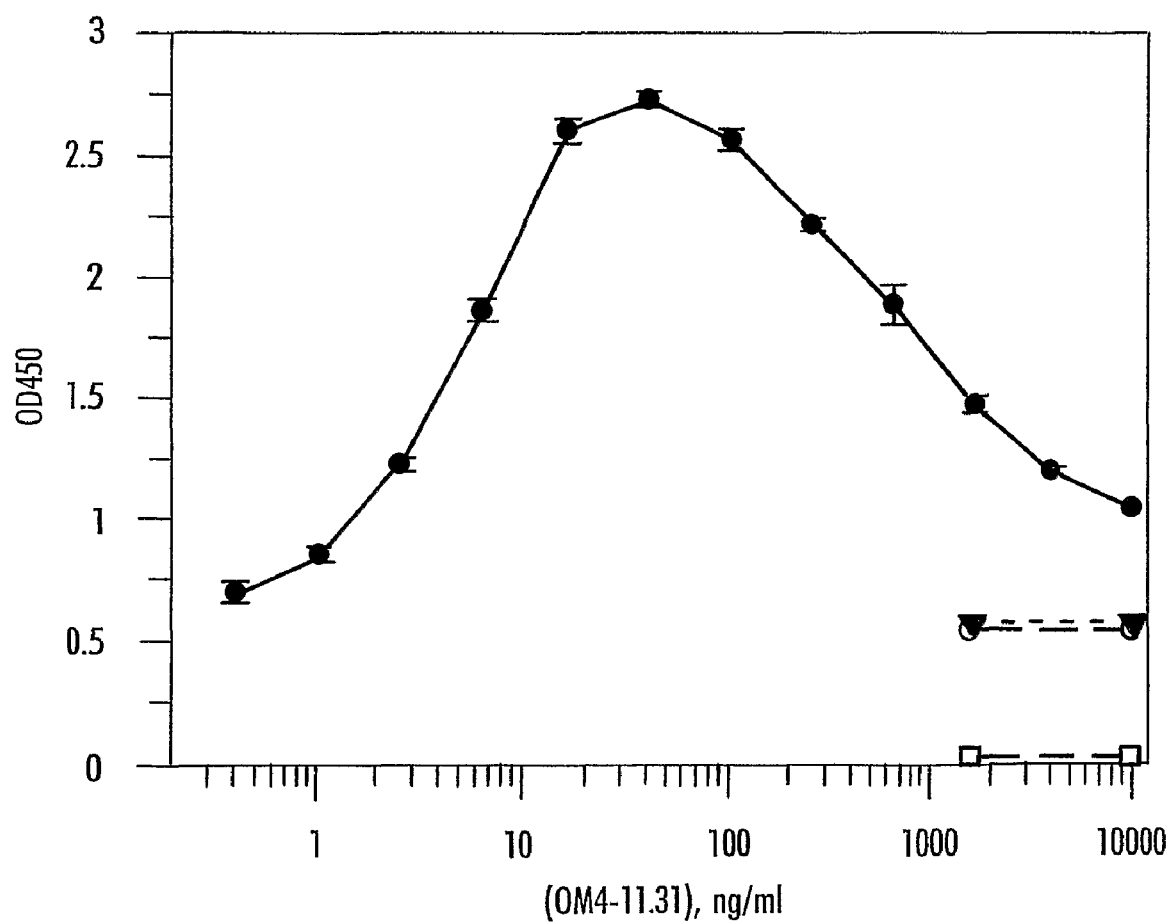
FIG. 25 illustrates the effect of an OSM site III specific antibody, OM4-11.31 in the gp130-OSM ELISA. OSM only; open circles, OSM+Isotype control IgG; Filled inverted triangles, OSM+site II OSM specific antibody; open squares, OSM+OM4-11.31; filled circles.

When site III OSM specific antibodies were used in the gp130-OSM ELISA, they greatly increased the OSM signal as shown in FIG. 25.

The site II antibody, 1B5 (1 µg/ml) completely inhibits OSM-gp130 binding. However, the site III OSM antibody, OM4-11.3.1 causes a biphasic dose-dependent potentiation of OSM binding. At the highest OM4-11.3.1 concentration used the signal is approximately double the OSM only signal, but as antibody concentrations decrease, the signal increases, presumably as a result of formation of antibody-OSM complexes that can bind to gp130, until a peak value is reached. The isotype control IgG for OM4-11.31 had no effect on OSM-gp130 binding. FIG. 25 demonstrates the great sensitivity of this ELISA in discriminating site II vs. non-site II specific antibodies, since the former inhibits, but the latter enhances OSM binding.

Example 11.1

Figure 26:
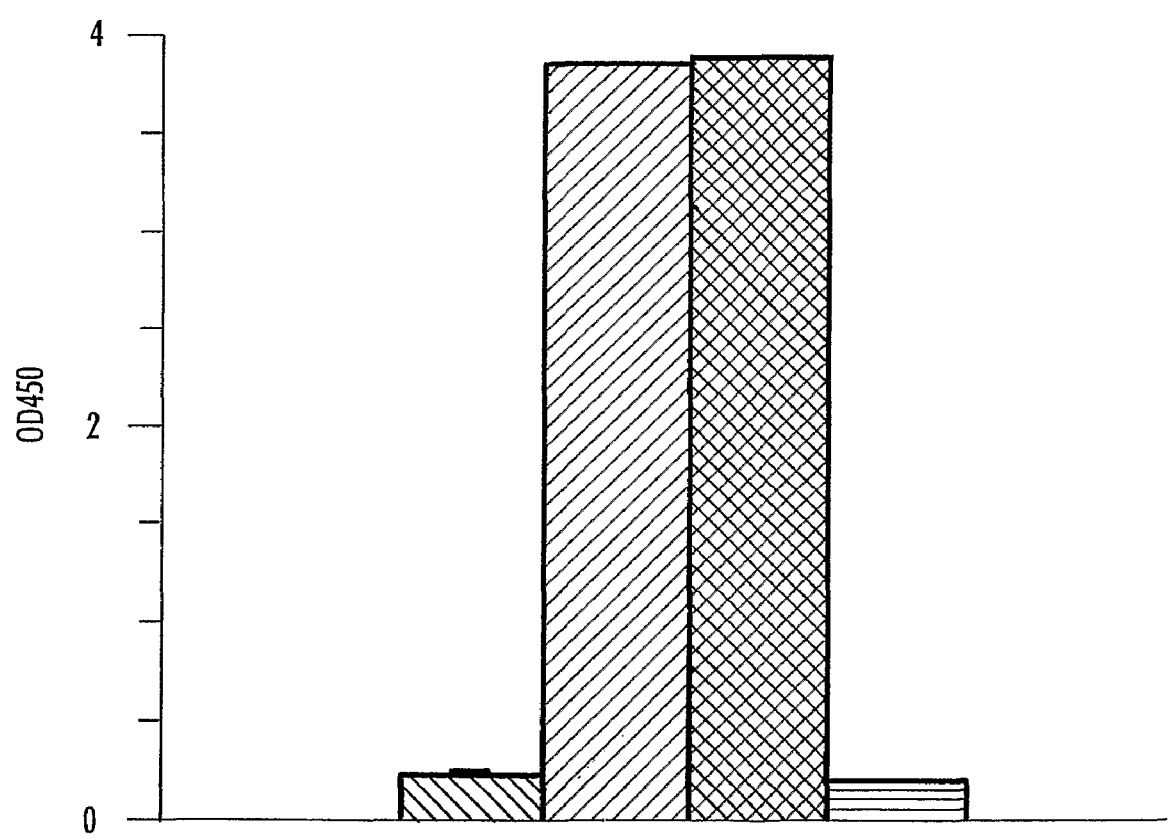
FIG. 26 illustrates the inhibition of binding of a complex of OSM with a site III specific antibody (OM4-11.17) to go130 by a site II specific OSM antibody, OM4-5.3. 12.5 ng/ml OSM only; solid bar, OSM+OM4-11.17; diagonal line bar, OSM+OM4-11.17+control IgG; cross hatched bar; OSM+OM4-11.17+OM4-5.3; stippled bar.

Effect of Site II and Site III Specific Anti-OSM Antibodies in ELISA OSM-gp130 Assay When site II and site III OSM specific antibodies are mixed together, the site II antibodies have a dominant effect in the gp130-OSM ELISA of example 8, as shown in FIG. 26.

The OSM only signal is greatly enhanced by the site III specific OSM antibody OM4-11.17. Whilst this enhancement is unaffected by addition of a control IgG, addition of the site II specific OSM antibody, OM4-5.3, greatly reduces the signal. It is believed that the small detectable signal in the far right column of FIG. 26 is due to a sub-optimal incubation time for the Site II mAb and Site III-OSM complex prior to addition to the gp130 plate.

Figure 27:
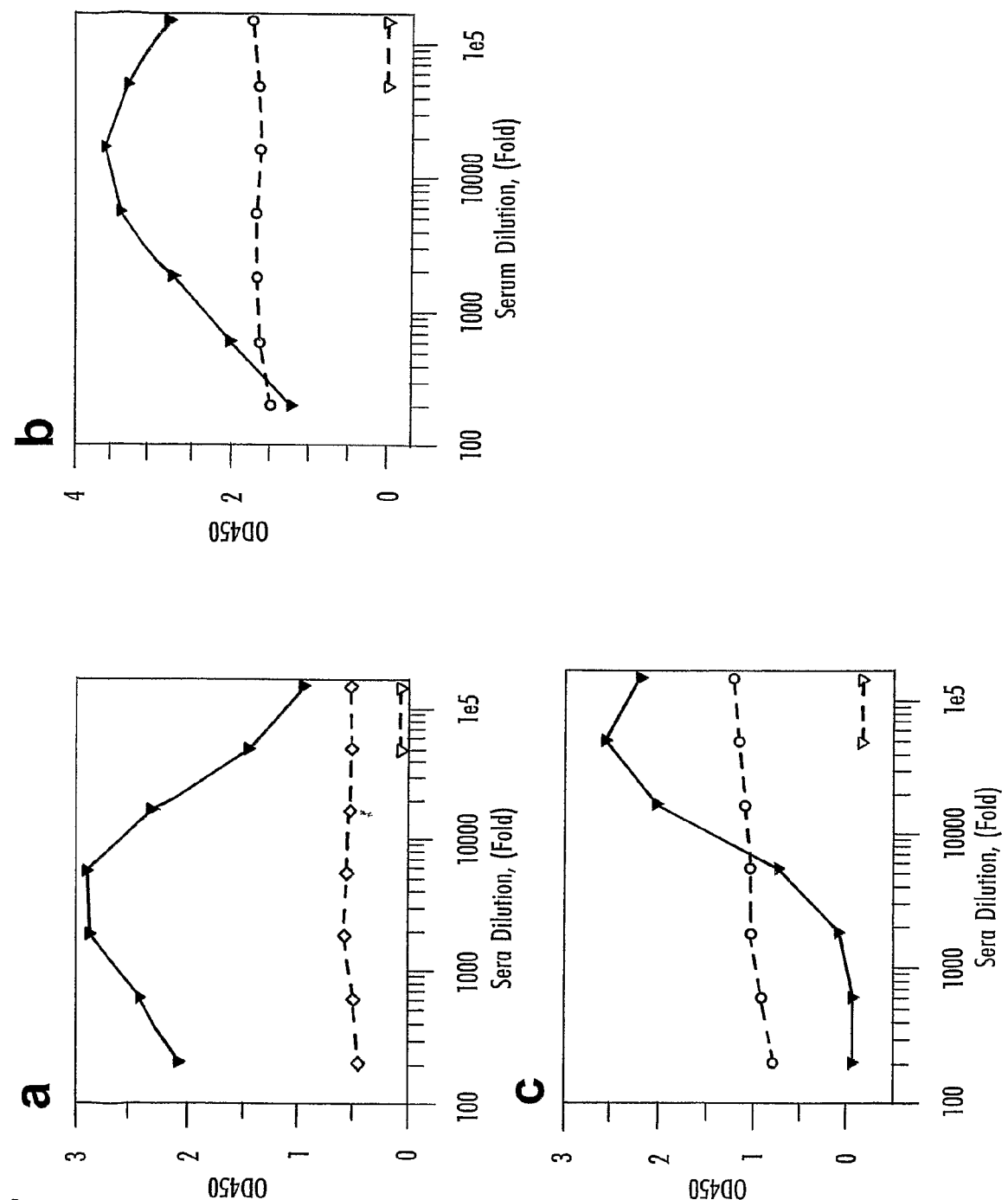
FIG. 27 illustrates the emergence of site II and non-site II specific OSM antibodies in sera of mice immunised with human OSM, as detected using the gp130-OSM ELISA. Analysis of sera after first, second and third boosts with human OSM; a, b and c respectively. OSM+pre-immune serum; open circles, OSM+antisera from immunised mouse; filled inverted triangles, OSM+antiserum from immunised mouse, but without gp130 on ELISA plate; inverted open triangle.

The gp130-OSM ELISA allows monitoring of the emergence of site II specific OSM antibodies in antisera of mice immunised with human OSM (see example 1), as illustrated in FIGS. 27a, 27b and 27c.

After the first boost, predominantly non-site II antibodies were generated, but site II specific antibodies began to emerge after the second boost, and after the third boost, the dominance of the site II antibodies is clearly seen at the higher serum concentrations.

Example 11.2

Synergy Between OSM Site II and Site III Specific Antibodies for OSM Neutralisation Since OSM site II and site III are essential for OSM function, a combination of antibodies that target both sites may operate synergistically in OSM neutralisation. OSM site III is used not only for interaction with OSMRβ and LIFR but also in the binding of a second OSM molecule to gp130 and this could contribute to the increased potency of site III specific antibodies, compared with those against site II.

Figure 28:
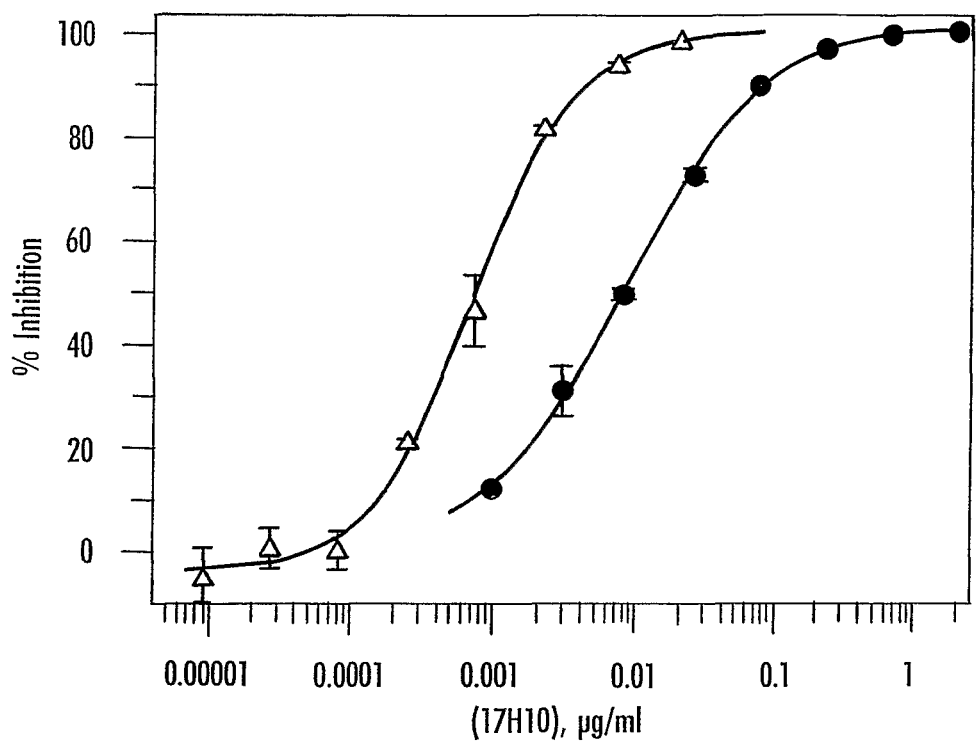
FIG. 28 illustrates the synergy in OSM neutralisation between a site II OSM specific antibody ("hum 15E10", humanised 15E10) and a site III specific OSM antibody, (17H10) as measured in a KB cell assay. OSM neutralisation by 17H10 alone (a) or hum 15E10 alone (b); filled circles, OSM neutralisation by the antibody combination; open triangles
Figure 28:
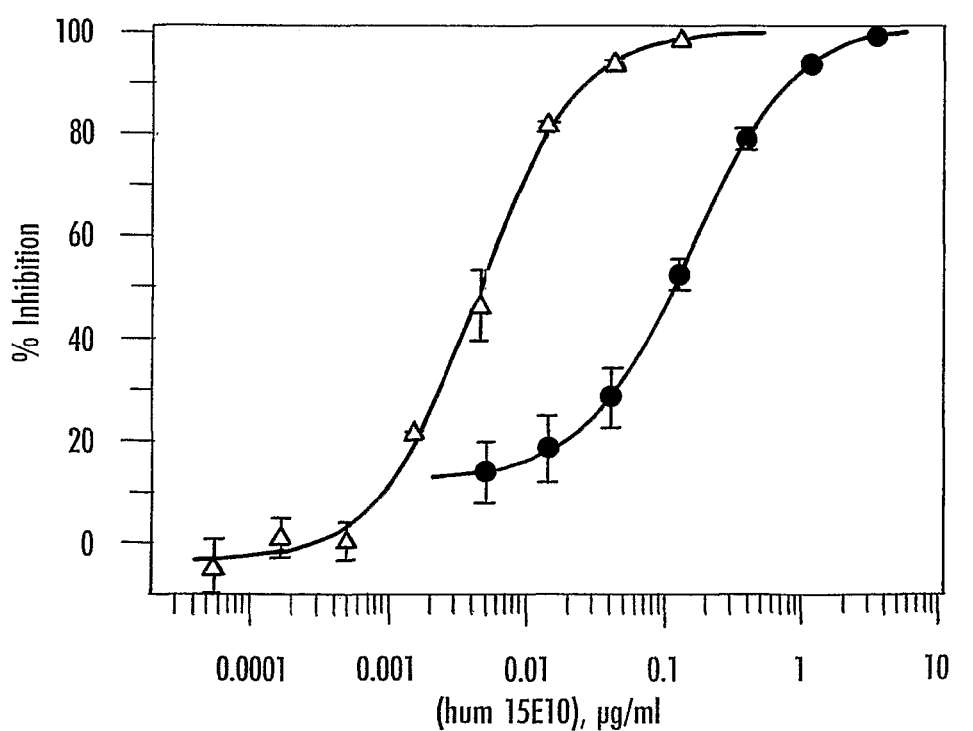

FIGS. 28a and 28b illustrates the KB assay in which the combination of a site II specific and site III specific antibody greatly increases the potency of OSM neutralisation when compared with either antibody alone.

The concentrations of antibodies used in the combinations are shown in the table below.

| [17H100] ng/ml | [hum 15E10] ng/ml |
|---|---|
| 20 | 120 |
| 7 | 40 |
| 2.2 | 13.3 |
| 0.7 | 4.4 |
| 0.3 | 1.5 |
| 0.082 | 0.5 |
| 0.027 | 0.165 |
| 0.0091 | 0.55 |

A comparison of the most active site II and site III specific antibodies showed that the latter were more potent in OSM neutralisation. However, cross reactivity of site II and site III antibodies with OSM from other species was found to be different, since all the potent site II antibodies neutralised Cynomolgus monkey OSM (in gp130-OSM ELISA and KB cell assays), whilst site III antibodies did not (only in the KB assay).

Blockade of OSM interaction with both gp130 and OSMRβ or LIFR presumably underlies the synergistic effects of site II and site III antibodies in OSM neutralisation. However, it is also possible that binding of an antibody could facilitate binding of another antibody directed at a different site.

Example 11.3

Optimisation of OSM Neutralisation by Combination of Site II and Site III Specific OSM Antibodies Since combination of site II and site III OSM antibodies greatly increased potency of neutralisation, a strategy for development of optimal concentrations can be envisaged, based on the binding affinities of the different antibodies. Example 11.3 is theoretical.

Initially the affinity of site II or site III specific antibodies for OSM, previously bound by site III or site II specific antibodies respectively, would be measured using plasmon resonance technology. If binding constants (Kd) are significantly different from binding of single antibodies to OSM, then a cooperative interaction in binding of site II and site III antibodies is occurring.

Based on data from these antibody binding studies, concentrations of site II and site III antibodies would be prepared ranging from 10 fold greater than the Kd values to 10 fold less than the Kd, using doubling dilutions. In addition, combinations of both antibodies would be prepared such that each concentration of the site II antibody is combined with every concentration of site III antibody, allowing exploration of equal binding of site II or site III antibodies to OSM, and dominance in site II and site III antibody binding. All antibody dilutions and combinations would be tested for OSM neutralisation in a KB cell assay. Data from this assay would allow selection of the antibody combination that was most potent in OSM neutralisation.

Example 12

Ability of Anti Site II OSM Specific Antibody to Inhibit OSM Stimulation of RA Synovial Fibroblasts Previously, we have shown that site II and site III specific OSM antibodies can inhibit OSM stimulation of KB cells. However, these cells are epithelial, are transformed and may not be representative of cells found in the rheumatoid synovium. We therefore investigated the efficacy of site II specific OSM antibodies to inhibit OSM stimulation of RA synovial fibroblasts.

Fibroblasts were seeded into 96 well plates at $2 \times 10^4$ cells/well and cultured in 10% FCS in DMEM until nearly confluent, replacing the medium 3 times a week. Culture medium was then changed to fresh culture medium containing, either no OSM, 1 ng/ml OSM, or 1 ng/ml OSM that had been pre-incubated for 1 h with various concentrations of anti OSM antibody in the medium. After 48 h, culture supernatants were removed and stored at −20° C. until analysis of IL-6 concentrations by ELISA.

Figure 29:
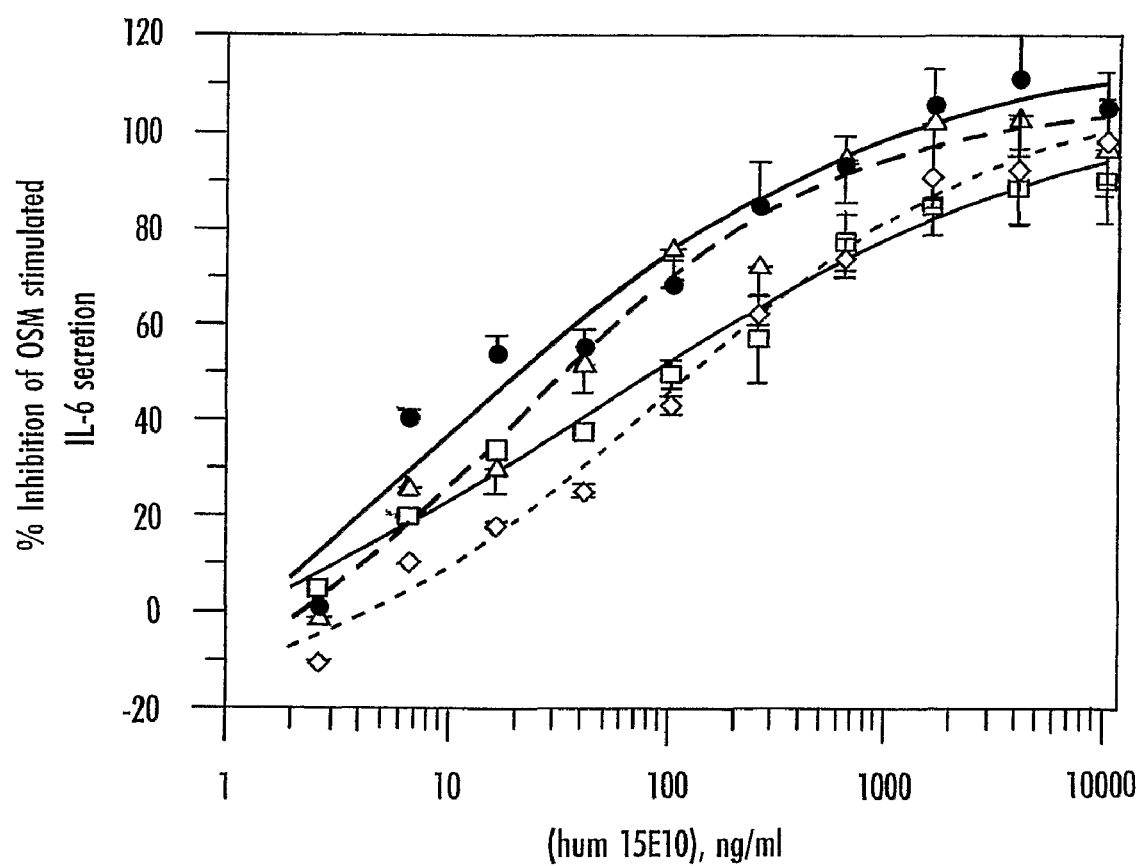
FIG. 29 illustrates the efficacy of humanised 15E10 antibody in inhibiting OSM stimulated IL-6 secretion from RA synovial fibroblasts. Each symbol refers to a fibroblasts obtained from different patients.

FIG. 29 illustrates representative data from 4 RA synovial fibroblast strains. The OSM antibody caused complete inhibition of OSM stimulated IL-6 secretion, although the potency of the antibody showed some variation between different strains.

Example 13

Effect of OSM Glycosylation on Potency of Neutralisation by Anti-OSM Antibodies

Figure 30:
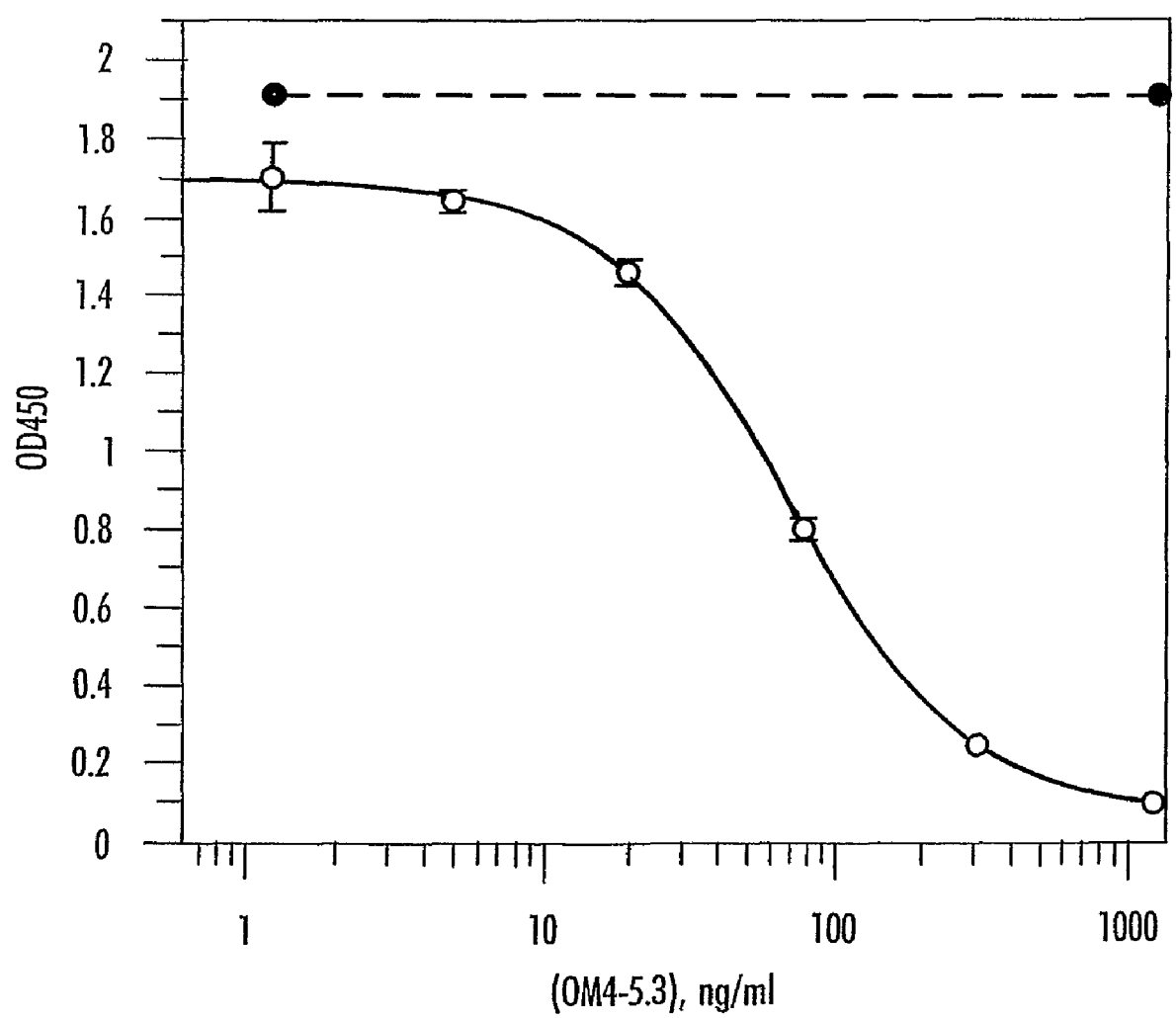
FIG. 30 illustrates the inhibition of OSM binding to gp130 by anti OSM antibody OM4-5.3. OSM (25 ng/ml) was preincubated with the concentrations of OM4-5.3 indicated before addition to the ELISA plate. OSM only; solid circles, OSM+OM4-5.3; open circles.

Anti OSM antibodies were raised by immunising mice with non-glycosylated OSM using methods previously described. Screening of these antibodies led to identification of a potent neutralising antibody (OM4-5.3) that interfered with OSM gp130 binding, as shown in FIG. 30.

Figure 31:
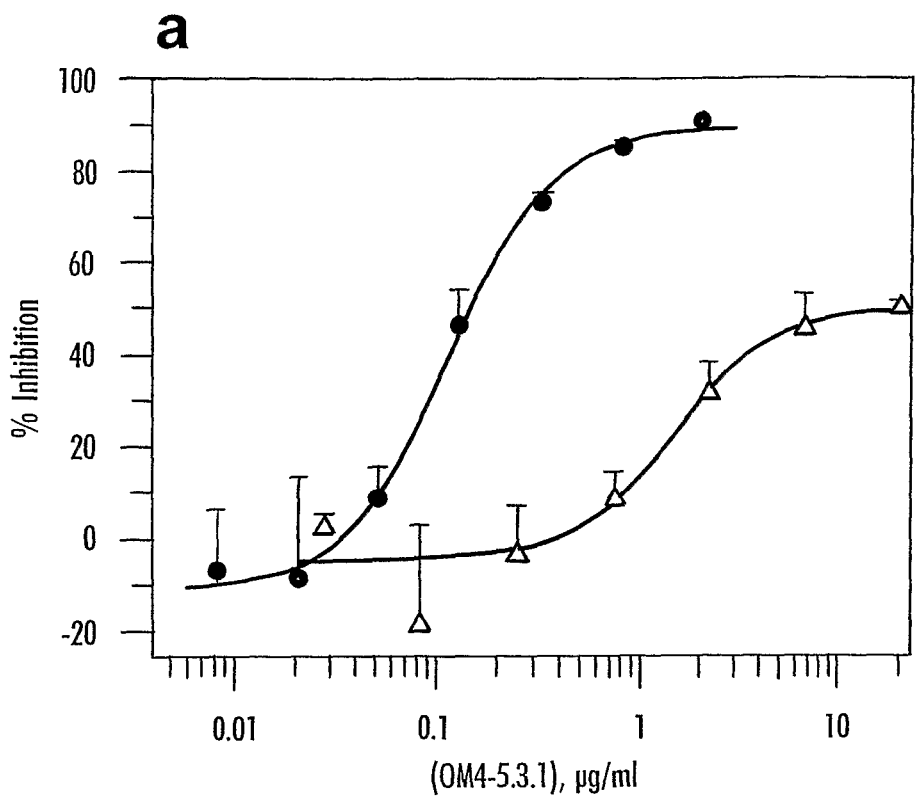
FIG. 31a illustrates the difference in potency of OM4-41.5 in inhibiting glycosylated and non-glycosylated OSM binding to gp130. Non-glycosylated OSM; solid circles, glycosylated OSM; open triangles.
FIG. 31b illustrates the difference in potency of OM4-5.3.1 in inhibiting glycosylated and non-glycosylated OSM binding to gp130. Non-glycosylated OSM; solid circles, glycosylated OSM; open triangles.
Figure 31:
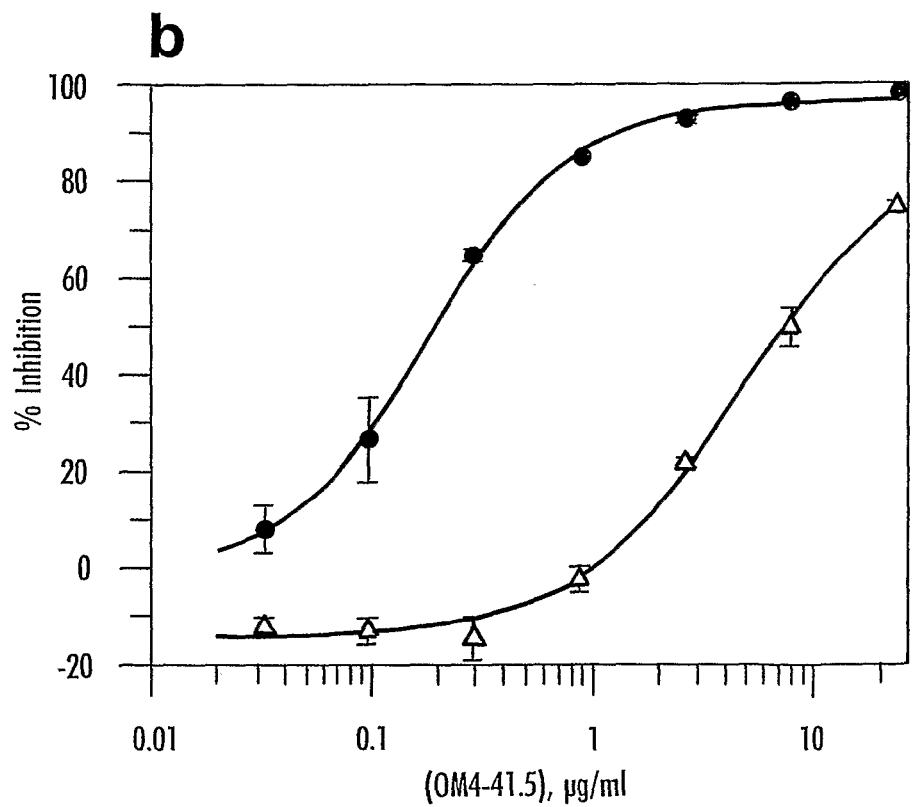

It was anticipated that OM5-5.3 would have similar potency against glycosylated OSM (CHO cell glycosylated). However, when the ability of a subclone of this antibody (OM4-5.3.1) to inhibit glycosylated OSM (hOSM glycosylated by a CHO cell) binding to gp130 was measured, a marked loss of potency was observed, as shown in FIG. 31a. Moreover this loss of potency against glycosylated OSM compared with non-glycosylated OSM was also seen in other site II specific antibodies derived from immunisation of a mouse with non-glycosylated OSM as shown in FIG. 31b.

Furthermore, site III antibodies derived from immunisations with non-glycosylated OSM also showed an approximate 10 fold potency reduction against glycosylated OSM compared with non-glycosylated OSM in a KB cell assay—see Table 1 below.

TABLE 1

| Antibody | non-glycos. OSM IC50 ng/ml | glycosylated OSM IC50 ng/ml |
|---|---|---|
| OM4-11.17 | 4.1 | 45.5 |
| OM4-11.31 | 7.7 | 89.6 |

Figure 32:
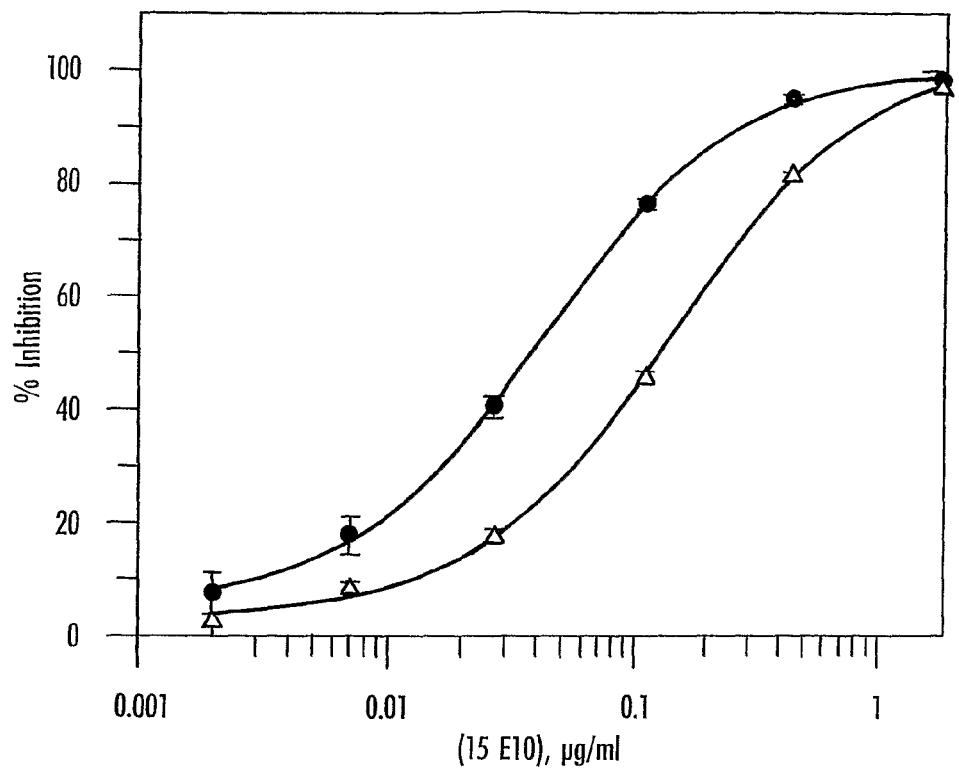
FIG. 32 shows the activity of two site II OSM specific antibodies (a; 15E10, b; 5H2) against glycosylated (filled circles) and non-glycosylated (open triangles) in the gp130-OSM ELISA
Figure 32:
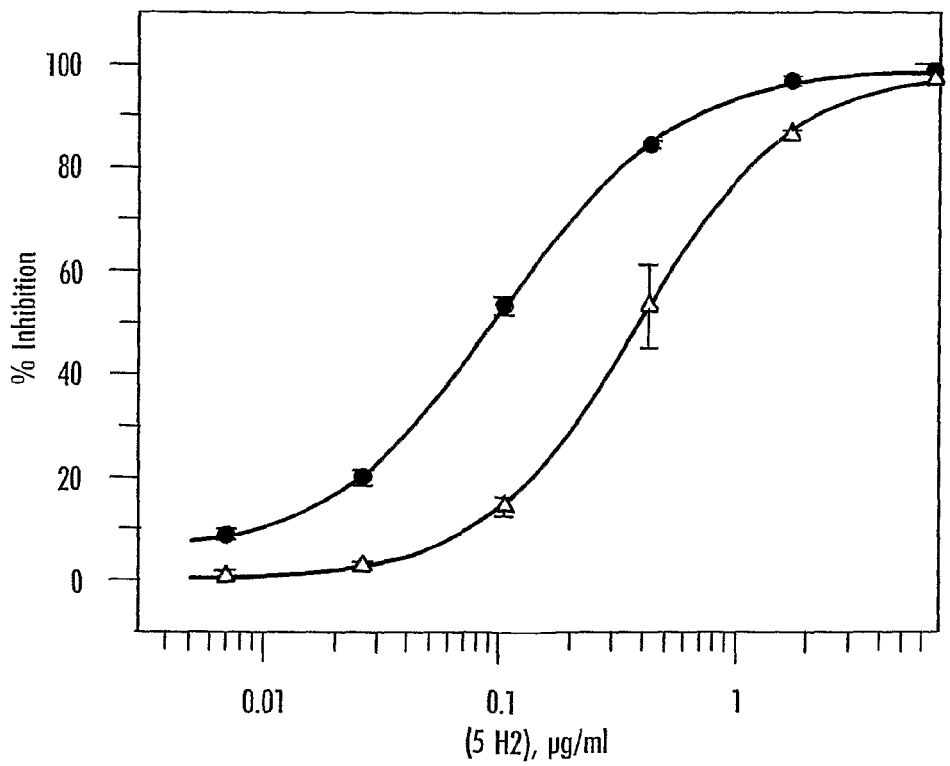

Since immunisation with non-glycosylated OSM resulted in antibodies that were more potent against non-glycosylated OSM rather than the glycosylated form, we thought that immunisation with glycosylated OSM may yield antibodies of higher potency against this form of OSM. This indeed turned out to be the case. FIGS. 32a and 32b illustrate the activity against glycosylated and non-glycosylated OSM in the gp130-OSM ELISA of two site II specific OSM antibodies (15E10 and 5H2) derived from glycosylated OSM immunisation.

Example 14

Correlation Between Serum and Synovial Fluid OSM Levels in RA Patients

One of the major sites of OSM production in RA patients is in arthritic joints, since high OSM levels can be measured in synovial fluid. In contrast, serum OSM levels in RA patients are very low, and it has only been possible to measure these accurately with the development of a high sensitivity ELISA as disclosed in example 16 below. We investigated the possible relationship between concentrations of OSM in arthritic joints and the circulation by measuring paired synovial fluid and serum samples from RA patients.

Figure 33:
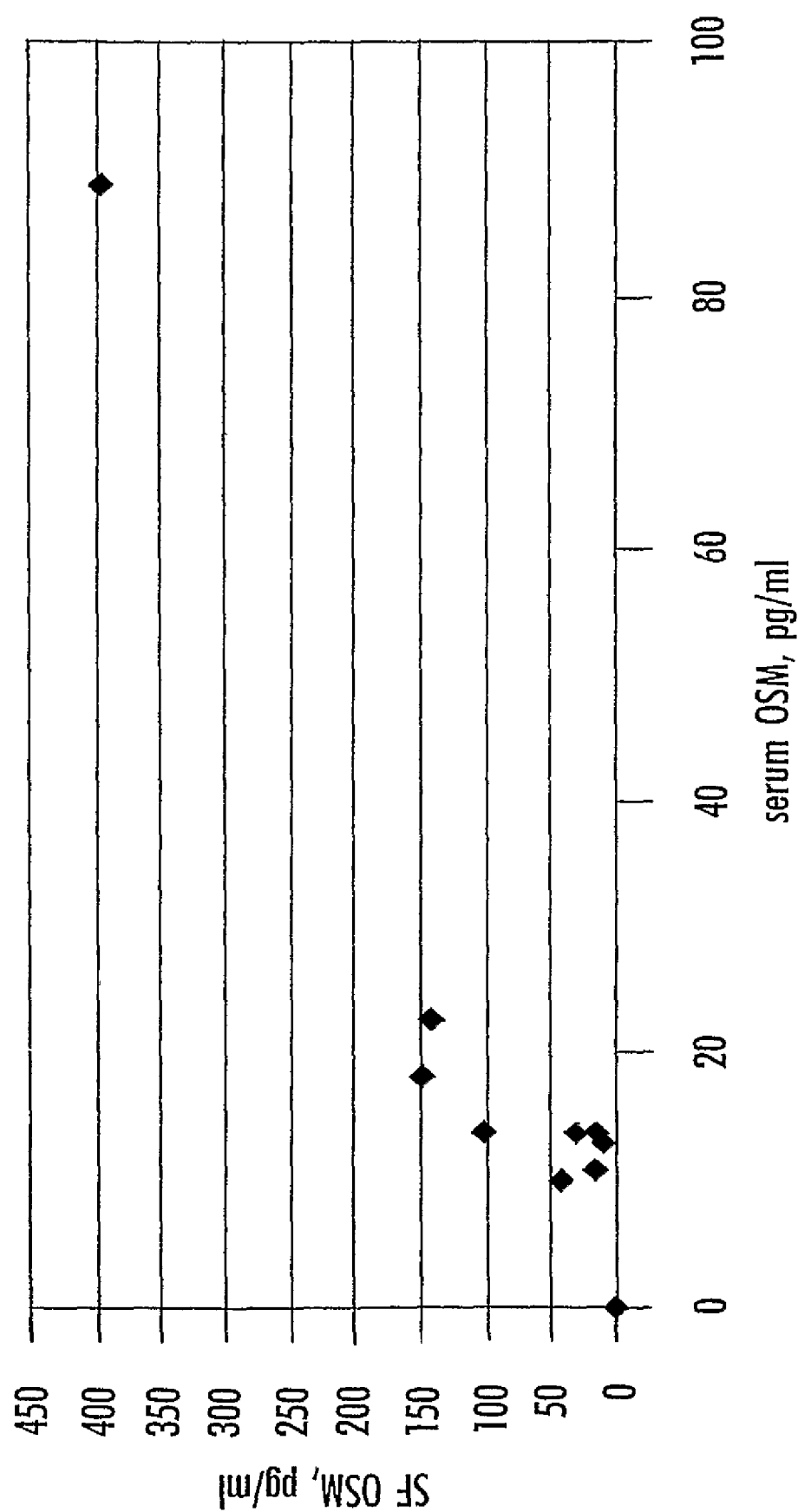
FIG. 33 illustrates the correlation between serum and synovial fluid [OSM] in paired serum and SF samples taken from RA patients.

OSM levels in sera and synovial fluids as measured by the ELISA assay set forth below (OM4-11.31 antibody capture of OSM) are shown in the table below, and FIG. 33 illustrates the relationship between the two measurements. Samples were frozen following sampling and thawed just prior to these measurements. The correlation coefficient for these two parameters, as determined by linear regression is 0.9447

| Patient | serum [OSM] pg/ml | SF[OSM] pg/ml |
|---|---|---|
| 1 | 9.8 | 43.24 |
| 2 | 13.7 | 101.445 |
| 3 | 0 | 0 |
| 4 | 88.56 | 397 |
| 5 | 22.64 | 142.12 |
| 6 | 18 | 147.4 |
| 7 | 13 | 9.2 |
| 8 | 13.8 | 29.88 |
| 9 | 10.68 | 14.76 |
| 10 | 13.8 | 15.96 |

The good correlation between sera and SF OSM levels suggest that sites of OSM production other than arthritic joints have relatively little influence on circulating OSM levels, or that these sites modulate OSM production in a way that correlates with production in the joint. In any event, the inventors speculate that the correlation may allow prediction of joint OSM levels from measurement of serum OSM and could find utility in dose setting of a neutralising OSM antibody for treatment of RA patients.

Example 15

Measurement of OSM in Synovial Fluid (SF) and Sera from OA Patients

Since cartilage degradation is a characteristic of osteoarthritis and OSM, particularly in synergy with IL-1 and other cytokines can induce cartilage breakdown, we measured OSM levels in synovial fluids and sera from OA patients.

Cells were removed from SF samples by centrifugation. Supernatants were treated for 1 h with 0.1 U/ml hyaluronidase (Fluka, 53725) for 1 h at room temperature after which they were centrifuged at 4000 rpm for 10 minutes. The supernatants were removed, divided into aliquots and stored at −80° C. until analysis.

Figure 34:
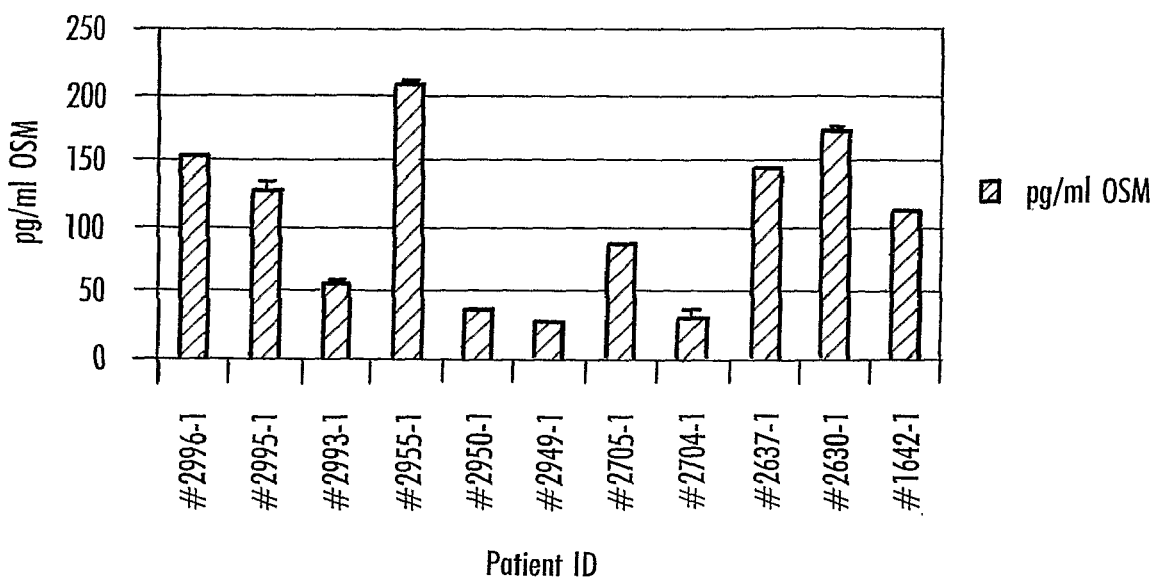
FIGS. 34a, 34b and 35 illustrate the OSM concentrations measured in OA synovial fluid using the OSM ELISA of the examples.
Figure 34:
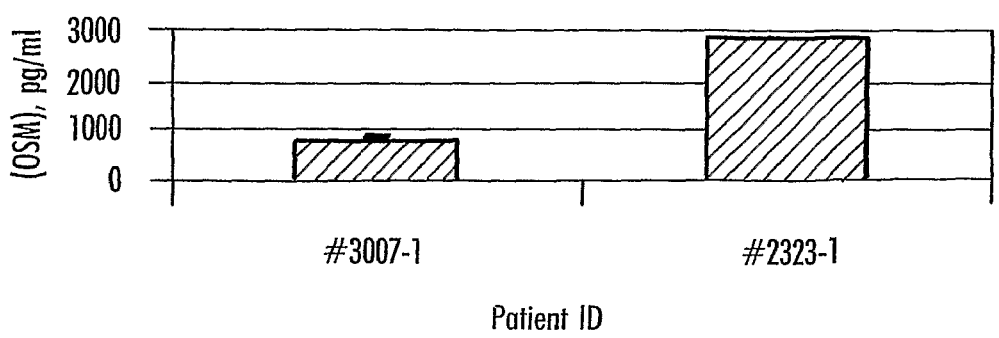
Figure 35:
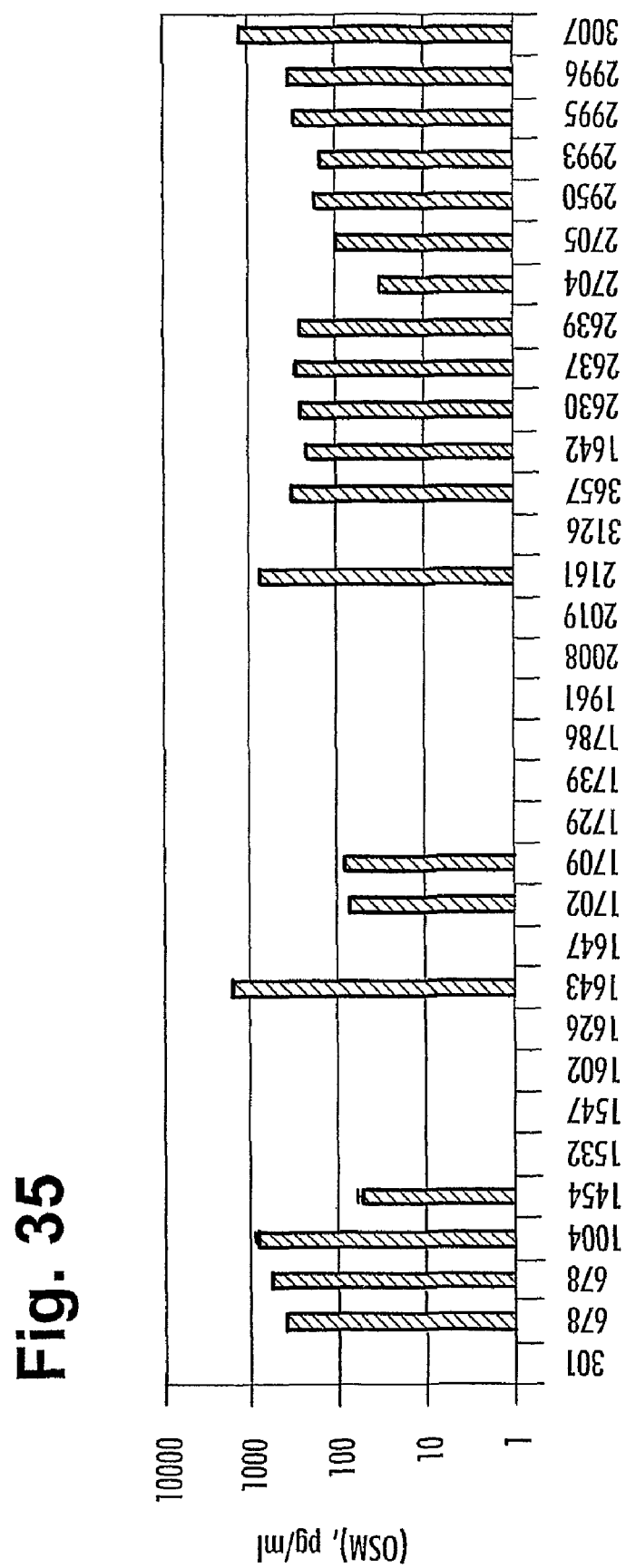

OSM concentrations in OA SFs were analysed using the ELISA assay of Example 16 in two experiments shown in FIGS. 34a and b and 35.

Although 13 of the 460A SFs had no detectable OSM, many contained OSM at relatively high levels (>200 pg/ml) and OSM concentrations of >1000 pg/ml were detected in three samples.

Example 15.1

OSM Concentrations in OA Sera

Figure 36:
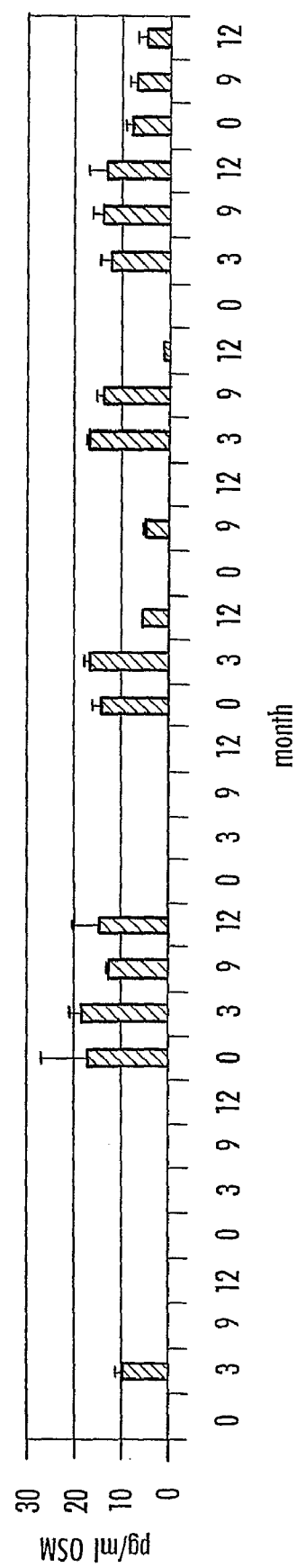
FIG. 36 illustrates the OSM concentration found in OA patient sera over a 12 month clinical trial period. #number is the patient identifier.

The high concentrations of OSM in OA synovial fluid were surprising, since previous reports suggest that OSM levels in OA synovial fluid tend to be lower than in RA SF (see Manicourt D H et al (2000) Arthritis Rheum. 43(2): 281-88). We also measured OSM levels in sera from OA patients on a clinical trial at several different time points over a 12 month period using the ELISA assay of example 16 below. FIG. 36 illustrates that serum OSM concentrations were either low or non-detectable in these patients. However no correlation was made between OSM levels in sera and synovial fluid in OA patients as the samples were not paired.

Example 16

Sensitive ELISA for Detecting OSM in Biological Samples at Low Concentrations

Figure 37:
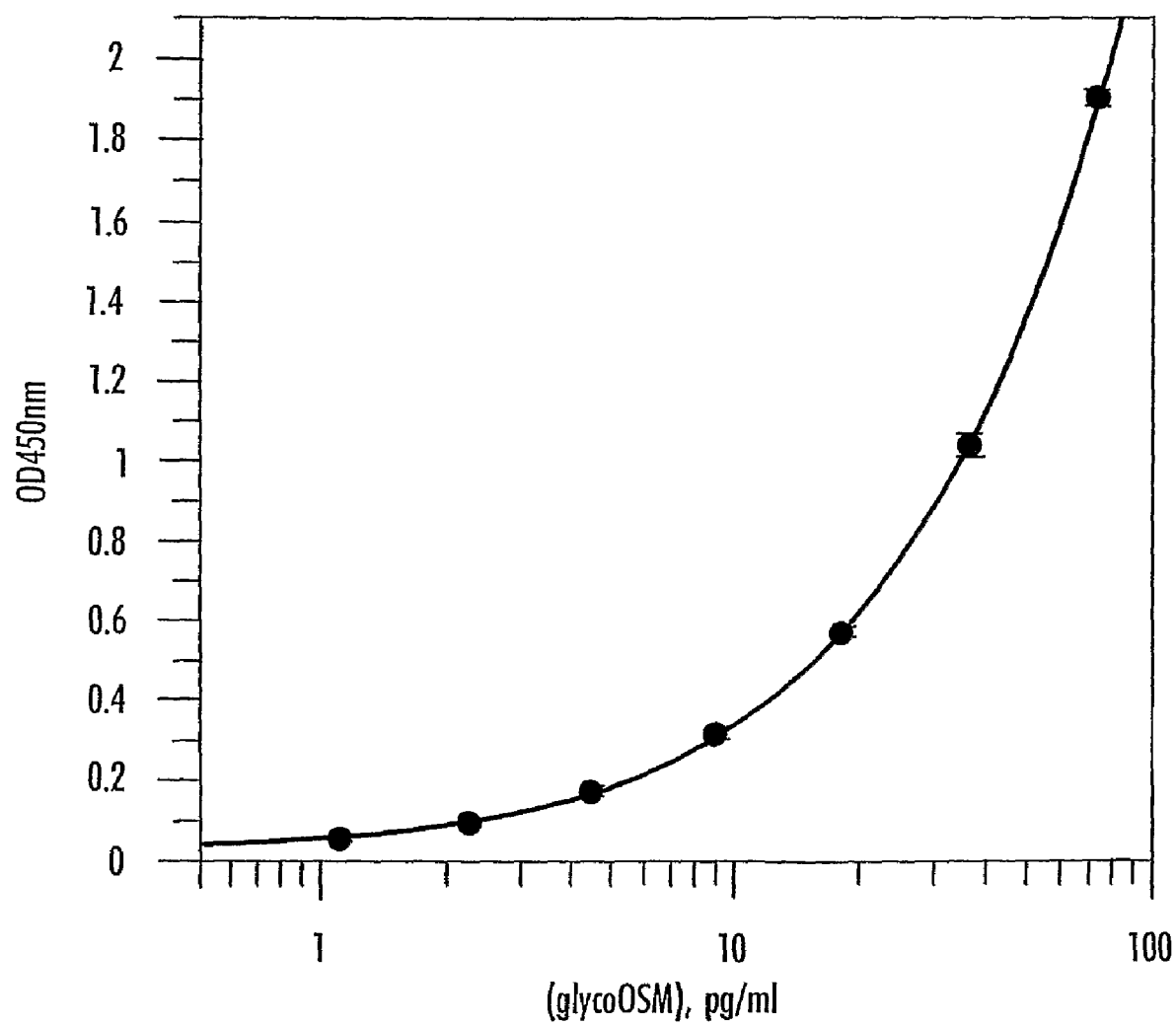
FIG. 37 illustrates a typical OSM standard curve in 25% human AB serum

We have developed a sensitive ELISA for measurement of OSM in biological samples using the site III OSM specific capture antibody OM4-11.31 This ELISA allows detection of OSM down to <2 pg/ml as shown in FIG. 37 and has been used for analysis of serum and synovial fluid samples.

The protocol for using this ELISA with serum samples of synovial flu ids is given below.

OSM ELISA Protocol

Materials and Reagents

11. Nunc Immunoplate F96 maxisorp (Life Technologies 4-39454A)
12. Monoclonal anti human OSM (OM4-11.31 GSK)
13. Glycosylated hOSM @ 420 ug/ml (CHO cell glycosylated)
14. Biotinylated goat anti human OSM 50 μg/ml (R&D Systems BAF295)
15. Streptavidin HRP (Amersham RPN4401)

16. PBS (SIGMA D8537 μL)
17. BSA (SIGMA A7888 500 g)
18. Phenol red solution 0.5% (SIGMA P290 100 ml)
19. TMB (SIGMA T-8665 1 L)
20. Pooled AB normal male serum control (SIGMA H4522) Batch #043K0500
21. Sulphuric acid @ 1M
22. PBS tablets (SIGMA P4417 100 tabs)
23. Tween 20 (Sigma P7949)
24. Plate sealers Preparation of Reagents Preparation of plates—Dilute the monoclonal anti human OSM to 4 μg/ml in PBS Add 50 μl/well, cover with sealing strip and incubate overnight at 4° C.

Wash buffer—To 5 L deionised water add 25 PBS tablets+2.5 ml Tween 20 (0.05%)

Block Buffer—

To 500 ml PBS add 10 g BSA (2%).

(add 800 ul phenol red, and 5M NaOH until pH is neutral)

AB Blood Serum Control

Spin the 100 ml in Sorvall centrifuge @ 16K, 30 mins (used 4×Oakridge tubes balanced to 0.02 g)

Pass supernatant through sterile gause (still cloudy but no particulates) Aliquot and freeze.

On day of assay, thaw AB serum, microfuge 13K for 5 min, and dilute 1→4 in PBS (Serum will be opaque but is fine to use)

Preparation of Standards

For analysis of serum make up standards in AB serum diluted 1→4 PBS

For analysis of SFs make up standards in 1% BSA in PBS

If maximum sensitivity is desired:

Use standards at 112, 56, 28, 14, 7, 3.5 1.75 and 0 pg/ml OSM

Method

5. Wash the plate 4× with wash buffer and tap dry.
6. Add 200 μl/well block buffer, seal plate and shake 2 hrs @ RT, or static overnight @+4
7. Wash as in step 1.
8. Add 50 μl/well standard or sample. Cover and agitate 2 hrs at room temperature.
   (Standard is diluted in 25% pooled AB serum if serum samples are to be analysed)
5. Wash as in step 1.
6. Add 50 μl/well biotinylated anti human OSM diluted to 50 ng/ml in block buffer with 1% goat serum. Cover and agitate 1 hour at room temperature.
7. Wash as in step 1.
8. Add 50 μl/well streptavidin HRP 1/4000 in block buffer. Cover and agitate 30 mins at RT
9. Wash as in step 1.
10. Add 100 ul TMB substrate. Cover and agitate 40 mins @ RT
11. To stop assay add 50 μL/well 1M $H_2SO_4$.
12. Read immediately @ 450 nm after shaking plate

The invention claimed is:

1. An isolated therapeutic antibody that specifically binds to OSM, and modulates the interaction between OSM and gp130 comprising:
   CDRH1 of SEQ. I.D. NO: 1,
   CDRH2 of SEQ. I.D. NO: 2,
   CDRH3 of SEQ. I.D. NO: 3,
   CDRL1 of SEQ. I.D. NO: 4,
   CDRL2 of SEQ. I.D. NO: 5, and
   CDRL3 of SEQ. I.D. NO: 6.

2. The therapeutic antibody of claim 1, which specifically binds hOSM and modulates the interaction between hOSM and gp130 comprising a VH domain of SEQ. I.D. NO: 9 and a VL domain of SEQ. I.D. NO: 10.

3. The therapeutic antibody of claim 1, which specifically binds hOSM and modulates the interaction between hOSM and gp130 comprising a heavy chain of SEQ. I.D. NO: 11 and a light chain of SEQ. I.D. NO: 12.

4. The isolated therapeutic antibody according to claim 1, wherein the antibody is selected from the group consisting of: an intact antibody, a chimaeric antibody, a humanized antibody, a bispecific antibody, and a heteroconjugate antibody.

5. The isolated therapeutic antibody according to claim 1, wherein the antibody is an intact antibody.

6. The antibody according to claim 5, wherein the intact antibody is selected from the group consisting of: a murine intact antibody, a rat intact antibody, a rabbit intact antibody, a primate intact antibody, and a human intact antibody.

7. The antibody according to claim 5, wherein the intact antibody is a human intact antibody.

8. The isolated therapeutic antibody according to claim 1, wherein the antibody is a chimaeric antibody.

9. The isolated therapeutic antibody according to claim 1, wherein the antibody is a humanized antibody.

10. The antibody of claim 5, wherein the intact antibody is humanized.

11. The isolated therapeutic antibody according to claim 1, further comprising a human heavy chain constant region selected from the group consisting of; IgA1, IgA2, IgD, IgE, IgG1, IgG2, IgG3, IgG4, and IgM.

12. The isolated therapeutic antibody according to claim 11, wherein the constant region is of an IgG isotype.

13. The isolated therapeutic antibody according to claim 12, wherein the constant region is IgG1.

14. The isolated therapeutic antibody according to claim 13, wherein the constant region is mutated to render the antibody non-lytic.

15. The isolated therapeutic antibody according to claim 1, wherein said antibody modulates an interaction between Site II of hOSM and gp130.

16. The isolated therapeutic antibody according to claim 15, wherein said antibody inhibits said interaction.

17. The isolated therapeutic antibody according to claim 15, wherein said antibody blocks said interaction.

18. An antigen binding fragment of the isolated therapeutic antibody according to claim 1.

19. The antigen binding fragment according to claim 18, wherein said fragment is selected from the group consisting of: Fab, Fab', Fd, F(ab)$_2$, and ScFv.

20. A pharmaceutical composition comprising an isolated therapeutic antibody according to claim 1.

21. A pharmaceutical composition comprising an antigen binding fragment of the isolated therapeutic antibody according to claim 1.

22. An isolated therapeutic antibody according to claim 1, wherein said antibody is capable of binding hOSM and cOSM.

23. The isolated therapeutic antibody according to claim 1, wherein said OSM is human OSM.

* * * * *

```
                         SEQUENCE LISTING

<160> NUMBER OF SEQ ID NOS: 65

<210> SEQ ID NO 1
   <211> LENGTH: 5
   <212> TYPE: PRT
   <213> ORGANISM: Mus sp.

<400> SEQUENCE: 1

Asn Tyr Gly Val His
   1               5

<210> SEQ ID NO 2
   <211> LENGTH: 16
   <212> TYPE: PRT
   <213> ORGANISM: Mus sp.

<400> SEQUENCE: 2

Val Ile Trp Arg Gly Gly Ser Thr Asp Tyr Asn Ala Ala Phe Met Ser
   1               5                   10                  15

<210> SEQ ID NO 3
   <211> LENGTH: 12
   <212> TYPE: PRT
   <213> ORGANISM: Mus sp.

<400> SEQUENCE: 3

Ser Pro Asn Ser Asn Phe Tyr Trp Tyr Phe Asp Val
   1               5                   10
```

```
<210> SEQ ID NO 4
<211> LENGTH: 10
<212> TYPE: PRT
<213> ORGANISM: Mus sp.

<400> SEQUENCE: 4

Ser Gly Ser Ser Val Ser Tyr Met Tyr
1               5                   10

<210> SEQ ID NO 5
<211> LENGTH: 7
<212> TYPE: PRT
<213> ORGANISM: Mus sp.

<400> SEQUENCE: 5

Asp Thr Ser Asn Leu Ala Ser
1               5

<210> SEQ ID NO 6
<211> LENGTH: 9
<212> TYPE: PRT
<213> ORGANISM: Mus sp.

<400> SEQUENCE: 6

Gln Gln Trp Ser Ser Tyr Pro Pro Thr
1               5

<210> SEQ ID NO 7
<211> LENGTH: 120
<212> TYPE: PRT
<213> ORGANISM: Mus sp.

<400> SEQUENCE: 7

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Arg Gly Gly Ser Thr Asp Tyr Asn Ala Ala Phe Met
        50                  55                  60

Ser Arg Leu Ser Ile Thr Lys Asp Asn Ser Arg Ser Gln Val Phe Phe
65                  70                  75                  80

Lys Met Asn Ser Leu Gln Ala Asp Asp Thr Ala Ile Tyr Tyr Cys Ala
                85                  90                  95

Lys Ser Pro Asn Ser Asn Phe Tyr Trp Tyr Phe Asp Val Trp Gly Thr
                100                 105                 110

Gly Thr Thr Val Thr Val Ser Ser
            115                 120

<210> SEQ ID NO 8
<211> LENGTH: 106
<212> TYPE: PRT
<213> ORGANISM: Mus sp.

<400> SEQUENCE: 8

Gln Ile Val Leu Thr Gln Ser Pro Thr Ile Met Ser Ala Ser Pro Gly
1               5                   10                  15

Glu Lys Val Thr Met Thr Cys Ser Gly Ser Ser Val Ser Tyr Met
                20                  25                  30
```

```
Tyr Trp Tyr Gln Glu Lys Pro Gly Ser Ser Pro Arg Leu Leu Ile Glu
             35                  40                  45

Asp Thr Ser Asn Leu Ala Ser Gly Val Pro Ala Arg Phe Ser Gly Ser
         50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Trp Ser Ser Tyr Pro Pro Thr
                 85                  90                  95

Phe Gly Ser Gly Thr Lys Leu Glu Ile Lys
                100                 105

<210> SEQ ID NO 9
<211> LENGTH: 120
<212> TYPE: PRT
<213> ORGANISM: Artificial sequence
<220> FEATURE:
<223> OTHER INFORMATION: VH domain (humanised, B3)

<400> SEQUENCE: 9

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Leu Thr Asn Tyr
             20                  25                  30

Gly Val His Trp Val Arg Gln Ala Pro Gly Lys Gly Leu Glu Trp Val
         35                  40                  45

Ala Val Ile Trp Arg Gly Gly Ser Thr Asp Tyr Asn Ala Ala Phe Met
 50                  55                  60

Ser Arg Phe Thr Ile Ser Lys Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Pro Asn Ser Asn Phe Tyr Trp Tyr Phe Asp Val Trp Gly Arg
                100                 105                 110

Gly Thr Leu Val Thr Val Ser Ser
        115                 120

<210> SEQ ID NO 10
<211> LENGTH: 106
<212> TYPE: PRT
<213> ORGANISM: Artificial sequence
<220> FEATURE:
<223> OTHER INFORMATION: VL domain (humanised, L2)

<400> SEQUENCE: 10

Glu Ile Val Leu Thr Gln Ser Pro Ala Thr Leu Ser Leu Ser Pro Gly
 1               5                  10                  15

Glu Arg Ala Thr Leu Ser Cys Ser Gly Ser Ser Ser Val Ser Tyr Met
             20                  25                  30

Tyr Trp Tyr Gln Gln Lys Pro Gly Gln Ala Pro Arg Leu Leu Ile Glu
             35                  40                  45

Asp Thr Ser Asn Leu Ala Ser Gly Ile Pro Ala Arg Phe Ser Gly Ser
         50                  55                  60

Gly Ser Gly Thr Asp Tyr Thr Leu Thr Ile Ser Asn Leu Glu Pro Glu
 65                  70                  75                  80

Asp Phe Ala Val Tyr Tyr Cys Gln Gln Trp Ser Ser Tyr Pro Pro Thr
                 85                  90                  95

Phe Gly Gln Gly Thr Lys Leu Glu Ile Lys
```

<210> SEQ ID NO 11
<211> LENGTH: 450
<212> TYPE: PRT
<213> ORGANISM: Artificial sequence
<220> FEATURE:
<223> OTHER INFORMATION: Heavy chain (humanised)

<400> SEQUENCE: 11

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Ser Leu Thr Asn Tyr
            20                  25                  30
Gly Val His Trp Val Arg Gln Ala Pro Gly Lys Gly Leu Glu Trp Val
        35                  40                  45
Ala Val Ile Trp Arg Gly Gly Ser Thr Asp Tyr Asn Ala Ala Phe Met
    50                  55                  60
Ser Arg Phe Thr Ile Ser Lys Asp Asn Ser Lys Asn Thr Leu Tyr Leu
65                  70                  75                  80
Gln Met Asn Ser Leu Arg Ala Glu Asp Thr Ala Val Tyr Tyr Cys Ala
                85                  90                  95
Lys Ser Pro Asn Ser Asn Phe Tyr Trp Tyr Phe Asp Val Trp Gly Arg
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
```

```
                355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
                435                 440                 445

Gly Lys
    450

<210> SEQ ID NO 12
<211> LENGTH: 213
<212> TYPE: PRT
<213> ORGANISM: Artificial sequence
<220> FEATURE:
<223> OTHER INFORMATION: Light chain (humanised)

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Ser Gly Ser Ser Ser Val Ser Tyr Met
                20                  25                  30

Tyr Trp Tyr Gln Gln Lys Pro Gly Gln Ala Pro Arg Leu Leu Ile Glu
            35                  40                  45

Asp Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Asn Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 13
<211> LENGTH: 252
<212> TYPE: PRT
<213> ORGANISM: Homo sapiens

<400> SEQUENCE: 13
```

```
Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
                35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
                100                 105                 110

Leu Glu Gln Arg Leu Pro Lys Ala Gln Asp Leu Glu Arg Ser Gly Leu
            115                 120                 125

Asn Ile Glu Asp Leu Glu Lys Leu Gln Met Ala Arg Pro Asn Ile Leu
130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
            195                 200                 205

Phe Ser Lys Trp Gly Glu Ser Pro Asn Arg Ser Arg Arg His Ser Pro
        210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 14
<211> LENGTH: 759
<212> TYPE: DNA
<213> ORGANISM: Homo sapiens

<400> SEQUENCE: 14
atgggggtac tgctcacaca gaggacgctg ctcagtctgg tccttgcact cctgtttcca        60
agcatggcga gcatggcggc tataggcagc tgctcgaaag agtaccgcgt gctccttggc       120
cagctccaga gcagacagaa tctcatgcag gacaccagca gactcctgga ccctatata       180 cgtatccaag gcctggatgt tcctaaactg agagagcact gcagggagcg ccccgggcc       240 ttccccagtg aggagaccct gaggggctg ggcaggcggg gcttcctgca gaccctcaat        300
gccacactgg gctgcgtcct gcacagactg gccgacttag agcagcgcct ccccaaggcc       360
caggatttgg agaggtctgg gctgaacatc gaggacttgg agaagctgca gatggcgagg       420
ccgaacatcc tcgggctcag gaacaacatc tactgcatgg cccagctgct ggacaactca       480
gacacggctg agcccacgaa ggctggccgg ggggcctctc agccgccac ccccaccct       540 gcctcggatg cttttcagcg caagctggag ggctgcaggt tcctgcatgg ctaccatcgc       600
ttcatgcact cagtggggcg ggtcttcagc aagtgggggg agagcccgaa ccggagccgg       660
```

```
agacacagcc cccaccaggc cctgaggaag ggggtgcgca ggaccagacc ctccaggaaa    720
ggcaagagac tcatgaccag gggacagctg ccccggtag                          759

<210> SEQ ID NO 15
<211> LENGTH: 360
<212> TYPE: DNA
<213> ORGANISM: Mus sp.

<400> SEQUENCE: 15
caggtgcaac tgaagcagtc aggacctggc ctagtgcagc cctcacagag cctgtccata    60
acctgcacag tctctggttt ctcattaact aattatggtg tacactgggt tcgccagtct   120
ccaggaaagg gtctggagtg gctgggagtg atatggagag gtggaagcac agactacaat   180
gcagctttca tgtccagact gagcatcacc aaggacaact ccaggagcca agttttcttt   240
aaaatgaaca gtctacaagc tgatgacact gccatatact actgtgccaa aagtccgaat   300
agtaactttt actggtattt cgatgtctgg ggcacaggga ccacggtcac cgtctcctca   360

<210> SEQ ID NO 16
<211> LENGTH: 318
<212> TYPE: DNA
<213> ORGANISM: Mus sp.

<400> SEQUENCE: 16
caaattgttc tcacccagtc tccaacaatc atgtctgcat ctccagggga aaggtcacc    60 atgacctgca gtggcagctc aagtgtaagt tacatgtatt ggtaccagga aagccagga   120 tcctccccca gactcctgat tgaagacaca tccaacctgg cttctggagt ccctgctcgc   180
ttcagtggca gtgggtctgg gacctcttac tctctcacaa tcagccgaat ggaggctgaa   240
gatgctgcca cttattactg tcaacagtgg agtagttatc cacccacgtt cggctcgggg   300
acaaagttgg aaatcaaa                                                 318

<210> SEQ ID NO 17
<211> LENGTH: 360
<212> TYPE: DNA
<213> ORGANISM: Artificial sequence
<220> FEATURE:
<223> OTHER INFORMATION: VH domain (humanised, PN, B3)

<400> SEQUENCE: 17
caggtgcagc tggtggagtc tggggggaggc gtggtccagc ctggggaggtc cctgagactc    60 tcctgtgcag cgtctggatt ctcattaact aattatggtg tacactgggt ccgccaggct   120
ccaggcaagg ggctggagtg ggtggcagtg atatggagag gtggaagcac agactacaat   180
gcagctttca tgtcccgatt caccatctcc aaggacaatt ccaagaacac gctgtatctg   240
caaatgaaca gcctgagagc cgaggacacg gctgtgtatt actgtgcgaa aagtccgaat   300
agtaactttt actggtattt cgatgtctgg ggccgtggca cactagtcac agtctcctca   360

<210> SEQ ID NO 18
<211> LENGTH: 318
<212> TYPE: DNA
<213> ORGANISM: Artificial sequence
<220> FEATURE:
<223> OTHER INFORMATION: VL domain (humanised, PN, L2)

<400> SEQUENCE: 18
gaaattgtgt tgacacagtc tccagccacc ctgtctttgt ctccagggga aagagccacc    60
ctctcctgca gtggcagctc aagtgtaagt tacatgtatt ggtaccaaca gaaacctggc   120
```

| | |
|---|---|
| caggctccca ggctcctcat cgaagacaca tccaacctgg cttctggcat cccagccagg | 180 |
| ttcagtggca gtgggtctgg acagactac actctcacca tcagcaacct agagcctgaa | 240 |
| gattttgcag tttattactg tcaacagtgg agtagttatc cacccacgtt tggccagggg | 300 |
| accaagctgg agatcaaa | 318 |

<210> SEQ ID NO 19
<211> LENGTH: 1350
<212> TYPE: DNA
<213> ORGANISM: Artificial sequence
<220> FEATURE:
<223> OTHER INFORMATION: Heavy chain (humanised, PN)

<400> SEQUENCE: 19

| | |
|---|---|
| caggtgcagc tggtggagtc tgggggaggc gtggtccagc ctggggaggtc cctgagactc | 60 |
| tcctgtgcag cgtctggatt ctcattaact aattatggtg tacactgggt ccgccaggct | 120 |
| ccaggcaagg ggctggagtg ggtggcagtg atatggagag gtggaagcac agactacaat | 180 |
| gcagctttca tgtcccgatt caccatctcc aaggacaatt ccaagaacac gctgtatctg | 240 |
| caaatgaaca gcctgagagc cgaggacacg gctgtgtatt actgtgcgaa aagtccgaat | 300 |
| agtaactttt actggtattt cgatgtctgg ggccgtggca cactagtcac agtctcctca | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 20
<211> LENGTH: 639
<212> TYPE: DNA
<213> ORGANISM: Artificial sequence
<220> FEATURE:
<223> OTHER INFORMATION: Light chain (humanised, PN)

<400> SEQUENCE: 20

| | |
|---|---|
| gaaattgtgt tgacacagtc tccagccacc ctgtctttgt ctccagggga aagagccacc | 60 |
| ctctcctgca gtggcagctc aagtgtaagt tacatgtatt ggtaccaaca gaaacctggc | 120 |

```
caggctccca ggctcctcat cgaagacaca tccaacctgg cttctggcat cccagccagg    180
ttcagtggca gtgggtctgg acagactac actctcacca tcagcaacct agagcctgaa     240
gattttgcag tttattactg tcaacagtgg agtagttatc cacccacgtt tggccagggg    300
accaagctgg agatcaaacg tacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggac aacgccctcc aatcgggtaa ctcccaggag     480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgt                           639
```

<210> SEQ ID NO 21
<211> LENGTH: 120
<212> TYPE: PRT
<213> ORGANISM: Artificial sequence
<220> FEATURE:
<223> OTHER INFORMATION: VH domain (B4, humanised)

<400> SEQUENCE: 21

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Pro Asn Ser Asn Phe Tyr Trp Tyr Phe Asp Val Trp Gly Arg
            100                 105                 110

Gly Thr Leu Val Thr Val Ser Ser
        115                 120
```

<210> SEQ ID NO 22
<211> LENGTH: 37
<212> TYPE: DNA
<213> ORGANISM: Artificial sequence
<220> FEATURE:
<223> OTHER INFORMATION: VH forward primer

<400> SEQUENCE: 22

```
gatgaagctt gccaccatgg ctgtcctagg gctactc                              37
```

<210> SEQ ID NO 23
<211> LENGTH: 28
<212> TYPE: DNA
<213> ORGANISM: Artificial sequence
<220> FEATURE:
<223> OTHER INFORMATION: VH reverse primer

<400> SEQUENCE: 23

```
gatggactag tgtccctgtg ccccagac                                        28
```

<210> SEQ ID NO 24
<211> LENGTH: 37

```
<212> TYPE: DNA
<213> ORGANISM: Artificial sequence
<220> FEATURE:
<223> OTHER INFORMATION: VL forward primer

<400> SEQUENCE: 24
gatgaagctt gccaccatgg attttcaggt gcagatt                              37

<210> SEQ ID NO 25
<211> LENGTH: 31
<212> TYPE: DNA
<213> ORGANISM: Artificial sequence
<220> FEATURE:
<223> OTHER INFORMATION: VL reverse primer

<400> SEQUENCE: 25
gatgcgtacg tttgatttcc aactttgtcc c                                    31

<210> SEQ ID NO 26
<211> LENGTH: 124
<212> TYPE: PRT
<213> ORGANISM: Homo sapiens

<400> SEQUENCE: 26
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Pro Ser Ser Gly Ser Tyr Tyr Tyr Tyr Tyr Gly Met Asp
            100                 105                 110

Val Trp Gly Gln Gly Thr Thr Val Thr Val Ser Ser
        115                 120

```
<210> SEQ ID NO 27
<211> LENGTH: 121
<212> TYPE: PRT
<213> ORGANISM: Homo sapiens

<400> SEQUENCE: 27
```

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Gly Pro Leu Tyr Trp Tyr Phe Asp Leu Trp Gly
            100                 105                 110

Arg Gly Thr Leu Val Thr Val Ser Ser
            115                 120

<210> SEQ ID NO 28
<211> LENGTH: 106
<212> TYPE: PRT
<213> ORGANISM: Homo sapiens

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Lys Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Asn Leu Glu Pro
65                  70                  75                  80

Glu Asp Phe Ala Val Tyr Tyr Cys Gln Gln Arg Ser Asn Trp Pro Pro
            85                  90                  95

Thr Phe Gly Gln Gly Thr Lys Leu Glu Ile
            100                 105

<210> SEQ ID NO 29
<211> LENGTH: 116
<212> TYPE: PRT
<213> ORGANISM: Artificial sequence
<220> FEATURE:
<223> OTHER INFORMATION: Humanised VH construct A1

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
            35                  40                  45

Gly Val Ile Trp Arg Gly Gly Ser Thr Asp Tyr Asn Ala Ala Phe Met
50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Lys Ser Pro Asn Ser Asn Phe Tyr Trp Tyr Phe Asp Val Trp Gly Gln
            100                 105                 110

Gly Thr Thr Ser
        115

<210> SEQ ID NO 30
<211> LENGTH: 116
<212> TYPE: PRT
<213> ORGANISM: Artificial sequence
<220> FEATURE:
<223> OTHER INFORMATION: Humanised VH construct A2

<400> SEQUENCE: 30

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ser Thr Asp Tyr Asn Ala Ala Phe Met
    50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Ser Pro Asn Ser Asn Phe Tyr Trp Tyr Phe Asp Val Trp Gly Gln
            100                 105                 110

Gly Thr Thr Ser
        115

<210> SEQ ID NO 31
<211> LENGTH: 116
<212> TYPE: PRT
<213> ORGANISM: Artificial sequence
<220> FEATURE:
<223> OTHER INFORMATION: Humanised VH construct A3

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ser Thr Asp Tyr Asn Ala Ala Phe Met
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Ser Pro Asn Ser Asn Phe Tyr Trp Tyr Phe Asp Val Trp Gly Gln
            100                 105                 110

Gly Thr Thr Ser
        115

<210> SEQ ID NO 32
<211> LENGTH: 116
<212> TYPE: PRT
<213> ORGANISM: Artificial sequence
<220> FEATURE:
<223> OTHER INFORMATION: Humanised VH construct A4

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ser Thr Asp Tyr Asn Ala Ala Phe Met
    50                  55                  60
```

```
Ser Arg Leu Thr Ile Ser Lys Asp Asn Ser Lys Asn Gln Val Ser Leu
 65                  70                  75                  80

Lys Leu Ser Ser Val Thr Ala Ala Asp Thr Ala Val Tyr Tyr Cys Ala
                 85                  90                  95

Lys Ser Pro Asn Ser Asn Phe Tyr Trp Tyr Phe Asp Val Trp Gly Gln
             100                 105                 110

Gly Thr Thr Ser
        115

<210> SEQ ID NO 33
<211> LENGTH: 116
<212> TYPE: PRT
<213> ORGANISM: Artificial sequence
<220> FEATURE:
<223> OTHER INFORMATION: Humanised VH construct B1

<400> SEQUENCE: 33

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
                20                  25                  30

Gly Val His Trp Val Arg Gln Ala Pro Gly Lys Gly Leu Glu Trp Val
            35                  40                  45

Ala Val Ile Trp Arg Gly Gly Ser Thr Asp Tyr Asn Ala Ala Phe Met
        50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Ser Pro Asn Ser Asn Phe Tyr Trp Tyr Phe Asp Val Trp Gly Arg
             100                 105                 110

Gly Thr Leu Val
        115

<210> SEQ ID NO 34
<211> LENGTH: 116
<212> TYPE: PRT
<213> ORGANISM: Artificial sequence
<220> FEATURE:
<223> OTHER INFORMATION: Humanised VH construct B2

<400> SEQUENCE: 34

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
                20                  25                  30

Gly Val His Trp Val Arg Gln Ala Pro Gly Lys Gly Leu Glu Trp Val
            35                  40                  45

Ala Val Ile Trp Arg Gly Gly Ser Thr Asp Tyr Asn Ala Ala Phe Met
        50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Pro Asn Ser Asn Phe Tyr Trp Tyr Phe Asp Val Trp Gly Arg
             100                 105                 110

Gly Thr Leu Val
```

<210> SEQ ID NO 35
<211> LENGTH: 116
<212> TYPE: PRT
<213> ORGANISM: Artificial sequence
<220> FEATURE:
<223> OTHER INFORMATION: Humanised VH construct B3

<400> SEQUENCE: 35

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Pro Asn Ser Asn Phe Tyr Trp Tyr Phe Asp Val Trp Gly Arg
            100                 105                 110

Gly Thr Leu Val
        115
```

<210> SEQ ID NO 36
<211> LENGTH: 116
<212> TYPE: PRT
<213> ORGANISM: Artificial sequence
<220> FEATURE:
<223> OTHER INFORMATION: Humanised VH construct B4

<400> SEQUENCE: 36

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Val
        35                  40                  45

Ala Val Ile Trp Arg Gly Gly Ser Thr Asp Tyr Asn Ala Ala Phe Met
    50                  55                  60

Ser Arg Leu Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Pro Asn Ser Asn Phe Tyr Trp Tyr Phe Asp Val Trp Gly Arg
            100                 105                 110

Gly Thr Leu Val
        115
```

<210> SEQ ID NO 37
<211> LENGTH: 106
<212> TYPE: PRT
<213> ORGANISM: Artificial sequence
<220> FEATURE:
<223> OTHER INFORMATION: Humanised VL construct L1

<400> SEQUENCE: 37

Glu Ile Val Leu Thr Gln Ser Pro Ala Thr Leu Ser Leu Ser Pro Gly
1               5                   10                  15

Glu Arg Ala Thr Leu Ser Cys Ser Gly Ser Ser Ser Val Ser Tyr Met
            20                  25                  30

Tyr Trp Tyr Gln Gln Lys Pro Gly Gln Ala Pro Arg Leu Leu Ile Tyr
            35                  40                  45

Asp Thr Ser Asn Leu Ala Ser Gly Ile Pro Ala Arg Phe Ser Gly Ser
        50                  55                  60

Gly Ser Gly Thr Asp Phe Thr Leu Thr Ile Ser Asn Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Leu Glu Ile Lys
            100                 105

<210> SEQ ID NO 38
<211> LENGTH: 106
<212> TYPE: PRT
<213> ORGANISM: Artificial sequence
<220> FEATURE:
<223> OTHER INFORMATION: Humanised VL construct L2

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Ser Gly Ser Ser Ser Val Ser Tyr Met
            20                  25                  30

Tyr Trp Tyr Gln Gln Lys Pro Gly Gln Ala Pro Arg Leu Leu Ile Glu
            35                  40                  45

Asp Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Asn Leu Glu Pro Glu
65                  70                  75                  80

Asp Phe Ala Val Tyr Tyr Cys Gln Gln Trp Ser Ser Tyr Pro Pro Thr
                85                  90                  95

Phe Gly Gln Gly Thr Lys Leu Glu Ile Lys
            100                 105

<210> SEQ ID NO 39
<211> LENGTH: 19
<212> TYPE: PRT
<213> ORGANISM: Homo sapiens

<400> SEQUENCE: 39

Met Gly Trp Ser Cys Ile Ile Leu Phe Leu Val Ala Thr Ala Thr Gly
1               5                   10                  15

Val His Ser

<210> SEQ ID NO 40
<211> LENGTH: 5
<212> TYPE: PRT
<213> ORGANISM: Mus sp.

<400> SEQUENCE: 40

Asp Tyr Asn Met Asp
1               5

<210> SEQ ID NO 41

```
<211> LENGTH: 17
<212> TYPE: PRT
<213> ORGANISM: Mus sp.

<400> SEQUENCE: 41

Asp Ile Asn Pro Asn Asn Gly Gly Thr Ile Asp Asn Gln Lys Phe Lys
1               5                   10                  15

Asp

<210> SEQ ID NO 42
<211> LENGTH: 12
<212> TYPE: PRT
<213> ORGANISM: Mus sp.

<400> SEQUENCE: 42

Gly Ile Tyr Tyr Tyr Gly Ser His Tyr Phe Asp Tyr
1               5                   10

<210> SEQ ID NO 43
<211> LENGTH: 10
<212> TYPE: PRT
<213> ORGANISM: Mus sp.

<400> SEQUENCE: 43

Ser Ala Thr Ser Ser Val Ser Val Met His
1               5                   10

<210> SEQ ID NO 44
<211> LENGTH: 7
<212> TYPE: PRT
<213> ORGANISM: Mus sp.

<400> SEQUENCE: 44

Asp Thr Ser Lys Leu Ala Ser
1               5

<210> SEQ ID NO 45
<211> LENGTH: 9
<212> TYPE: PRT
<213> ORGANISM: Mus sp.

<400> SEQUENCE: 45

Gln Gln Trp Ser Ser Asn Pro Leu Thr
1               5

<210> SEQ ID NO 46
<211> LENGTH: 121
<212> TYPE: PRT
<213> ORGANISM: Mus sp.

<400> SEQUENCE: 46

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ile Phe Thr Asp Tyr
                20                  25                  30

Asn Met Asp Trp Val Lys Gln Ser His Gly Lys Lys Leu Glu Trp Ile
            35                  40                  45

Gly Asp Ile Asn Pro Asn Asn Gly Gly Thr Ile Asp Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
```

-continued

```
                85                  90                  95
Ala Arg Gly Ile Tyr Tyr Tyr Gly Ser His Tyr Phe Asp Tyr Trp Gly
            100                 105                 110

Gln Gly Thr Thr Leu Thr Val Ser Ser
        115                 120

<210> SEQ ID NO 47
<211> LENGTH: 106
<212> TYPE: PRT
<213> ORGANISM: Mus sp.

<400> SEQUENCE: 47

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Ser Val Met
            20                  25                  30

His Trp Phe Gln Lys Lys Ser Gly Thr Ser Pro Lys Arg Trp Ile Tyr
        35                  40                  45

Asp Thr Ser Lys Leu Ala Ser Gly Val Pro Thr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Thr Ala Thr Tyr Tyr Cys Gln Gln Trp Ser Asn Pro Leu Thr
                85                  90                  95

Phe Gly Ser Gly Thr Lys Leu Glu Leu Lys
            100                 105

<210> SEQ ID NO 48
<211> LENGTH: 121
<212> TYPE: PRT
<213> ORGANISM: Artificial sequence
<220> FEATURE:
<223> OTHER INFORMATION: VH domain (humanised, B3)

<400> SEQUENCE: 48

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Asn Met Asp Trp Val Arg Gln Ala Pro Gly Gln Lys Leu Glu Trp Ile
        35                  40                  45

Gly Asp Ile Asn Pro Asn Gly Gly Thr Ile Asp Asn Gln Lys Phe
    50                  55                  60

Lys Asp Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ile Tyr Tyr Tyr Gly Ser His Tyr Phe Asp Tyr Trp Gly
            100                 105                 110

Gln Gly Thr Leu Val Thr Val Ser Ser
        115                 120

<210> SEQ ID NO 49
<211> LENGTH: 106
<212> TYPE: PRT
<213> ORGANISM: Artificial sequence
<220> FEATURE:
<223> OTHER INFORMATION: VL domain (humanised, L2)
```

-continued

```
<400> SEQUENCE: 49

Glu Ile Val Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Val Met
            20                  25                  30

His Trp Phe Gln Lys Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Asp Ile Lys
            100                 105

<210> SEQ ID NO 50
<211> LENGTH: 451
<212> TYPE: PRT
<213> ORGANISM: Artificial sequence
<220> FEATURE:
<223> OTHER INFORMATION: Heavy chain (humanised)

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Asn Met Asp Trp Val Arg Gln Ala Pro Gly Gln Lys Leu Glu Trp Ile
        35                  40                  45

Gly Asp Ile Asn Pro Asn Asn Gly Gly Thr Ile Asp Asn Gln Lys Phe
    50                  55                  60

Lys Asp Arg Ala Thr Leu Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ile Tyr Tyr Tyr Gly Ser His Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                    245                 250                 255
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 51
<211> LENGTH: 213
<212> TYPE: PRT
<213> ORGANISM: Artificial sequence
<220> FEATURE:
<223> OTHER INFORMATION: Light chain (humanised)

<400> SEQUENCE: 51

Glu Ile Val Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Val Met
            20                  25                  30

His Trp Phe Gln Lys Lys Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
```

-continued 145                 150                 155                 160
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 52
<211> LENGTH: 363
<212> TYPE: DNA
<213> ORGANISM: Mus sp.

<400> SEQUENCE: 52
gaggtccagc tgcaacagtc tggacctgag ctggtgaagc ctggggcttc agtgaagata    60
tcctgcaagg cctctggata catattcact gactacaaca tggactgggt gaagcagagc   120
catggaaaga aacttgagtg gattggagat attaatccta ataatggtgg tactatcgac   180
aaccagaagt tcaaggacaa ggccacattg actgtagaca gtcctccag cacagcctac    240 atggagctcc gcagcctgac atctgaggac actgcagtct attactgtgc aagagggatt   300
tattactacg gtagtcacta ctttgactat tggggccaag gcaccactct cacagtctcc   360
tca                                                                 363

<210> SEQ ID NO 53
<211> LENGTH: 318
<212> TYPE: DNA
<213> ORGANISM: Mus sp.

<400> SEQUENCE: 53
caaattgttc tcacccagtc tccagcaatc atgtctgcat ctccagggga aaggtcacc    60 atgacctgca gtgccacctc aagtgtaagt gtcatgcact ggttccagaa gaagtcaggt   120
acctccccca aaagatggat ttatgacaca tccaaactgg cttctggagt ccctactcgc   180
ttcagtggca gtgggtctgg gacctcttac tctctcacaa tcagtagcat ggaggctgaa   240
gatactgcca cttattactg ccagcagtgg agtagtaacc cactcacgtt cggttctggg   300
accaagctgg agctgaaa                                                 318

<210> SEQ ID NO 54
<211> LENGTH: 363
<212> TYPE: DNA
<213> ORGANISM: Artificial sequence
<220> FEATURE:
<223> OTHER INFORMATION: VH domain (humanised, PN, B3)

<400> SEQUENCE: 54
gaggtccagc tggtgcagtc tggggctgag gtgaagaagc ctggggcctc agtgaaggtt    60
tcctgcaagg catctggata catattcacc gactacaaca tggactgggt gcgacaggcc   120
cctggacaaa aacttgagtg gattggagat attaatccta ataatggtgg tactatcgac   180
aaccagaagt tcaaggacag agccaccttg accgtagaca gtccacgag cacagtctac    240 atggagctga gcagcctgag atctgaggac acggccgtgt attactgtgc gagagggatt   300
tattactacg gtagtcacta ctttgactat tggggccagg gaacactagt cacagtctcc   360
tca                                                                 363

<210> SEQ ID NO 55
<211> LENGTH: 318
<212> TYPE: DNA
<213> ORGANISM: Artificial sequence
<220> FEATURE:
<223> OTHER INFORMATION: VL domain (humanised, PN, L2)

<400> SEQUENCE: 55

| | | |
|---|---|---|
| gaaattgtgt tgacgcagtc tccatcctcc ctgtctgcat ctgttggaga cagagtcacc | 60 |
| atcacttgca gtgccacctc aagtgtaagt gtcatgcact ggttccagaa gaaaccaggg | 120 |
| aaagccccta agagatggat ctatgacaca tccaaactgg cttctggggt cccatcaagg | 180 |
| ttcagtggca gtggatctgg gacagattac actctcacca tcagcagtct gcaacctgaa | 240 |
| gattttgcaa cttattactg ccagcagtgg agtagtaacc cactcacgtt cggcggaggg | 300 |
| accaaagtgg atatcaaa | 318 |

<210> SEQ ID NO 56
<211> LENGTH: 1353
<212> TYPE: DNA
<213> ORGANISM: Artificial sequence
<220> FEATURE:
<223> OTHER INFORMATION: Heavy chain (humanised, PN)

<400> SEQUENCE: 56

| | | |
|---|---|---|
| gaggtccagc tggtgcagtc tggggctgag gtgaagaagc ctggggcctc agtgaaggtt | 60 |
| tcctgcaagg catctggata catattcacc gactacaaca tggactgggt gcgacaggcc | 120 |
| cctggacaaa aacttgagtg gattggagat attaatccta ataatggtgg tactatcgac | 180 |
| aaccagaagt tcaaggacag agccaccttg accgtagaca gtccacgag cacagtctac | 240 |
| atggagctga gcagcctgag atctgaggac acggccgtgt attactgtgc gagagggatt | 300 |
| tattactacg gtagtcacta ctttgactat tggggccagg gaacactagt cacagtctcc | 360 |
| tcagcctcca ccaagggccc atcggtcttc cccctggcac cctcctccaa gagcacctct | 420 |
| gggggcacag cggccctggg ctgcctggtc aaggactact ccccgaacc ggtgacggtg | 480 |
| tcgtggaact caggcgccct gaccagcggc gtgcacacct tcccggctgt cctacagtcc | 540 |
| tcaggactct actccctcag cagcgtggtg accgtgccct ccagcagctt gggcacccag | 600 |
| acctacatct gcaacgtgaa tcacaagccc agcaacacca aggtggacaa gaaagttgag | 660 |
| cccaaatctt gtgacaaaac tcacacatgc ccaccgtgcc cagcacctga actcctgggg | 720 |
| ggaccgtcag tcttcctctt ccccccaaaa cccaaggaca cctcatgat ctcccggacc | 780 |
| cctgaggtca catgcgtggt ggtggacgtg agccacgaag accctgaggt caagttcaac | 840 |
| tggtacgtgg acggcgtgga ggtgcataat gccaagacaa agccgcggga ggagcagtac | 900 |
| aacagcacgt accgtgtggt cagcgtcctc accgtcctgc accaggactg gctgaatggc | 960 |
| aaggagtaca agtgcaaggt ctccaacaaa gccctcccag cccccatcga gaaaaccatc | 1020 |
| tccaaagcca agggcagccc cgagaaccca caggtgtaca ccctgccccc atcccgggat | 1080 |
| gagctgacca agaaccaggt cagcctgacc tgcctggtca aaggcttcta tcccagcgac | 1140 |
| atcgccgtgg agtgggagag caatgggcag ccggagaaca actacaagac cacgcctccc | 1200 |
| gtgctggact ccgacggctc cttcttcctc tacagcaagc tcaccgtgga caagagcagg | 1260 |
| tggcagcagg ggaacgtctt ctcatgctcc gtgatgcatg aggctctgca caaccactac | 1320 |
| acgcagaaga gcctctccct gtctccgggt aaa | 1353 |

<210> SEQ ID NO 57
<211> LENGTH: 639
<212> TYPE: DNA
<213> ORGANISM: Artificial sequence
<220> FEATURE:
<223> OTHER INFORMATION: Light chain (humanised, PN)

<400> SEQUENCE: 57

| | | | | | |
|---|---|---|---|---|---|
| gaaattgtgt | tgacgcagtc | tccatcctcc | ctgtctgcat | ctgttggaga | cagagtcacc | 60 |
| atcacttgca | gtgccacctc | aagtgtaagt | gtcatgcact | ggttccagaa | gaaaccaggg | 120 |
| aaagccccta | agagatggat | ctatgacaca | tccaaactgg | cttctggggt | cccatcaagg | 180 |
| ttcagtggca | gtggatctgg | gacagattac | actctcacca | tcagcagtct | gcaacctgaa | 240 |
| gattttgcaa | cttattactg | ccagcagtgg | agtagtaacc | cactcacgtt | cggcggaggg | 300 |
| accaaagtgg | atatcaaacg | tacggtggct | gcaccatctg | tcttcatctt | cccgccatct | 360 |
| gatgagcagt | tgaaatctgg | aactgcctct | gttgtgtgcc | tgctgaataa | cttctatccc | 420 |
| agagaggcca | aagtacagtg | gaaggtggac | aacgccctcc | aatcgggtaa | ctcccaggag | 480 |
| agtgtcacag | agcaggacag | caaggacagc | acctacagcc | tcagcagcac | cctgacgctg | 540 |
| agcaaagcag | actacgagaa | acacaaagtc | tacgcctgcg | aagtcaccca | tcagggcctg | 600 |
| agctcgcccg | tcacaaagag | cttcaacagg | ggagagtgt | | | 639 |

<210> SEQ ID NO 58
<211> LENGTH: 37
<212> TYPE: DNA
<213> ORGANISM: Artificial sequence
<220> FEATURE:
<223> OTHER INFORMATION: VH forward primer

<400> SEQUENCE: 58
gatgaagctt gccaccatgg gatggagctg ggtcttt                37

<210> SEQ ID NO 59
<211> LENGTH: 37
<212> TYPE: DNA
<213> ORGANISM: Artificial sequence
<220> FEATURE:
<223> OTHER INFORMATION: VL forward primer

<400> SEQUENCE: 59
gatgaagctt gccaccatgg atttacaggt gcagatt                37

<210> SEQ ID NO 60
<211> LENGTH: 31
<212> TYPE: DNA
<213> ORGANISM: Artificial sequence
<220> FEATURE:
<223> OTHER INFORMATION: VL reverse primer

<400> SEQUENCE: 60
gatgcgtacg tttcagctcc agcttggtcc c                      31

<210> SEQ ID NO 61
<211> LENGTH: 450
<212> TYPE: PRT
<213> ORGANISM: Artificial sequence
<220> FEATURE:
<223> OTHER INFORMATION: Heavy chain (humanised, Fc mutated)

<400> SEQUENCE: 61

Gln Val Gln Leu Val Glu Ser Gly Gly Gly Val Val Gln Pro Gly Arg

-continued

```
1               5                    10                   15
Ser Leu Arg Leu Ser Cys Ala Ala Ser Gly Phe Ser Leu Thr Asn Tyr
            20                  25                  30
Gly Val His Trp Val Arg Gln Ala Pro Gly Lys Gly Leu Glu Trp Val
            35                  40                  45
Ala Val Ile Trp Arg Gly Gly Ser Thr Asp Tyr Asn Ala Ala Phe Met
            50                  55                  60
Ser Arg Phe Thr Ile Ser Lys Asp Asn Ser Lys Asn Thr Leu Tyr Leu
65                  70                  75                  80
Gln Met Asn Ser Leu Arg Ala Glu Asp Thr Ala Val Tyr Tyr Cys Ala
            85                  90                  95
Lys Ser Pro Asn Ser Asn Phe Tyr Trp Tyr Phe Asp Val Trp Gly Arg
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
            210                 215                 220
Lys Thr His Thr Cys Pro Pro Cys Pro Ala Pro Glu Leu Ala Gly Ala
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
            290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly Lys
    450

<210> SEQ ID NO 62
<211> LENGTH: 1350
<212> TYPE: DNA
<213> ORGANISM: Artificial sequence
<220> FEATURE:
<223> OTHER INFORMATION: Heavy chain (humanised, Fc mutated, PN)

<400> SEQUENCE: 62
caggtgcagc tggtggagtc tgggggaggc gtggtccagc ctgggaggtc cctgagactc      60
tcctgtgcag cgtctggatt ctcattaact aattatggtg tacactgggt ccgccaggct     120
ccaggcaagg ggctggagtg ggtggcagtg atatggagag gtggaagcac agactacaat     180
gcagctttca tgtcccgatt caccatctcc aaggacaatt ccaagaacac gctgtatctg     240
caaatgaaca gcctgagagc cgaggacacg gctgtgtatt actgtgcgaa aagtccgaat     300
agtaactttt actggtattt cgatgtctgg ggccgtggca cactagtcac agtctcctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cgcggggggca     720 ccgtcagtct tcctcttccc cccaaaaccc aaggacaccc tcatgatctc ccggaccccct    780 gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc ccatcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa                                    1350

<210> SEQ ID NO 63
<211> LENGTH: 252
<212> TYPE: PRT
<213> ORGANISM: Macaca fascicularis

<400> SEQUENCE: 63

Met Gly Val Pro Leu Thr Arg Arg Thr Leu Leu Ser Leu Ile Leu Ala
1               5                   10                  15

Leu Leu Phe Pro Ser Met Ala Ser Met Ala Ala Met Gly Ser Cys Ser
            20                  25                  30

Lys Glu Tyr Arg Met Leu Leu Gly Gln Leu Gln Lys Gln Thr Asp Leu
        35                  40                  45
```

Met Gln Asp Thr Ser Arg Leu Leu Asp Pro Tyr Ile Arg Ile Gln Gly
            50                  55                  60

Leu Asp Ile Pro Lys Leu Arg Glu His Cys Arg Glu Ser Pro Gly Ala
 65                  70                  75                  80

Phe Pro Ser Glu Glu Thr Leu Arg Gly Leu Gly Arg Arg Gly Phe Leu
                 85                  90                  95

Gln Thr Leu Asn Ala Thr Leu Gly Cys Val Leu His Arg Leu Ala Asp
            100                 105                 110

Leu Glu Gln His Leu Pro Lys Ala Gln Asp Leu Glu Arg Ser Gly Leu
        115                 120                 125

Asn Ile Glu Asp Leu Glu Lys Leu Gln Met Ala Arg Pro Asn Val Leu
130                 135                 140

Gly Leu Arg Asn Asn Val Tyr Cys Met Ala Gln Leu Leu Asp Asn Ser
145                 150                 155                 160

Asp Met Thr Glu Pro Thr Lys Ala Gly Arg Gly Thr Pro Gln Pro Pro
                165                 170                 175

Thr Pro Thr Pro Thr Ser Asp Val Phe Gln Arg Lys Leu Glu Gly Cys
            180                 185                 190

Ser Phe Leu Arg Gly Tyr His Arg Phe Met His Ser Val Gly Arg Ile
        195                 200                 205

Phe Ser Lys Trp Gly Glu Ser Pro Asn Arg Ser Arg Arg His Ser Pro
210                 215                 220

His Gln Ala Leu Arg Lys Gly Val Arg Arg Thr Arg Pro Ser Arg Lys
225                 230                 235                 240

Gly Asn Arg Leu Met Pro Arg Gly Gln Leu Pro Arg
                245                 250

<210> SEQ ID NO 64
<211> LENGTH: 759
<212> TYPE: DNA
<213> ORGANISM: Macaca fascicularis

<400> SEQUENCE: 64
atgggggtac cgctcacacg gaggacgctg ctcagtctga tccttgcact cctgtttcca      60
agcatggcaa gcatggcggc tatgggcagc tgctcgaaag agtaccgcat gctccttggc     120
cagctccaga gcagacaga tctcatgcag gacaccagca ggctcctgga cccctatata     180
cgtatccaag gcctggatat tcctaaactg agagagcact gcagagagag ccctggggcc     240
ttccccagcg aggagaccct gaggggggctg ggcaggcggg gcttcctaca gacgctcaat     300
gccacactgg gctgcgtcct gcacagactg gccgacttag agcagcatct ccccaaggcc     360
caggacttgg agaggtctgg gctgaacata gaggacttag agaagctgca gatggcgagg     420
ccgaatgtcc tcgggctcag gaacaacgtc tactgcatgg cccagctgct ggacaactca     480
gacatgactg agcccacgaa ggccggccgg gggacccctc agccgccac ccccaccct     540 acctcagatg tttttcagcg caagctggag ggctgcagtt tcctgcgtgg ctaccatcgc     600
ttcatgcact cagtggggcg gatcttcagc aagtgggggg agagcccgaa ccggagccgg     660
agacacagcc cccaccaggc cctgcggaag ggggtgcgca ggacgagacc ctccaggaaa     720
ggcaatagac tcatgcccag gggacagctg ccccggtag                           759

<210> SEQ ID NO 65
<211> LENGTH: 28
<212> TYPE: DNA
<213> ORGANISM: Artificial sequence

```
-continued

<220> FEATURE:
<223> OTHER INFORMATION: VH reverse primer

<400> SEQUENCE: 65
gatggactag tgtgccttgg ccccaata                                             28
```